(12) United States Patent
Löving et al.

(10) Patent No.: US 12,383,501 B2
(45) Date of Patent: Aug. 12, 2025

(54) PRODUCTION OF SALIPRO PARTICLES

(71) Applicant: Salipro Biotech AB, Stockholm (SE)

(72) Inventors: Robin Löving, Stockholm (SE); Jens Frauenfeld, Stockholm (SE)

(73) Assignee: Salipro Biotech AB, Stockholm (SE)

( * ) Notice: Subject to any disclaimer, the term of this patent is extended or adjusted under 35 U.S.C. 154(b) by 798 days.

(21) Appl. No.: 17/603,936

(22) PCT Filed: Apr. 15, 2020

(86) PCT No.: PCT/EP2020/060594
§ 371 (c)(1),
(2) Date: Oct. 14, 2021

(87) PCT Pub. No.: WO2020/212423
PCT Pub. Date: Oct. 22, 2020

(65) Prior Publication Data
US 2022/0192982 A1 Jun. 23, 2022

(30) Foreign Application Priority Data
Apr. 15, 2019 (EP) .................... 19169321

(51) Int. Cl.
*A61K 9/1275* (2025.01)
*A61K 9/1274* (2025.01)
*A61K 47/42* (2017.01)

(52) U.S. Cl.
CPC .......... *A61K 9/1275* (2013.01); *A61K 9/1274* (2013.01); *A61K 47/42* (2013.01)

(58) Field of Classification Search
CPC ..... A61K 9/1275; A61K 9/1274; A61K 47/42
See application file for complete search history.

(56) References Cited

FOREIGN PATENT DOCUMENTS

| | | |
|---|---|---|
| EP | 2745834 A1 | 6/2014 |
| EP | 3284460 A1 | 2/2018 |
| JP | 2016-504312 A | 2/2016 |
| WO | 2005081743 A2 | 9/2005 |
| WO | 2014095576 A1 | 6/2014 |
| WO | 2016029308 A1 | 3/2016 |
| WO | 2018033647 A1 | 2/2018 |

OTHER PUBLICATIONS

Office Action issued in related Japanese Patent Application No. 2021-559753, dated Mar. 19, 2024.
Frauenfeld, Jens, et al., "A saposin-lipoprotein nanoparticle system for membrane proteins", Nature Methods, vol. 3, No. 4, Apr. 2016, Epub Mar. 7, 2016, p. 345-351, doi: 10.1038/nmeth.3801.
International Search Report, PCT/EP2020/060594, Jun. 16, 2020, 10 pages.

*Primary Examiner* — Marsha Tsay
(74) *Attorney, Agent, or Firm* — Honigman LLP

(57) ABSTRACT

The invention relates to a process for preparing saposin lipoprotein particles, comprising a saposin-like protein, lipids and optionally a hydrophobic agent wherein the saposin-like protein or the hydrophobic agent is selectively bound to a support to allow the self-assembly of the saposin lipoprotein particles. The process of the invention comprises the step of a.) providing the hydrophobic agent and lipids, b.1)/b.2 contacting the hydrophobic agent or the saposin-like protein with a support that is capable of selectively binding either of the two molecules to the support, c.1)/c.2) contacting the support-bound particle components with the remaining particle components, either the saposin-like protein or the hydrophobic agent, to allow for the self-assembly of the saposin lipoprotein particle on the support and d.) optionally eluting the support-bound saposin lipoprotein particles.

20 Claims, 20 Drawing Sheets
Specification includes a Sequence Listing.

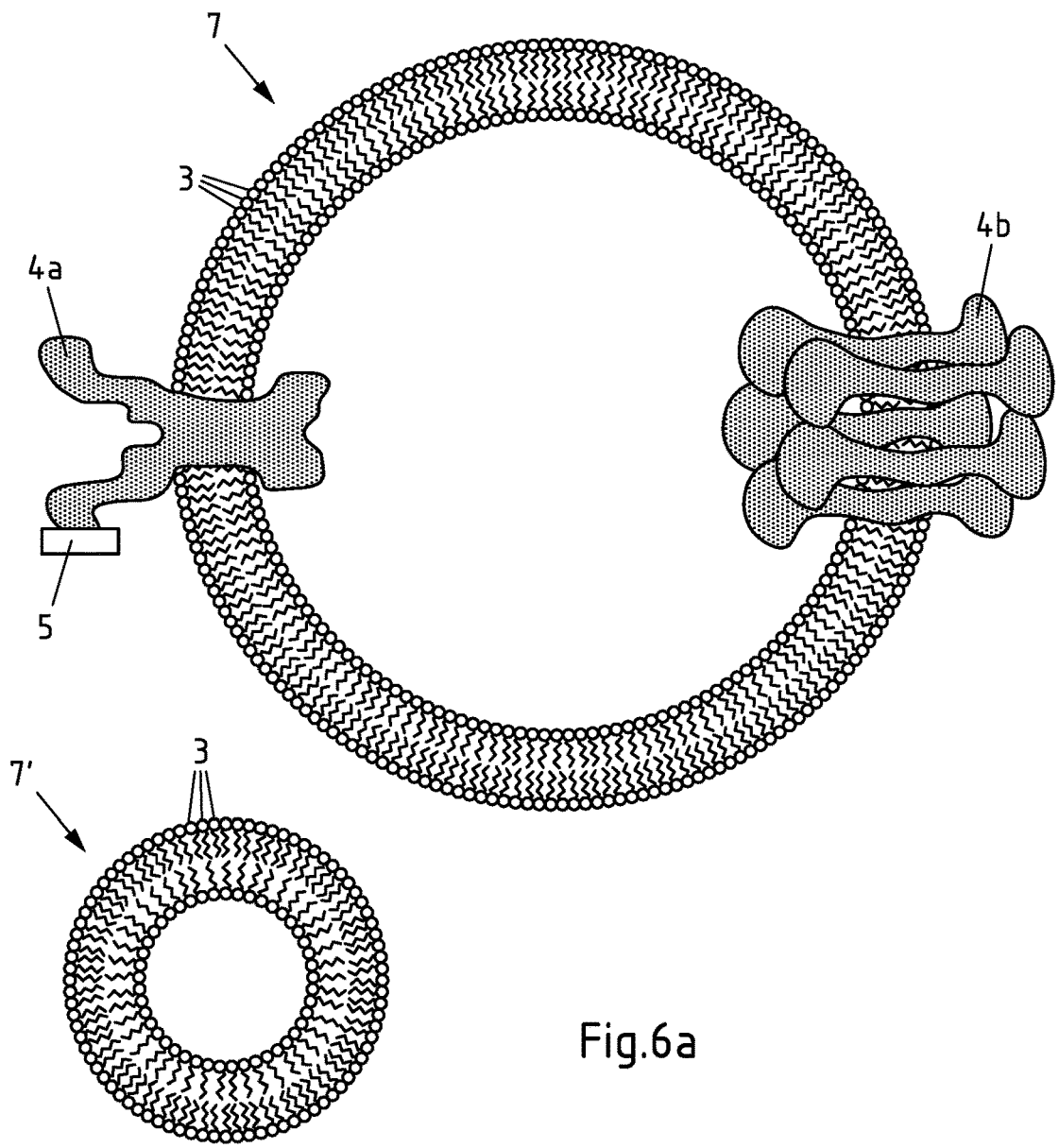
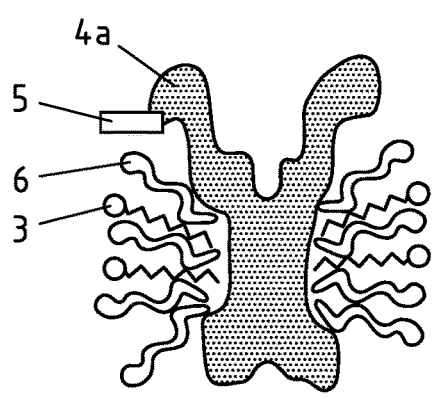
Fig.6a
Fig.6b
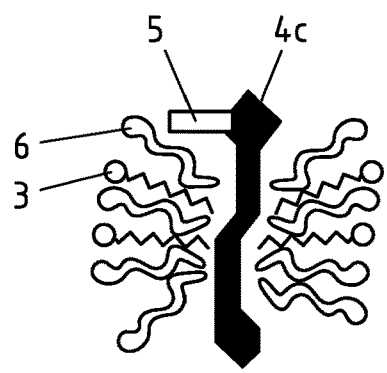
Fig.6c

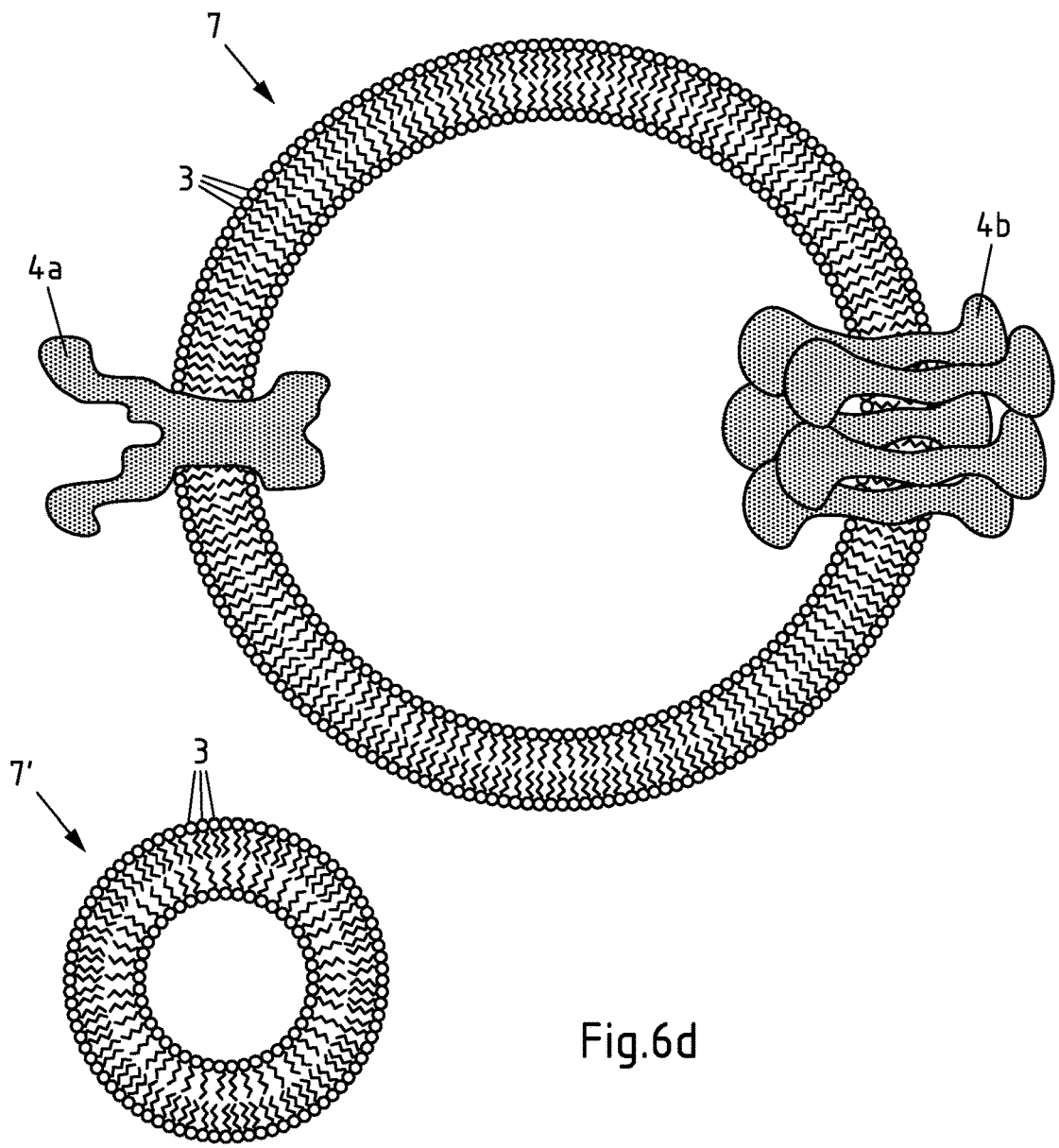
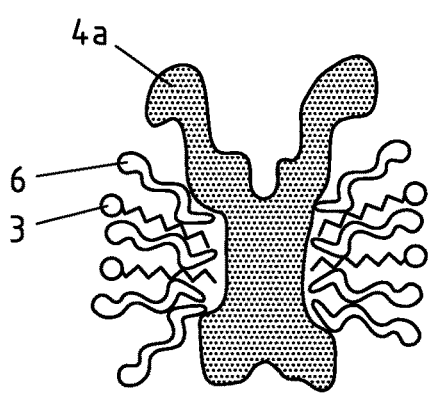
Fig.6d
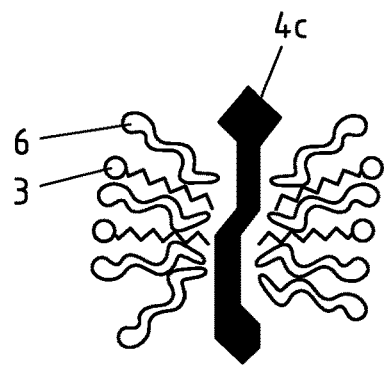
Fig.6e        Fig.6f

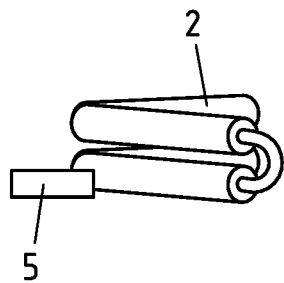 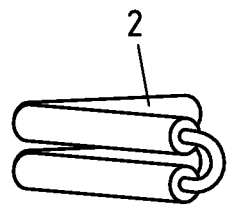
Fig.7a  Fig.7b
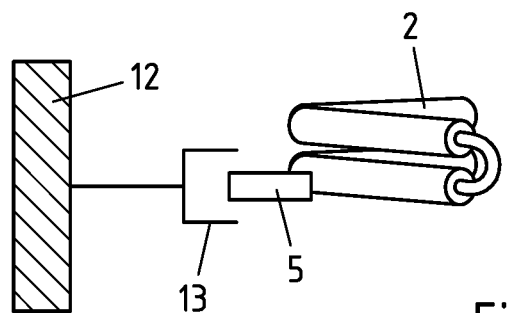
Fig.8a
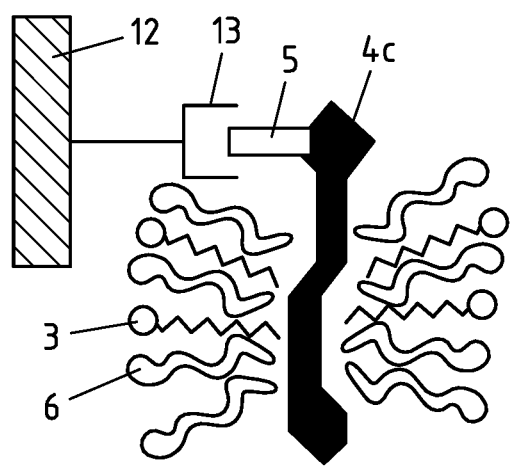
Fig.8b

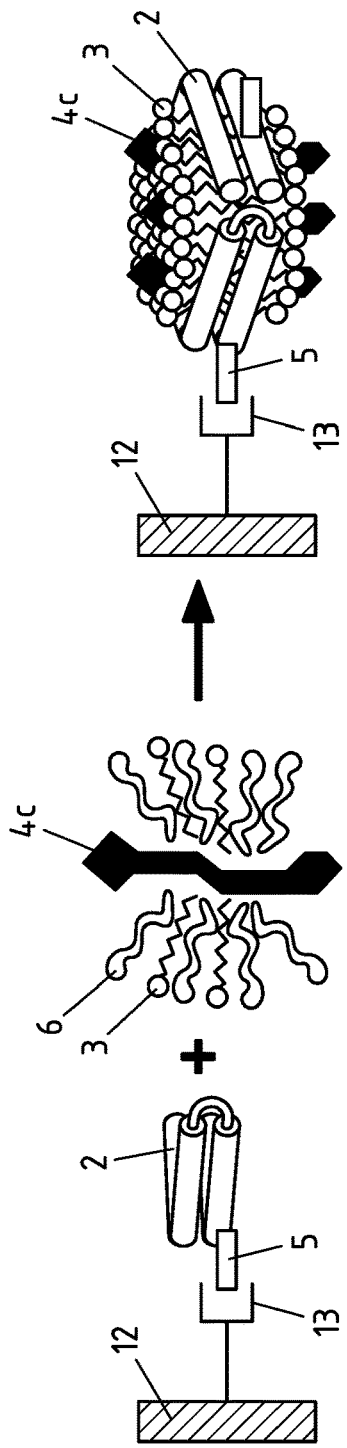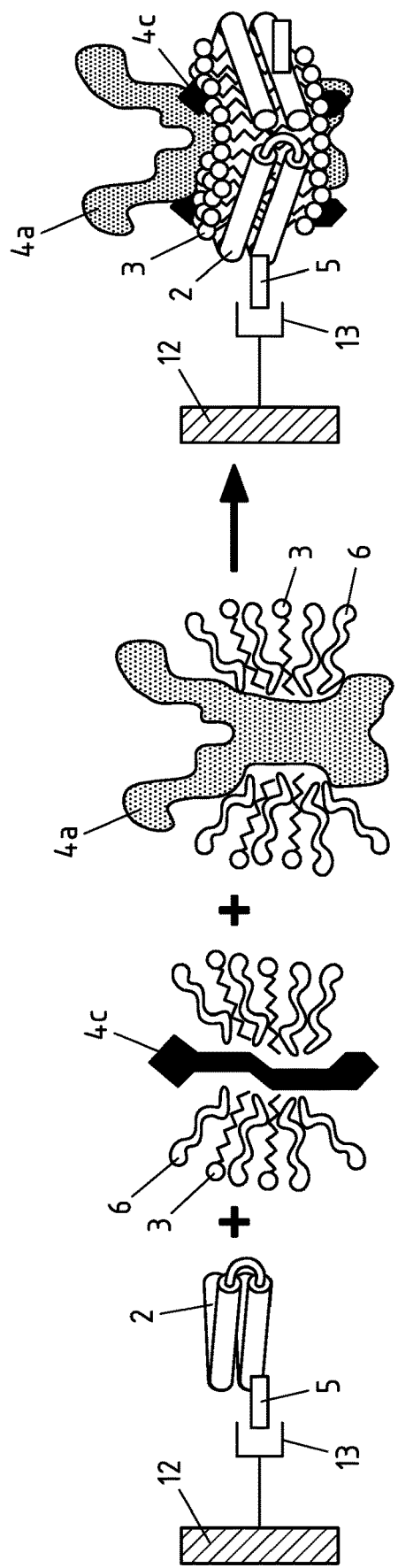
Fig.10c
Fig.10d

Fig.14b

SEQUENCE LISTING

```
<160> NUMBER OF SEQ ID NOS: 50

<210> SEQ ID NO 1
<211> LENGTH: 81
<212> TYPE: PRT
<213> ORGANISM: Homo sapiens

<400> SEQUENCE: 1

Ser Leu Pro Cys Asp Ile Cys Lys Asp Val Val Thr Ala Ala Gly Asp
1               5                   10                  15

Met Leu Lys Asp Asn Ala Thr Glu Glu Glu Ile Leu Val Tyr Leu Glu
            20                  25                  30

Lys Thr Cys Asp Trp Leu Pro Lys Pro Asn Met Ser Ala Ser Cys Lys
        35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser

<210> SEQ ID NO 2
<211> LENGTH: 79
<212> TYPE: PRT
<213> ORGANISM: Homo sapiens

<400> SEQUENCE: 2

Gly Asp Val Cys Gln Asp Cys Ile Gln Met Val Thr Asp Ile Gln Thr
1               5                   10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
        35                  40                  45

Asn Tyr Ile Ser Gln Tyr Ser Glu Ile Ala Ile Gln Met Met Met His
    50                  55                  60

Met Gln Pro Lys Glu Ile Cys Ala Leu Val Gly Phe Cys Asp Glu
65                  70                  75

<210> SEQ ID NO 3
<211> LENGTH: 80
<212> TYPE: PRT
<213> ORGANISM: Homo sapiens

<400> SEQUENCE: 3

Asp Val Tyr Cys Glu Val Cys Glu Phe Leu Val Lys Glu Val Thr Lys
1               5                   10                  15

Leu Ile Asp Asn Asn Lys Thr Glu Lys Glu Ile Leu Asp Ala Phe Asp
            20                  25                  30

Lys Met Cys Ser Lys Leu Pro Lys Ser Leu Ser Glu Glu Cys Gln Glu
        35                  40                  45
```

```
Val Val Asp Thr Tyr Gly Ser Ser Ile Leu Ser Ile Leu Leu Glu Glu
         50                  55                  60

Val Ser Pro Glu Leu Val Cys Ser Met Leu His Leu Cys Ser Gly Thr
 65                  70                  75                  80

<210> SEQ ID NO 4
<211> LENGTH: 78
<212> TYPE: PRT
<213> ORGANISM: Homo sapiens

<400> SEQUENCE: 4

Gly Phe Cys Glu Val Cys Lys Lys Leu Val Gly Tyr Leu Asp Arg Asn
 1               5                  10                  15

Leu Glu Lys Asn Ser Thr Lys Gln Glu Ile Leu Ala Ala Leu Glu Lys
             20                  25                  30

Gly Cys Ser Phe Leu Pro Asp Pro Tyr Gln Lys Gln Cys Asp Gln Phe
         35                  40                  45

Val Ala Glu Tyr Glu Pro Val Leu Ile Glu Ile Leu Val Glu Val Met
     50                  55                  60

Asp Pro Ser Phe Val Cys Leu Lys Ile Gly Ala Cys Pro Ser
 65                  70                  75

<210> SEQ ID NO 5
<211> LENGTH: 145
<212> TYPE: PRT
<213> ORGANISM: Homo sapiens

<400> SEQUENCE: 5

Met Ala Thr Trp Ala Leu Leu Leu Leu Ala Ala Met Leu Leu Gly Asn
 1               5                  10                  15

Pro Gly Leu Val Phe Ser Arg Leu Ser Pro Glu Tyr Tyr Asp Leu Ala
             20                  25                  30

Arg Ala His Leu Arg Asp Glu Glu Lys Ser Cys Pro Cys Leu Ala Gln
         35                  40                  45

Glu Gly Pro Gln Gly Asp Leu Leu Thr Lys Thr Gln Glu Leu Gly Arg
     50                  55                  60

Asp Tyr Arg Thr Cys Leu Thr Ile Val Gln Lys Leu Lys Lys Met Val
 65                  70                  75                  80

Asp Lys Pro Thr Gln Arg Ser Val Ser Asn Ala Ala Thr Arg Val Cys
             85                  90                  95

Arg Thr Gly Arg Ser Arg Trp Arg Asp Val Cys Arg Asn Phe Met Arg
        100                 105                 110

Arg Tyr Gln Ser Arg Val Thr Gln Gly Leu Val Ala Gly Glu Thr Ala
        115                 120                 125

Gln Gln Ile Cys Glu Asp Leu Arg Leu Cys Ile Pro Ser Thr Gly Pro
    130                 135                 140

Leu
145

<210> SEQ ID NO 6
<211> LENGTH: 129
<212> TYPE: PRT
<213> ORGANISM: Sus scrofa

<400> SEQUENCE: 6

Pro Gly Leu Ala Phe Ser Gly Leu Thr Pro Glu His Ser Ala Leu Ala
 1               5                  10                  15
```

Arg Ala His Pro Cys Asp Gly Glu Gln Phe Cys Gln Asn Leu Ala Pro
                20                  25                  30

Glu Asp Pro Gln Gly Asp Gln Leu Leu Gln Arg Glu Glu Leu Gly Leu
            35                  40                  45

Ile Cys Glu Ser Cys Arg Lys Ile Ile Gln Lys Leu Glu Asp Met Val
 50                  55                  60

Gly Pro Gln Pro Asn Glu Asp Thr Val Thr Gln Ala Ala Ser Arg Val
 65                  70                  75                  80

Cys Asp Lys Met Lys Ile Leu Arg Gly Val Cys Lys Lys Ile Met Arg
                85                  90                  95

Thr Phe Leu Arg Arg Ile Ser Lys Asp Ile Leu Thr Gly Lys Lys Pro
            100                 105                 110

Gln Ala Ile Cys Val Asp Ile Lys Ile Cys Lys Glu Lys Thr Gly Leu
        115                 120                 125

Ile

<210> SEQ ID NO 7
<211> LENGTH: 77
<212> TYPE: PRT
<213> ORGANISM: Entamoeba histolytica

<400> SEQUENCE: 7

Ile Pro Val Leu Cys Pro Val Cys Thr Ser Leu Val Gly Lys Leu Ile
1               5                   10                  15

Asp Leu Val Leu Gly Gly Ala Val Asp Lys Val Thr Asp Tyr Leu Glu
            20                  25                  30

Thr Leu Cys Ala Lys Ala Asp Gly Leu Val Glu Thr Leu Cys Thr Lys
        35                  40                  45

Ile Val Ser Tyr Gly Ile Asp Lys Leu Ile Glu Lys Ile Leu Glu Gly
    50                  55                  60

Gly Ser Ala Lys Leu Ile Cys Gly Leu Ile His Ala Cys
65                  70                  75

<210> SEQ ID NO 8
<211> LENGTH: 75
<212> TYPE: PRT
<213> ORGANISM: Entamoeba dispar

<400> SEQUENCE: 8

Val Val Cys Pro Val Cys Thr Ser Leu Val Gly Lys Leu Ile Asp Phe
1               5                   10                  15

Val Ile Gly Gly Ala Val Asp Lys Ala Thr Asp Tyr Leu Glu Thr Leu
            20                  25                  30

Cys Ala Lys Ala Asp Gly Val Ile Glu Thr Val Cys Ser Lys Ile Val
        35                  40                  45

Ser Tyr Gly Ile Asp Lys Leu Ile Glu Lys Ile Ile Glu Gly Gly Ser
    50                  55                  60

Ala Lys Leu Ile Cys Gly Leu Ile His Ala Cys
65                  70                  75

<210> SEQ ID NO 9
<211> LENGTH: 77
<212> TYPE: PRT
<213> ORGANISM: Entamoeba histolytica

<400> SEQUENCE: 9

Gly Ala Ile Leu Cys Asn Leu Cys Lys Asp Thr Val Lys Leu Val Glu
1               5                   10                  15

```
Asn Leu Leu Thr Val Asp Gly Ala Gln Ala Val Arg Gln Tyr Ile Asp
            20                  25                  30

Asn Leu Cys Gly Lys Ala Ser Gly Phe Leu Gly Thr Leu Cys Glu Lys
        35                  40                  45

Ile Leu Ser Phe Gly Val Asp Glu Leu Val Lys Leu Ile Glu Asn His
50                  55                  60

Val Asp Pro Val Val Cys Glu Lys Ile His Ala Cys
65                  70                  75

<210> SEQ ID NO 10
<211> LENGTH: 75
<212> TYPE: PRT
<213> ORGANISM: Entamoeba dispar

<400> SEQUENCE: 10

Gly Leu Cys Asn Leu Cys Lys Asp Thr Val Asn Leu Ile Glu Asn Leu
1               5                   10                  15

Leu Thr Val Asp Gly Ala Gln Ala Val Arg Gln Tyr Ile Asp Asn Leu
            20                  25                  30

Cys Ala Lys Ala Asp Gly Phe Leu Gly Thr Leu Cys Asn Lys Ile Leu
        35                  40                  45

Ser Phe Gly Val Asp Glu Leu Val Lys Leu Ile Glu Asn His Val Asp
50                  55                  60

Pro Val Val Ile Cys Glu Lys Ile His Ala Cys
65                  70                  75

<210> SEQ ID NO 11
<211> LENGTH: 77
<212> TYPE: PRT
<213> ORGANISM: Entamoeba histolytica

<400> SEQUENCE: 11

Gly Glu Ile Leu Cys Asn Leu Cys Thr Gly Leu Ile Asn Thr Leu Glu
1               5                   10                  15

Asn Leu Leu Thr Thr Lys Gly Ala Asp Lys Val Lys Asp Tyr Ile Ser
            20                  25                  30

Ser Leu Cys Asn Lys Ala Ser Gly Phe Ile Ala Thr Leu Cys Thr Lys
        35                  40                  45

Val Leu Asp Phe Gly Ile Asp Lys Leu Ile Gln Leu Ile Glu Asp Lys
50                  55                  60

Val Asp Ala Asn Ala Ile Cys Ala Lys Ile His Ala Cys
65                  70                  75

<210> SEQ ID NO 12
<211> LENGTH: 75
<212> TYPE: PRT
<213> ORGANISM: Entamoeba dispar

<400> SEQUENCE: 12

Ile Val Cys Asn Leu Cys Thr Gly Leu Ile Asn Thr Leu Glu Asn Leu
1               5                   10                  15

Leu Thr Thr Lys Gly Ala Asp Lys Val Lys Asp Tyr Ile Asp Ser Leu
            20                  25                  30

Cys Asn Lys Ala Ser Gly Phe Ile Ala Thr Leu Cys Thr Lys Val Leu
        35                  40                  45

Asp Phe Gly Val Asp Lys Leu Ile Gln Leu Ile Glu Asp Lys Val Asp
50                  55                  60
```

```
Ala Asn Ala Ile Cys Ala Lys Ile His Ala Cys
 65                  70                  75

<210> SEQ ID NO 13
<211> LENGTH: 83
<212> TYPE: PRT
<213> ORGANISM: Sus scrofa

<400> SEQUENCE: 13

Gly Leu Ile Cys Glu Ser Cys Arg Lys Ile Ile Gln Lys Leu Glu Asp
  1               5                  10                  15

Met Val Gly Pro Gln Pro Asn Glu Asp Thr Val Thr Gln Ala Ala Ser
             20                  25                  30

Arg Val Cys Asp Lys Met Lys Ile Leu Arg Gly Val Cys Lys Lys Ile
         35                  40                  45

Met Arg Thr Phe Leu Arg Arg Ile Ser Lys Asp Ile Leu Thr Gly Lys
 50                  55                  60

Lys Pro Gln Ala Ile Cys Val Asp Ile Lys Ile Cys Lys Glu Lys Thr
 65                  70                  75                  80

Gly Leu Ile

<210> SEQ ID NO 14
<211> LENGTH: 78
<212> TYPE: PRT
<213> ORGANISM: Sus scrofa

<400> SEQUENCE: 14

Gly Tyr Phe Cys Glu Ser Cys Arg Lys Ile Ile Gln Lys Leu Glu Asp
  1               5                  10                  15

Met Val Gly Pro Gln Pro Asn Glu Asp Thr Val Thr Gln Ala Ala Ser
             20                  25                  30

Gln Val Cys Asp Lys Leu Lys Ile Leu Arg Gly Leu Cys Lys Lys Ile
         35                  40                  45

Met Arg Ser Phe Leu Arg Arg Ile Ser Trp Asp Ile Leu Thr Gly Lys
 50                  55                  60

Lys Pro Gln Ala Ile Cys Val Asp Ile Lys Ile Cys Lys Glu
 65                  70                  75

<210> SEQ ID NO 15
<211> LENGTH: 83
<212> TYPE: PRT
<213> ORGANISM: Equus caballus

<400> SEQUENCE: 15

Gly Ile Ala Cys Trp Ser Cys Arg Lys Ile Leu Gln Lys Leu Glu Asp
  1               5                  10                  15

Leu Val Gly Glu Gln Pro Asn Glu Ala Thr Ile Asn Glu Ala Ala Ser
             20                  25                  30

Arg Val Cys Arg Asn Leu Gly Leu Leu Arg Gly Ala Cys Lys Lys Ile
         35                  40                  45

Met Arg Thr Cys Leu Arg Leu Ile Ser Arg Asp Ile Leu Ala Gly Lys
 50                  55                  60

Lys Pro Gln Glu Val Cys Val Asp Ile Lys Leu Cys Lys His Lys Ala
 65                  70                  75                  80

Gly Leu Ile

<210> SEQ ID NO 16
<211> LENGTH: 84
```

<212> TYPE: PRT
<213> ORGANISM: Bos taurus

<400> SEQUENCE: 16

```
Gly Leu Leu Cys Gly Ser Cys Gln Arg Ile Ile Gln His Leu Met Asp
1               5                   10                  15

Lys Leu Gly Asp Gln Pro Asp Glu Asn Thr Val Ile Glu Ala Ala Ser
            20                  25                  30

Lys Val Cys Gly Lys Met Gly Pro Leu Lys Gly Leu Cys Lys Ser Ile
        35                  40                  45

Thr Lys Arg Phe Leu Arg Arg Ile Ala Ala Asp Ile Thr Ala Gly Lys
    50                  55                  60

Thr Ser Arg Val Val Cys Glu Asp Ile Lys Met Cys Lys Ser Lys Pro
65                  70                  75                  80

Val Gly Phe Ile
```

<210> SEQ ID NO 17
<211> LENGTH: 81
<212> TYPE: PRT
<213> ORGANISM: Fasciola hepatica

<400> SEQUENCE: 17

```
Glu Glu Pro His Leu Asp Ile Ser Leu Cys Glu Ser Cys Thr Asn Thr
1               5                   10                  15

Val Asn Leu Val Lys Arg Leu Leu Gln Asn Ser Val Val Glu Thr His
            20                  25                  30

Ile Arg Tyr Leu Val Lys Tyr Leu Cys Lys Gly Ala Gly Ser Ser Gln
        35                  40                  45

Asp Ala Cys Ile Lys Phe Ile Gln Tyr Glu Val Asp Gly Ala Val Gly
    50                  55                  60

Tyr Leu Ile Gln His Asn Ala Thr Asp Ile Cys His Val Ile Arg Leu
65                  70                  75                  80

Cys
```

<210> SEQ ID NO 18
<211> LENGTH: 83
<212> TYPE: PRT
<213> ORGANISM: Homo sapiens

<400> SEQUENCE: 18

```
Gly Arg Asp Tyr Arg Thr Cys Leu Thr Ile Val Gln Lys Leu Lys Lys
1               5                   10                  15

Met Val Asp Lys Pro Thr Gln Thr Ser Val Ser Asn Ala Ala Thr Arg
            20                  25                  30

Val Cys Arg Thr Gly Arg Ser Arg Trp Arg Asp Val Cys Arg Asn Phe
        35                  40                  45

Met Arg Arg Tyr Gln Ser Arg Val Ile Gln Gly Leu Val Ala Gly Glu
    50                  55                  60

Thr Ala Gln Gln Ile Cys Glu Asp Leu Arg Leu Cys Ile Pro Ser Thr
65                  70                  75                  80

Gly Pro Leu
```

<210> SEQ ID NO 19
<211> LENGTH: 83
<212> TYPE: PRT
<213> ORGANISM: Naegleria fowleri

<400> SEQUENCE: 19

-continued

```
Ser Gly Ile Cys Asn Met Cys Gln Leu Leu Val Thr Gln Val Glu Asn
1               5                   10                  15

Trp Val Glu Ser Asn Asp Thr Ile Met Thr Leu Glu Lys Lys Leu Glu
            20                  25                  30

Gln Val Cys Ser Val Ile Pro Gly Gln Tyr Ser Ala Leu Cys Thr Tyr
        35                  40                  45

Ala Val Glu Gln Tyr Leu Pro Ile Phe Ile His Gln Val Glu Lys Gln
    50                  55                  60

Phe Pro Ala Leu Thr Ile Cys Gln Asp Val His Leu Cys Ser Ser Ala
65                  70                  75                  80

Gln Ala Ala

<210> SEQ ID NO 20
<211> LENGTH: 73
<212> TYPE: PRT
<213> ORGANISM: Clonorchis sinensis

<400> SEQUENCE: 20

Cys Lys His Cys Lys Thr Leu Val Gly Arg Ile Gln Asp Cys Trp Gln
1               5                   10                  15

Lys Gly Arg Ala Lys Ser Phe Val Glu Lys Thr Leu Ile Phe Leu Cys
            20                  25                  30

Lys Leu Thr Gly His Ser Glu Glu Gln Cys Thr Glu His Ala Glu Glu
        35                  40                  45

Phe Met Lys His Leu Asp Asp Trp Ile Thr Gly Lys Thr Pro Glu Glu
    50                  55                  60

Leu Cys Arg Ser Leu His Met Cys Lys
65                  70

<210> SEQ ID NO 21
<211> LENGTH: 83
<212> TYPE: PRT
<213> ORGANISM: Naegleria fowleri

<400> SEQUENCE: 21

Pro Ser Glu Phe Cys Asp Val Cys Lys Tyr Ala Val Gln Gln Val Asp
1               5                   10                  15

Gln Leu Ala Leu Gln Asn Glu Ala Ala Ile Gln Asn Ala Leu Leu Ala
            20                  25                  30

Ala Cys Gln Gln Leu Gly Asp Asn Gln Phe Gly Lys Ile Cys Asn Thr
        35                  40                  45

Val Val Leu Val Tyr Gly Asn Glu Leu Val Asn Ala Leu Val Thr Tyr
    50                  55                  60

Glu Asn Pro Thr Arg Val Cys Ser Glu Gln Leu Pro Leu Cys Pro Lys
65                  70                  75                  80

Asn Asn Thr

<210> SEQ ID NO 22
<211> LENGTH: 88
<212> TYPE: PRT
<213> ORGANISM: Caenorhabditis elegans

<400> SEQUENCE: 22

Asn Pro Ala Asn Pro Leu Asn Leu Lys Lys His His Gly Val Phe Cys
1               5                   10                  15

Asp Val Cys Lys Ala Leu Val Glu Gly Gly Glu Lys Val Gly Asp Asp
            20                  25                  30
```

```
Asp Leu Asp Ala Trp Leu Asp Val Asn Ile Gly Thr Leu Cys Trp Thr
            35                  40                  45

Met Leu Leu Pro Leu His His Glu Cys Glu Glu Leu Lys Lys Val
    50                  55                  60

Lys Lys Glu Leu Lys Lys Asp Ile Glu Asn Lys Asp Ser Pro Asp Lys
65                  70                  75                  80

Ala Cys Lys Asp Val Asp Leu Cys
                85

<210> SEQ ID NO 23
<211> LENGTH: 83
<212> TYPE: PRT
<213> ORGANISM: Homo sapiens

<400> SEQUENCE: 23

Ser Leu Pro Cys Asp Ile Cys Lys Asp Val Thr Ala Ala Gly Asp
1               5                   10                  15

Met Leu Lys Asp Asn Ala Thr Glu Glu Ile Leu Val Tyr Leu Glu
                20                  25                  30

Lys Thr Cys Asp Trp Leu Pro Lys Pro Asn Met Ser Ala Ser Cys Lys
            35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser Leu Gln

<210> SEQ ID NO 24
<211> LENGTH: 83
<212> TYPE: PRT
<213> ORGANISM: Bos taurus

<400> SEQUENCE: 24

Ser Leu Pro Cys Asp Ile Cys Lys Asp Val Ile Thr Ala Ala Gly Asn
1               5                   10                  15

Leu Leu Lys Asp Asn Ala Thr Glu Gln Glu Ile Leu Met Tyr Leu Glu
                20                  25                  30

Arg Thr Cys Asp Trp Leu Pro Lys Pro Asn Met Ser Ala Ser Cys Lys
            35                  40                  45

Glu Ile Val Asp Ser Tyr Leu Pro Val Ile Leu Asp Met Ile Lys Gly
    50                  55                  60

Gln Met Ser His Pro Gly Glu Val Cys Ser Ala Leu Asn Leu Cys Glu
65                  70                  75                  80

Ser Leu Gln

<210> SEQ ID NO 25
<211> LENGTH: 83
<212> TYPE: PRT
<213> ORGANISM: Mus musculus

<400> SEQUENCE: 25

Ser Leu Pro Cys Asp Ile Cys Lys Thr Val Val Thr Glu Ala Gly Asn
1               5                   10                  15

Leu Leu Lys Asp Asn Ala Thr Gln Glu Glu Ile Leu His Tyr Leu Glu
                20                  25                  30

Lys Thr Cys Glu Trp Ile His Asp Ser Ser Leu Ser Ala Ser Cys Lys
            35                  40                  45
```

```
Glu Val Val Asp Ser Tyr Leu Pro Val Ile Leu Asp Met Ile Lys Gly
            50                  55                  60

Glu Met Ser Asn Pro Gly Glu Val Cys Ser Ala Leu Asn Leu Cys Gln
65                  70                  75                  80

Ser Leu Gln

<210> SEQ ID NO 26
<211> LENGTH: 83
<212> TYPE: PRT
<213> ORGANISM: Gallus gallus

<400> SEQUENCE: 26

Ser Ile Pro Cys Asp Leu Cys Lys Glu Leu Thr Val Val Gly Lys
1               5                   10                  15

Val Leu Lys Asp Asn Gly Thr Glu Asp Glu Ile Arg Ser Tyr Leu Glu
            20                  25                  30

Lys Thr Cys Glu Phe Leu Pro Asp Gln Gly Leu Ala Ser Glu Cys Lys
            35                  40                  45

Glu Ile Val Asp Ser Tyr Leu Pro Val Ile Met Asp Met Ile Lys Glu
            50                  55                  60

Glu Phe Asp Lys Pro Glu Val Val Cys Ser Ala Leu Ser Leu Cys Gln
65                  70                  75                  80

Ser Leu Gln

<210> SEQ ID NO 27
<211> LENGTH: 83
<212> TYPE: PRT
<213> ORGANISM: Danio rerio

<400> SEQUENCE: 27

Thr Val Pro Cys Asp Leu Cys Lys Glu Val Leu Val Val Glu Gln
1               5                   10                  15

Leu Leu Lys Asp Asn Val Thr Glu Ser Glu Leu Leu Gly Tyr Leu Glu
            20                  25                  30

Lys Ala Cys Gln Leu Ile Pro Asp Glu Gly Leu Ala Asn Gln Cys Lys
            35                  40                  45

Glu Ile Val Asp Asn Tyr Phe Pro Val Leu Met Gly Ile Gln Gly
            50                  55                  60

Glu Leu Asp Asp Pro Gly Val Val Cys Gly Ala Leu Gly Leu Cys Val
65                  70                  75                  80

Ser Gln Gln

<210> SEQ ID NO 28
<211> LENGTH: 83
<212> TYPE: PRT
<213> ORGANISM: Xenopus laevis

<400> SEQUENCE: 28

Ser Met Pro Cys Asp Phe Cys Lys Glu Val Val Thr Val Leu Gly Asn
1               5                   10                  15

Tyr Leu Lys Asp Asn Ile Thr Gln Asp Glu Ile Lys Gln Tyr Leu Asn
            20                  25                  30

Lys Val Cys Asp Phe Ile Pro Asp Pro Gly Leu Ala Ser Thr Cys Lys
            35                  40                  45

Gln Glu Val Ser Asp Tyr Phe Thr Ile Val Leu Asn Leu Leu Glu Gln
            50                  55                  60
```

```
Glu Leu Ser Asn Pro Gly Val Leu Cys Ser Ser Leu Gly Leu Cys Thr
 65                  70                  75                  80

Ser Leu Gln
```

<210> SEQ ID NO 29
<211> LENGTH: 80
<212> TYPE: PRT
<213> ORGANISM: Homo sapiens

<400> SEQUENCE: 29

```
Asp Val Tyr Cys Glu Val Cys Glu Phe Leu Val Lys Glu Val Thr Lys
  1               5                  10                  15

Leu Ile Asp Asn Asn Lys Thr Glu Lys Glu Ile Leu Asp Ala Phe Asp
                 20                  25                  30

Lys Met Cys Ser Lys Leu Pro Lys Ser Leu Ser Glu Glu Cys Gln Glu
             35                  40                  45

Val Val Asp Thr Tyr Gly Ser Ser Ile Leu Ser Ile Leu Leu Glu Glu
         50                  55                  60

Val Ser Pro Glu Leu Val Cys Ser Met Leu His Leu Cys Ser Gly Thr
 65                  70                  75                  80
```

<210> SEQ ID NO 30
<211> LENGTH: 79
<212> TYPE: PRT
<213> ORGANISM: Bos taurus

<400> SEQUENCE: 30

```
Asp Ile Tyr Cys Glu Val Cys Glu Phe Val Val Lys Glu Val Ala Lys
  1               5                  10                  15

Leu Ile Asp Asn Asn Arg Thr Glu Glu Glu Ile Leu His Ala Leu Asp
                 20                  25                  30

Lys Val Cys Ser Lys Leu Pro Thr Ser Leu Ala Glu Gln Cys Gln Glu
             35                  40                  45

Val Val Asp Thr Tyr Gly Arg Ser Ile Leu Ser Ile Leu Leu Asp Glu
         50                  55                  60

Ala Ser Pro Glu Leu Val Cys Ser Met Leu His Leu Cys Ser Ser
 65                  70                  75
```

<210> SEQ ID NO 31
<211> LENGTH: 79
<212> TYPE: PRT
<213> ORGANISM: Mus musculus

<400> SEQUENCE: 31

```
Val Ile Leu Cys Gln Thr Cys Gln Phe Val Met Asn Lys Phe Ser Glu
  1               5                  10                  15

Leu Ile Val Asn Asn Ala Thr Glu Glu Leu Leu Val Lys Gly Leu Ser
                 20                  25                  30

Asn Ala Cys Gly Val Leu Pro Asp Pro Ala Arg Thr Lys Cys Gln Glu
             35                  40                  45

Val Val Gly Thr Phe Gly Pro Ser Leu Leu Asp Ile Phe Ile His Glu
         50                  55                  60

Val Asn Pro Ser Ser Leu Cys Gly Val Ile Gly Leu Cys Ala Ala
 65                  70                  75
```

<210> SEQ ID NO 32
<211> LENGTH: 80
<212> TYPE: PRT
<213> ORGANISM: Gallus gallus

<400> SEQUENCE: 32

Phe Ser Val Cys Glu Ile Cys Glu Thr Met Val Lys Glu Val Thr Gly
1               5                   10                  15

Leu Leu Glu Ser Asn Lys Thr Glu Glu Ile Val His Glu Met Glu
            20                  25                  30

Val Val Cys Tyr Leu Leu Pro Ala Ser Val Lys Asp Gln Cys Lys Asp
        35                  40                  45

Phe Ile Glu Val Tyr Gly Gln Ala Leu Ile Asp Met Leu Leu Glu Ala
    50                  55                  60

Thr Asn Pro Glu Ala Val Cys Val Met Leu Lys Cys Ala Ala Asn
65                  70                  75                  80

<210> SEQ ID NO 33
<211> LENGTH: 79
<212> TYPE: PRT
<213> ORGANISM: Xenopus laevis

<400> SEQUENCE: 33

Asn Val Leu Cys Glu Val Cys Glu Leu Met Val Ser Gln Leu Glu Lys
1               5                   10                  15

Leu Leu Asp Asn Asn Arg Thr Arg Glu Asn Ile Lys His Gly Leu Glu
            20                  25                  30

Lys Val Cys Lys Leu Leu Pro Ser Gln Tyr Thr Gln Lys Cys Glu Asp
        35                  40                  45

Met Ile Glu Glu Tyr Ser Asp Ala Leu Ile Glu Leu Leu Gln Glu
    50                  55                  60

Ala Asn Pro Gln Ala Ile Cys Thr Ala Leu Gly Tyr Cys Ser Gly
65                  70                  75

<210> SEQ ID NO 34
<211> LENGTH: 79
<212> TYPE: PRT
<213> ORGANISM: Danio rerio

<400> SEQUENCE: 34

Ser Pro Gln Cys Ala Ile Cys Glu Tyr Val Lys Glu Ile Glu Asn
1               5                   10                  15

Met Ile Gln Asp Gln Thr Ser Glu Ala Glu Ile Val Gln Ala Val Glu
            20                  25                  30

Lys Val Cys Asn Ile Leu Pro Ser Thr Leu Thr Ala Gln Cys Lys Asp
        35                  40                  45

Leu Ile Glu Thr Tyr Gly Gln Ala Ile Ile Asp Leu Leu Val Gln Glu
    50                  55                  60

Ala Asp Pro Lys Thr Val Cys Ser Phe Leu Ala Leu Cys Ser Gly
65                  70                  75

<210> SEQ ID NO 35
<211> LENGTH: 81
<212> TYPE: PRT
<213> ORGANISM: Homo sapiens

<400> SEQUENCE: 35

Gly Gly Phe Cys Glu Val Cys Lys Lys Leu Val Gly Tyr Leu Asp Arg
1               5                   10                  15

Asn Leu Glu Lys Asn Ser Thr Lys Gln Glu Ile Leu Ala Ala Leu Glu
            20                  25                  30

Lys Gly Cys Ser Phe Leu Pro Asp Pro Tyr Gln Lys Gln Cys Asp Gln

```
                35                  40                  45

Phe Val Ala Glu Tyr Glu Pro Val Leu Ile Glu Ile Leu Val Glu Val
 50                  55                  60

Met Asp Pro Ser Phe Val Cys Leu Lys Ile Gly Ala Cys Pro Ser Ala
 65                  70                  75                  80

His

<210> SEQ ID NO 36
<211> LENGTH: 81
<212> TYPE: PRT
<213> ORGANISM: Bos taurus

<400> SEQUENCE: 36

Gly Gly Phe Cys Glu Val Cys Lys Lys Leu Val Gly Tyr Leu Asp Arg
 1               5                  10                  15

Asn Leu Glu Lys Asn Ser Thr Lys Glu Gln Ile Leu Ala Ala Leu Glu
                20                  25                  30

Lys Gly Cys Ser Phe Leu Pro Asp Gln Tyr Arg Lys Gln Cys Asp Gln
                35                  40                  45

Phe Val Thr Glu Tyr Glu Pro Val Leu Ile Glu Ile Leu Val Glu Val
 50                  55                  60

Met Asp Pro Ser Phe Val Cys Leu Lys Ile Gly Ala Cys Pro Ala Ala
 65                  70                  75                  80

His

<210> SEQ ID NO 37
<211> LENGTH: 81
<212> TYPE: PRT
<213> ORGANISM: Mus musculus

<400> SEQUENCE: 37

Gly Gly Phe Cys Glu Val Cys Lys Lys Leu Val Leu Tyr Leu Glu His
 1               5                  10                  15

Asn Leu Glu Lys Asn Ser Thr Lys Glu Glu Ile Leu Ala Ala Leu Glu
                20                  25                  30

Lys Gly Cys Ser Phe Leu Pro Asp Pro Tyr Gln Lys Gln Cys Asp Asp
                35                  40                  45

Phe Val Ala Glu Tyr Glu Pro Leu Leu Leu Glu Ile Leu Val Glu Val
 50                  55                  60

Met Asp Pro Gly Phe Val Cys Ser Lys Ile Gly Val Cys Pro Ser Ala
 65                  70                  75                  80

Tyr

<210> SEQ ID NO 38
<211> LENGTH: 81
<212> TYPE: PRT
<213> ORGANISM: Gallus gallus

<400> SEQUENCE: 38

Gly Gly Phe Cys Asp Ile Cys Lys Met Ile Val Ala Tyr Ala Asp Lys
 1               5                  10                  15

Glu Leu Glu Lys Asn Ala Thr Thr Glu Ile Glu Ala Leu Leu Glu
                20                  25                  30

Lys Val Cys His Phe Leu Pro Glu Ser Val Ser Asp Gln Cys Val Gln
                35                  40                  45

Phe Val Glu Gln Tyr Glu Pro Val Val Val Gln Leu Leu Ala Glu Met
 50                  55                  60
```

```
Met Asp Pro Thr Phe Val Cys Thr Lys Leu Gly Val Cys Gly Ala Ala
 65                  70                  75                  80

Lys

<210> SEQ ID NO 39
<211> LENGTH: 81
<212> TYPE: PRT
<213> ORGANISM: Danio rerio

<400> SEQUENCE: 39

Gly Gly Phe Cys Asp Val Cys Lys Met Ala Val Arg Tyr Val Asp Gly
 1               5                  10                  15

Ile Leu Glu Gln Asn Ala Thr Gln Ser Glu Ile Glu Glu Ala Val Leu
            20                  25                  30

Lys Val Cys Ser Phe Leu Pro Asp Ala Val Lys Asp Glu Cys Asn Gln
        35                  40                  45

Leu Ile Glu Gln Tyr Glu Pro Leu Leu Val Gln Leu Leu Leu Gln Thr
    50                  55                  60

Leu Asp Pro Asp Phe Val Cys Met Lys Leu Gly Ala Cys Pro Glu Ala
 65                  70                  75                  80

Val

<210> SEQ ID NO 40
<211> LENGTH: 81
<212> TYPE: PRT
<213> ORGANISM: Xenopus laevis

<400> SEQUENCE: 40

Gly Asp Tyr Cys Ala Val Cys Lys Met Leu Met Arg Tyr Val Asp Glu
 1               5                  10                  15

Leu Leu Glu Lys Asn Ala Thr Glu Ile Arg Ile Lys Ala Phe Leu Gly
            20                  25                  30

Arg Ile Cys Asn Phe Leu Pro Asp Ser Met Gln Asn Glu Cys Ser Ala
        35                  40                  45

Leu Val Asn Glu Tyr Glu Pro Leu Phe Ile Gln Leu Leu Leu Glu Ala
    50                  55                  60

Leu Asp Pro Ser Phe Ile Cys Ile Lys Val Asn Leu Cys Gln Asn Lys
 65                  70                  75                  80

Lys

<210> SEQ ID NO 41
<211> LENGTH: 79
<212> TYPE: PRT
<213> ORGANISM: Homo sapiens

<400> SEQUENCE: 41

Gly Asp Val Cys Gln Asp Cys Ile Gln Met Val Thr Asp Ile Gln Thr
 1               5                  10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
        35                  40                  45

Asn Tyr Ile Ser Gln Tyr Ser Glu Ile Ala Ile Gln Met Met Met His
    50                  55                  60

Met Gln Pro Lys Glu Ile Cys Ala Leu Val Gly Phe Cys Asp Glu
 65                  70                  75
```

<210> SEQ ID NO 42
<211> LENGTH: 79
<212> TYPE: PRT
<213> ORGANISM: Bos taurus

<400> SEQUENCE: 42

Gly Asn Val Cys Gln Asp Cys Ile Gln Leu Val Thr Asp Val Gln Glu
1               5                   10                  15

Ala Leu Arg Thr Asn Ser Thr Phe Val Glu Ala Leu Val Asp His Ala
            20                  25                  30

Lys Glu Glu Cys Asp Arg Leu Gly Pro Gly Met Ser Asp Met Cys Lys
        35                  40                  45

Asn Tyr Ile Asn Gln Tyr Ser Glu Val Ala Ile Gln Met Val Met His
    50                  55                  60

Met Gln Pro Lys Glu Ile Cys Val Leu Ala Gly Phe Cys Asp Glu
65                  70                  75

<210> SEQ ID NO 43
<211> LENGTH: 83
<212> TYPE: PRT
<213> ORGANISM: Gallus gallus

<400> SEQUENCE: 43

Glu Asp Val Cys Gln Asp Cys Ile Arg Leu Val Thr Asp Val Gln Glu
1               5                   10                  15

Ala Val Arg Thr Asn Ala Thr Phe Val Lys Ser Leu Val Ala His Ala
            20                  25                  30

Lys Glu Glu Cys Asp Arg Leu Gly Pro Gly Met Ser Asp Met Cys Lys
        35                  40                  45

Ser Tyr Ile Ser Glu Tyr Ser Asp Leu Ala Ile Gln Met Met Met His
    50                  55                  60

Met Lys Asp Gln Gln Pro Lys Asp Ile Cys Ala Met Val Gly Phe Cys
65                  70                  75                  80

Pro Ser Val

<210> SEQ ID NO 44
<211> LENGTH: 83
<212> TYPE: PRT
<213> ORGANISM: Mus musculus

<400> SEQUENCE: 44

Glu Asp Val Cys Gln Asp Cys Met Lys Leu Val Ser Asp Val Gln Thr
1               5                   10                  15

Ala Val Lys Thr Asn Ser Ser Phe Ile Gln Gly Phe Val Asp His Val
            20                  25                  30

Lys Glu Asp Cys Asp Arg Leu Gly Pro Gly Val Ser Asp Ile Cys Lys
        35                  40                  45

Asn Tyr Val Asp Gln Tyr Ser Glu Val Cys Val Gln Met Leu Met His
    50                  55                  60

Met Gln Asp Gln Gln Pro Lys Glu Ile Cys Val Leu Ala Gly Phe Cys
65                  70                  75                  80

Asn Glu Val

<210> SEQ ID NO 45
<211> LENGTH: 79
<212> TYPE: PRT
<213> ORGANISM: Danio rerio

-continued

<400> SEQUENCE: 45

Gly Asp Val Cys Gln Asp Cys Val Thr Phe Ile Ser Asp Thr Gln Asp
1               5                   10                  15

Glu Ala Arg Val Asn Ser Ser Phe Ile Asn Thr Leu Ile Ala Gln Val
            20                  25                  30

Glu Asn Gln Cys Glu Leu Leu Gly Pro Gly Met Ser Asp Met Cys Lys
        35                  40                  45

Glu Tyr Ile Ser Gln Tyr Gly Pro Leu Val Phe Gln Gln Leu Met Ser
    50                  55                  60

Met Gln Pro Lys Asp Ile Cys Ala Arg Ala Gly Phe Cys Pro Thr
65                  70                  75

<210> SEQ ID NO 46
<211> LENGTH: 79
<212> TYPE: PRT
<213> ORGANISM: Xenopus laevis

<400> SEQUENCE: 46

Gly Asp Ile Cys Asn Asp Cys Thr Lys Leu Val Ser Asp Val Gln Asp
1               5                   10                  15

Ala Leu Arg Ser Asn Ser Ser Phe Ser Lys Lys Leu Val Asp His Phe
            20                  25                  30

Leu Gln Glu Cys Asn Leu Leu Asp Pro Ala Ile Ala Glu Met Cys Lys
        35                  40                  45

Ser Tyr Ile Asn Gln Tyr Ser Asp Ile Ala Ile Gln Val Leu Leu Gln
    50                  55                  60

Met Gln Pro Lys Gln Leu Cys Gly Met Ala Gly Phe Cys Asp Gln
65                  70                  75

<210> SEQ ID NO 47
<211> LENGTH: 19
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: helix a1 of human saposin A

<400> SEQUENCE: 47

Ser Leu Pro Cys Asp Ile Cys Lys Asp Val Val Thr Ala Ala Gly Asp
1               5                   10                  15

Met Leu Lys

<210> SEQ ID NO 48
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: helix a2 of human saposin A

<400> SEQUENCE: 48

Ala Thr Glu Glu Glu Ile Leu Val Tyr Leu Glu Lys Thr Cys Asp Trp
1               5                   10                  15

Leu

<210> SEQ ID NO 49
<211> LENGTH: 27
<212> TYPE: PRT
<213> ORGANISM: Homo sapiens

```
<220> FEATURE:
<221> NAME/KEY: MISC_FEATURE
<222> LOCATION: (1)..(27)
<223> OTHER INFORMATION: helix a3 of human saposin A

<400> SEQUENCE: 49

Pro Asn Met Ser Ala Ser Cys Lys Glu Ile Val Asp Ser Tyr Leu Pro
1               5                   10                  15

Val Ile Leu Asp Ile Ile Lys Gly Glu Met Ser
            20                  25

<210> SEQ ID NO 50
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: helix a4 of human saposin A

<400> SEQUENCE: 50

Pro Gly Glu Val Cys Ser Ala Leu
1               5
```

PRODUCTION OF SALIPRO PARTICLES

CROSS-REFERENCE TO RELATED APPLICATIONS

This application is a 35 USC § 371 National Stage filing of International Patent Application No. PCT/EP2020/060594, filed Apr. 15, 2020, which claims priority to European Patent Application No. 19169321.7, filed Apr. 15, 2019, the entire contents of which is hereby incorporated herein by reference.

SEQUENCE LISTING

The instant application contains a Sequence Listing, which is submitted herewith in electronically computer readable ASCII format via EFS-Web, and is hereby incorporated by reference in its entirety as required by 37 CFR §§ 1.821(e). The Sequence Listing file was filed on Nov. 6, 2024, and is named "223265-500431v2.txt" created using an MS-DOS compatible computer, and is 37.3 KB in size.

TECHNICAL FIELD OF THE INVENTION

The invention relates to a process for preparing saposin lipoprotein particles, comprising saposin-like protein, lipids and optionally a hydrophobic agent.

BACKGROUND OF THE INVENTION

Membranes surround, all living cells and form the envelopes of many viruses (e.g., HIV). In living cells, the cell membrane serves as semi-permeable barrier to preserve the contents of the cell. The membrane constituents, in particular membrane proteins such as receptors and transporters, also determine and regulate how the cell interacts with its environment. The latter function, which includes biological processes such as signal transduction, transport of molecules, energy metabolism, formation of cell-cell contacts and cellular homeostasis, is critical and relies on membrane proteins. Membrane proteins are encoded by approximately 30% of all ORFs (Wallin and von Heijne, Protein Science 1998 April; 7 (4):1029-38) and thus represent roughly one quarter of a cell's proteins. Membrane proteins of viral envelopes also serve to mediate interactions with the environment such as the host's cell membranes allowing the viral capsid and the viral genome to enter and infect the host cells.

Membrane proteins are of great interest for research in the Life Sciences and in particular for drug discovery because of their above-mentioned critical functions. In fact, the majority of drugs, i.e. more than 60%, target membrane proteins (Overington et al., Nature Reviews Drug Discovery 5, 993-996 (December 2006). For research purposes and clinical drug development it is therefore crucial that membrane proteins, but also other hydrophobic agents (e.g., hydrophobic drugs), can be subjected to state-of-the-art technology platforms without impairing the functioning of the hydrophobic agent or of the technology. This presents a paradox as most membrane proteins and other hydrophobic agents require a hydrophobic environment (ideally embedded into a structure that mimics their natural membrane environment) to function properly. Most biochemical assays, often performed in state-of-the-art technology platforms, however, are based on aqueous systems, which these assays and platforms require to function properly. It is therefore an object of the present invention to provide improved and more efficient processes for formulating hydrophobic agents in order to make them soluble in aqueous systems, while at the same time preserving or mimicking the hydrophobic agent's natural membrane and lipid environment.

This would also allow to employ membrane proteins or other hydrophobic agents in high-throughput screening (HTS), which in its state-of-the-art setups also usually requires solubility in aqueous systems to function properly. Advances in molecular biology, computing, robotics and detector technologies have advanced HTS to become the "workhorse" of pharmaceutical, biotech and Life Sciences research. Through the rapid and parallel execution of biochemical tests, HTS has enabled the rapid identification of drugs, antibodies, molecular interactions and proteins that modulate a particular biomolecular pathway. The obtained results provide starting points and important cues for further drug design, and also for understanding the role of a particular biochemical process in a living system.

The urge to scale down HTS, combined with advances in microfluidics, has led to the ongoing development of biochemical lab-on-a-chip approaches in which analyses can be carried out even more rapidly and at lower cost in small-scale setups. It would present a great advance if one were able to routinely employ also membrane proteins and other hydrophobic agents in such HTS or lab-on-a-chip applications. For this it is often required to immobilize the test agent on a surface such as a chip. Accordingly, it is a further object of the present invention to provide improved and more efficient ways of immobilizing hydrophobic agents on supports, in particular by rendering them compatible with aqueous test systems, while at the same time preserving or mimicking the hydrophobic agent's natural membrane and lipid environment.

Many state-of-the-art setups for measuring biochemical interactions and reactions (e.g., the binding of a ligand to its corresponding receptor, the interaction of an antibody with its corresponding antigen or the turnover of a substrate by an enzyme) rely on biosensors and analytes that are attached to the surface of a solid support. A well-known optical biosensor system is based on Surface Plasmon Resonance (SPR). Membrane proteins play a central role in detecting various environmental stimuli, making them attractive for application as surface-attached analytes in biosensor systems. However, as also these biosensor systems are mostly based on aqueous environments, membrane proteins and other hydrophobic agents cannot be readily employed. It therefore is a further object of the present invention to provide improved and more efficient ways of immobilizing hydrophobic agents on supports, in particular by rendering them compatible with aqueous test systems, while at the same time preserving or mimicking the hydrophobic agent's natural membrane and lipid environment.

In summary, as outlined above, the hydrophobic nature of membrane proteins and other hydrophobic agents is inconvenient for biochemical applications and studies, which usually take place in aqueous solutions. The hydrophobic nature of membrane proteins and other hydrophobic agents is also inconvenient for their potential administrations as therapeutic or diagnostic agents as most biological systems, including human blood, present a hydrophilic, aqueous environment. Hydrophobic agents (such as membrane proteins or hydrophobic compounds) therefore pose two major challenges for Life Sciences research and the pharmaceutical industry: (i) rendering membrane proteins and other hydrophobic agents soluble in aqueous solutions for assay and testing purposes without impairing their function and (ii) administering such hydrophobic agents as therapeutic and diagnostic agents, again without impairing their desired and/or natural function.

The second challenge, i.e. the administration and delivery of hydrophobic agents (e.g., hydrophobic compounds and/or proteins) as therapeutic or diagnostic agents, is caused primarily by their limited aqueous solubility. In case of drugs, this causes them to be prone to aggregation, leading to locally highly concentrated drug particles that may cause high toxicity, unwanted immune responses and/or render the drug inactive (Allen and Cullis, SCIENCE, 303 (5665): 1818-1822, Mar. 19, 2004).

It is an object of the present invention to make hydrophobic agents such as membrane proteins or hydrophobic drugs more easily employable in state-of-the-art biochemical assaying technologies such as HTS, lab-on-a-chip and biosensor applications, but also to provide better manufacturing and formulation processes for administering such hydrophobic agents in therapeutic or diagnostic applications. To fulfill this object, efficient, cost- and resource-saving methods that incorporate hydrophobic agents into soluble particles, while at the same time preserving or mimicking the hydrophobic agent's natural membrane and lipid environment, are highly desired.

Membrane proteins are most frequently purified in detergents, which form micelles around the proteins. However, detergents are quite often detrimental to protein structure and activity. In addition, detergents may interfere with downstream analytical methods. It is therefore an object in the art to avoid the use of high concentrations of detergents in solubilizing hydrophobic agents. Prior art methods that address the challenge of rendering insoluble hydrophobic agents soluble in aqueous solutions involve amongst others nanodisc systems (Bayburt et al., Archives of biochemistry and biophysics, 450.2 (2006): 215-222 and Denisov et al., Journal of the American Chemical Society, 126.11 (2004): 3477-3487).

EP 1 596 828 B1 describes disc-shaped bioactive agent delivery particles comprising an apolipoprotein, which tightly surrounds a lipid bilayer in a double belt-like fashion. The interior of said particles is formed by the hydrophobic region of the lipid bilayer. This is in contrast to liposomes, which are closed spherical bilayer shells containing an aqueous interior. The disc-shaped bioactive agent delivery particles described in EP 1 596 828 B1 have a Stokes diameter of about 10 nm and are proposed for use as delivery vehicles for hydrophobic pharmaceutical drugs such as amphotericin B or camptothecin.

EP 1 345 959 B1 describes a similar type of nanoscale particle with a diameter of about 10 nm and a height of about 5.5 nm. The particles are disc-shaped and composed of (i) an artificial membrane scaffold protein, (ii) a phospholipid bilayer and (iii) at least one hydrophobic or partially hydrophobic membrane protein.

However, there are several drawbacks with this nanodisc technology in that, for example, a removal of detergent is required during assembly of the particles. Moreover, the size homogeneity provided by the tight double-belt like fit of the apolipoprotein-derived MSP seems to go at the expense of a fixed minimum particle size and a limitation as to the maximum diameters obtainable with the methods of the prior art.

Recently, novel nanoparticle technologies involving the conserved saposin-like protein (SAPLIP) family of lipid binding proteins have been developed (WO 2014/095576 A1, WO 2015/036549 A1 and WO 2018/033647 A1).

The SAPLIP-family is based on four saposin founding members. These are small (~80 amino acids) proteins, saposin A to D, that bind and/or interact with lipids and function as essential cofactors for several lysosomal enzymes in sphingolipid catabolism (cf. Bruhn, Biochem J. (2005) 389, 249-257 and references cited therein). Saposins have been described to prefer negatively charged lipids and low pH, exhibiting markedly increased activities at acidic pH, with a pH optimum at the intra-lysosomal pH of 4.75. Saposin A, B, C, and D are proteolytically hydrolyzed from a single large precursor protein, prosaposin. The complete amino acid sequences for saposins A, B, C and D have been reported as well as the genomic organization and cDNA sequence of prosaposin (O'Brien et al. (1988) Science 241, 1098-1101; Furst et al (1992) Biochim Biophys Acta 1126: 1-16).

Saposin C is capable of inducing membrane fusion of phospholipid-containing vesicles in an acidic environment (Archives of Biochemistry and Biophysics 2003 Jul. 1; 415(1): 43-53), a feature not exhibited by the other saposins. Qi et al. (2009) Clin Cancer Res 15(18): 5840-5851 report on saposin C-coupled dioleoylphosphatidylserine nanovesicles (SapC-DOPS) that contain an aqueous interior, have a mean diameter of about 190 nm and show tumor-targeting activity in vivo. In SapC-DOPS, saposin C or a peptide derived thereof acts as homing peptide for the liposome it is attached to. Saposin C then targets the liposome to cancer cells exposing phosphatidylserine on the outer leaflet of the cell membrane. The authors believe that a unique acidic microenvironment around cancer cells caused by extracellular leakage of lysosomal enzymes makes tumor tissue an optimal target for saposin C. According to Qi et al., SapC-DOPS liposomes are prepared by drying solvent-dissolved purified phospholipids under $N_2$ (g), dispersing the dry phospholipids in acidic buffer (pH 5) containing purified saposin C, diluting the mixture 50× in a physiologic aqueous solution and facilitating nanovesicle assembly by subsequent sonication.

Popovic et al., PNAS, Vol. 109, No. 8 (2012) 2908-2912 report on the structure of saposin A detergent discs. Saposin A exists in a soluble and a lipid/detergent-bound state. In the absence of lipid, saposin A adopts a closed monomeric apo conformation. By contrast, the saposin A detergent disc structure reported by Popovic et al. reveals two chains of saposin A in an open conformation encapsulating 40 internally bound detergent molecules organized in a highly ordered bilayer-like hydrophobic core.

Besides the crystallization of saposin A detergent discs, Popovic et al. also describe the preparation of soluble lipid-saposin A complexes at pH 4.75 by a method requiring multiple steps. First, a uniform fraction of large unilamellar liposome vesicles is prepared by drying chloroform-dissolved purified lipids under $N_2$ (g), dispersing the dry lipids by vortex mixing in acidic buffer (50 mM sodium acetate pH 4.8, 150 mM NaCl), submitting the suspension to 10 cycles of freezing and thawing, blending in a vortex mixer for 5 min and extruding the mixture through a 200 nm filter. Mixing the thus prepared large unilamellar artificial liposome-vesicles with purified saposin A in acidic buffer resulted in soluble lipid-saposin A particles. The particle showed a narrow size distribution around an average hydrodynamic (Stokes) radius of 3.2 nm and contained about 5:1 lipid molecules per saposin A chain. The exact size of the particles was only moderately affected by the lipid to protein molar ratio and the composition of the liposomes. The authors observed similar 3.2 nm particles regardless of whether or not anionic phospholipids, cholesterol, or glycosphingolipids were present in the liposomal mixtures. In all cases, a single peak was observed in the size range of a Stokes radius of 3.2 nm, indicating a relatively narrow distribution of species. Hence, the technology of this publication is limited to a pH value of 4.75, to the aforementioned size of the particles, and includes a laborious upstream liposome preparation step.

WO 2014/095576 A1 for the first time showed that it is possible to incorporate purified, detergent solubilized hydrophobic cargo molecules or purified, detergent solubilized membrane proteins into saposin lipoprotein particles using detergent-solubilized and purified lipids. The method described in WO 2014/095576 A1 allows for the self-assembly of saposin lipoprotein particles by contacting the saposin-like protein in a liquid environment with solubilized lipids and the hydrophobic agent in form of purified, detergent solubilized hydrophobic cargo molecule or a purified, detergent-solubilized membrane protein. The individual components are all present in free and soluble form and their self-assembly into saposin lipoprotein particles is based on the free, random motion of all involved particle components in the liquid environment.

WO 2015/036549 A1 expanded the method described in WO 2014/095576 A1 to the incorporation of solubilized antigen molecules (shown for viral membrane proteins) from well-defined and purified HIV-1 virus like particles (VLP). According to the Examples of WO 2015/036549 A1, the pre-purified VLPs are lysed, the HIV-1 membrane spike protein is solubilized with detergent and then the free spike protein is contacted with free saposin A protein in a liquid environment. In this way, the saposin-like protein provides a lipid mimicking environment such that the antigen molecule is assembled therein.

Also here, the individual components are all present in free and soluble form and their self-assembly into saposin lipoprotein particles is based on the free, random motion of all involved particle components in the liquid environment.

WO 2018/033647 A1 describes a process for preparing a library of saposin lipoprotein particles from cell or organelle membranes. Instead of having to employ solubilized, purified lipids and protein components, WO 2018/033647 A1 allows the direct use of crude cell or organelle membranes as starting material to assemble the saposin lipoprotein particles. In this way, a library comprising a heterogenic mixture of saposin lipoprotein particles with different membrane lipid and/or membrane protein composition is obtained. The saposin lipoprotein particle libraries obtained by the method of WO 2018/033647 A1 therefore present a snapshot of the microdomains and components of the actual membrane from which they were produced. The method of WO 2018/033647 A1 allows for the self-assembly of the saposin lipoprotein particles by providing crude membranes or crude membrane vesicles that are contacted with the saposin-like protein in a liquid environment. Also here, during the assembly process, the individual components are all present in free (i.e. non-support-bound) form and their self-assembly into saposin lipoprotein particles is based on the free, random motion of all involved particle components in the liquid environment.

Whereas WO 2014/095576 A1, WO 2015/036549 A1 and WO 2018/033647 A1 present a significant improvement by providing a new class of nanoparticles derived from saposin proteins, which have many advantages over the previous nanodisc technology, there still is a need for further improvements of the processes for preparing saposin lipoprotein particles.

For use of saposin lipoprotein particles in commercial applications, large quantities need to be provided at reduced production costs. Hence, there is a need for improved processes for assembling saposin lipoprotein particles in terms of efficiency, costs and use of resources.

In light of the above-explained increasing importance of technology platforms in pharmaceutical and Life Sciences research it is crucial that hydrophobic agents incorporated into soluble nanoparticles are employable in these platforms. This often requires, however, the immobilization of the nanoparticles to a support as in case of biosensor applications.

The prior art processes for preparing saposin lipoprotein particles can be further optimized for efficient, cost- and resource-saving production of nanoparticles. In particular, the prior art processes require and presuppose unrestricted mobility of the starting materials in the liquid environment during particle assembly. Furthermore, the prior art does not offer an easy possibility to recycle surplus particle components for usage in another particle assembly reaction.

It is an object of this invention to address one or more of these drawbacks.

SUMMARY OF THE INVENTION

The problem underlying the invention is seen most generally in the provision of an improved, cost- and resource-saving process to produce saposin lipoprotein particles.

The problem is solved by the process defined in claim 1. Advantageous embodiments are described in the dependent claims and further herein below.

The invention provides a process for producing a saposin lipoprotein particle, wherein the produced saposin lipoprotein particle comprises
  a saposin-like protein,
  lipids, and
  optionally, a hydrophobic agent, wherein the hydrophobic agent is different from the lipids and
  (I) wherein the process comprises the following steps:
    a) providing the lipids, and optionally the hydrophobic agent;
    b.1) contacting the saposin-like protein with a support that is capable of selectively binding the saposin-like protein to the support in a liquid environment;
    c.1) contacting the support-bound saposin-like protein with the lipids and, optionally, the hydrophobic agent, to allow for the self-assembly of the saposin lipoprotein particle on the support;
    d) optionally eluting the support-bound saposin lipoprotein particle; or
  (II) wherein alternatively the process comprises the following steps:
    a) providing the hydrophobic agent and the lipids;
    b.2) contacting the hydrophobic agent with a support that is capable of selectively binding the hydrophobic agent to the support;
    c.2) contacting the support-bound hydrophobic agent with the saposin-like protein to allow for the self-assembly of the saposin lipoprotein particle on the support;
    d) optionally eluting the support-bound saposin lipoprotein particle.

In the process according to the invention, either the hydrophobic agent or the saposin-like protein are selectively bound to a support and particle assembly occurs in this support-bound state by contacting the support-bound hydrophobic agent or the saposin-like protein with the remaining components of the saposin lipoprotein particle, which allows for the self-assembly of the saposin lipoprotein particles on the support. This is different from the processes of the prior art, which relied on assembly processes, in which the individual components are all present in free (i.e. non-support-bound) form and their self-assembly into saposin lipoprotein particles is based on the free, random motion of all involved particle components in the liquid environment.

The process according to the invention has the advantage that the saposin-like protein or the hydrophobic agent is selectively bound to a support, which directly yields support-bound saposin lipoprotein particles or from which the later assembled particles can be eluted. This limits the amount of formed Salipro particles to the amount of pre-bound particle components, i.e. either the amount of bound saposin-like protein or bound hydrophobic agent. Consequently, any material that remains unbound can be recycled. The recycling can concern the saposin-like protein or the hydrophobic agent which is not bound to the support in step b.2) and b.1), respectively. The recycling can, however, also concern surplus particle components, which were contacted with the support-bound material to allow for self-assembly of the Salipro particles in step c.1)/c.2), but did not incorporate into particles. Such recycling of the "unused" components allows for cost- and resource-saving particle assembly.

Direct assembly of saposin lipoprotein particles on a support is particularly advantageous if the particles anyhow need to be used in a support-bound state. This is the case for many chip-based analytical applications such as biosensor applications, in particular for optical biosensor applications such as Surface Plasmon Resonance. These are described in more detail herein below. In the past, free saposin lipoprotein particles had first to be prepared by the prior art processes and then required a second coupling step to immobilize them on the support. With the method of the invention, it is possible to perform the actual particle assembly on the support, which saves additional costs and process steps.

It was surprising that Salipro particles could be assembled also when one particle component, i.e., the saposin-like protein or the hydrophobic agent, is bound to a support. The binding of one of the particle components to the support limits its freedom to get into contact with other particle components in solution and also its freedom for spatial interactions with the particle components. Consequently, an impairment of particle assembly with regard to efficiency, ultimately also influencing the overall yield of obtained particles, was expected.

It has to be borne in mind that saposin lipoprotein particle assembly must be assumed to involve significant rearrangements in saposin protein structure and lipid organization (e.g., from random motion of free lipids to highly ordered nanomembrane bilayer structures). The saposin protein likely undergoes a conformational change when switching from the closed lipid-free form to the open lipid-bound state. Particle self-assembly is thought to involve a step in which the saposin-like protein captures and embraces the lipids and the hydrophobic agent that will be incorporated into the particle. Whereas it was known that this self-assembly occurs in solution, it was entirely unexpected to see that it worked equally well and fast when one of the principal particle components (i.e. the saposin protein or the hydrophobic agent) is immobilized on a solid support.

It was unexpected to discover that high quality support-bound Salipro particles can be obtained with the process according to the invention, which provides an easy, rapid and efficient way of producing support-bound Salipro particles that maintain a uniform quality and composition over time. The invention in principle provides a more efficient and "straightforward process for obtaining support-bound Salipro particles by intertwining assembly and coupling of the Salipro particles. In this way, hydrophobic agents can—in one continuous process—be solubilized into stable particles mimicking their natural membrane environment and at the same time be immobilized on a support for direct use in applications such as lab-on-a-chip or biosensor applications such as SPR.

The saposin lipoprotein particles obtained by the process of the invention are in principle the same as those known from the prior art, just that they are directly in support-bound form. The saposin lipoprotein particles are also referred to herein as "Salipro particle(s)". They are nanoparticles that comprise a saposin-like protein, a hydrophobic agent and lipids. These components and advantageous embodiments thereof will be further defined below. The saposin-like protein belongs to the well-known and conserved SAPLIP family of lipid interacting proteins or is a derivative or truncated form thereof.

Practical experiments of the inventors have revealed that the size of the Salipro particles self-adjusts to the nature of the incorporated hydrophobic agent and lipids, e.g., to the size of the incorporated membrane protein. Salipro particles are surprisingly flexible in size. Also in the process according to the invention, it has been observed that the Salipro particles adjust their size to the nature of the incorporated hydrophobic agents. This is advantageous over the size limitation of other non-saposin-derived prior art particles. This flexibility also enables the incorporation of very large hydrophobic agents, such as (multimeric) membrane proteins. For these in particular the process of the invention has the advantage that they can be reconstituted in their natural environment, e.g., the membrane lipids or other cell components associated with the membrane protein and potentially required for maintaining the protein's structure and/or function.

Surprisingly, Salipro particles display a certain degree of thermostability, and also seem to be amenable to freeze-drying and rehydration when bound to supports without major quality deterioration observable. This enables Salipro particles that are obtained by the process of the invention to be used in applications in which portability and storage stability is an issue. With the process of the invention it is possible to obtain support-bound Salipro particles that can be custom-made in advance, stored and shipped to end users later on. It is also possible to employ them in applications over a longer period of time, for example, lab-on-a-chip experiments that reuse the same chip multiple times.

The support-bound Salipro particles obtained with the method of the invention have proven to be capable of the incorporation of a variety of lipids, membrane proteins and hydrophobic compounds at a physiological pH, giving rise to nanoscale complexes that are soluble, but support-bound and stable in an aqueous environment. For the hydrophobic agents tested thus far, in particular for many complex membrane proteins, the incorporation into the support-bound Salipro particles has had no negative effect on their biological function. By contrast, for many of these, incorporation into Salipro particles efficiently mimics the hydrophobic agent's natural membrane environment and therefore has a positive effect on their biological function.

The invention also provides the advantage that hydrophobic agents, for which direct immobilization on supports without impairment or loss of their biological function is not possible, can be indirectly immobilized by incorporation into a Salipro particle prepared according to process (I) of the invention, i.e. in which the Salipro particle is bound to the support not via the hydrophobic agent but via a binding moiety in the saposin-like protein. This allows the hydrophobic agent to remain unmodified and/or not in direct contact with the support, while still being effectively bound to a support.

As described above, the provision of support-bound Salipro particles, which can be optionally also eluted from the support, is a very useful tool in chip-based applications such as lab-on-a-chip or biosensor (e.g., SPR) applications.

It appears that by selectively binding the hydrophobic agent or the saposin-like protein to a support and by contacting them with the respective other mandatory particle components, the process of the invention provides a robust technique to assemble Salipro particles, which are stable in aqueous solutions over a wide pH range, in particular at physiological pH, and allows larger particles than the 3.2 nm saposin A-derived lipoprotein particles obtained from synthetically prepared liposomes according to the prior art teaching of Popovic et al.

As described in the introduction, the importance of membrane proteins in therapeutic developments necessitates the discovery of innovative methods for interrogating membrane proteins in cell free mediums, preferably in a detergent-free environment.

The Salipro particles obtainable by the process of the invention fulfill this requirement. The Salipro particles, once obtained, are stable in cell free media and detergent-free environments, and are directly bound to supports that they may later on be used on.

In a particular advantageous embodiment of the invention, the hydrophobic agent and the lipids that are to be incorporated into the saposin lipoprotein particles are provided in form of biological membranes comprising the hydrophobic agent and the lipids that are to be incorporated into the saposin lipoprotein particles. In particular, viral, archaeal, eukaryotic or prokaryotic membranes can be directly employed in the process of the invention as source materials for the hydrophobic agent and the lipids. The biological membranes can be provided in the form of cells, viruses or organelles, all of which can be intact, treated with an amphiphilic agent, or lysed. The amphiphilic agent can be selected from the group consisting of detergents, amphiphilic peptides, amphiphilic polymers, other amphiphilic compounds and mixtures thereof. Examples of amphiphilic polymers that can be used according to the invention are maleic acid copolymers, in particular styrene-maleic acid copolymer (SMA) or diisobutylene-maleic acid copolymer (DIBMA). Amphiphilic peptides and amphiphilic polymers can be considered specialty detergents. Suitable SMAs are, e.g., described in Postis, Vincent, et al. "The use of SMALPs as a novel membrane protein scaffold for structure study by negative stain electron microscopy." Biochimica et Biophysica Acta (BBA)-Biomembranes 1848.2 (2015): 496-501. DIBMAs are commercially available, e.g. from anatrace as BMA101. Preferably, the amphiphilic agent is a detergent as defined herein. Preferably, the cells are eukaryotic cells, in particular non-human animal or human cells. Surprisingly the research leading up to this invention has shown that no purification of the biological membranes is required. Rather, when using the method of the invention, saposin lipoprotein particles can be prepared directly from intact, amphiphilic agent-treated, or lysed cells, viruses or organelles.

By using biological membranes as starting material in the process of the invention, hydrophobic agents can be incorporated into Salipro particles together with their native membrane environment. Compared to the process of WO 2018/033647 A1, process alternative (II) of the invention has the advantage that only the Salipro particles comprising the hydrophobic agent of interest are prepared, and not a full library of Salipro particles representing the entire membrane proteome/lipidome, from which the particles comprising the hydrophobic agent of interest again need to be isolated. In addition, the process of the invention has the advantage over WO 2018/033647 A1 that support-bound particles can be obtained in a straightforward, simplified and continuous "one-step process", which is cost-effective and desirable especially if the Salipro particles are to be used in support-bound form.

By using biological membranes as starting material in process alternative (I) of the invention, a library of Salipro particles can be obtained wherein the library comprises a heterogenic mixture of saposin lipoprotein particles with different membrane lipid and membrane protein compositions. Compared to the process of WO 2018/033647 A1, this embodiment of the process of the invention has the advantage that support-bound particles can be obtained in a continuous "one-step process", which is cost-effective and desirable especially if the library of Salipro particles is to be used in support-bound form.

The Salipro particles or the library of Salipro particles obtainable by the process of the invention can be for use in medicine, for use in a diagnostic method, a cosmetic treatment or for use as vaccination formulation. Further, the particles obtainable by the process of the invention can be used as a tool for diagnostics, drug development, drug screening, drug discovery, antibody development, development of therapeutic biologics, for membrane or membrane protein purification, for membrane protein expression, for membrane and/or membrane protein research, for the isolation, identification and/or study of membranes and/or membrane proteins or creation of a lipidome or membrane proteome database.

DETAILED DESCRIPTION OF THE INVENTION

The invention provides a process for producing a saposin lipoprotein particle, wherein the saposin
    lipoprotein particle comprises
      a saposin-like protein,
      lipids, and
      optionally, a hydrophobic agent, wherein the hydrophobic agent is different from the lipids and
(I) wherein the process comprises the following steps:
    a) providing the lipids, and optionally the hydrophobic agent;
    b.1) contacting the saposin-like protein with a support that is capable of selectively binding the saposin-like protein to the support in, a liquid environment;
    c.1) contacting the support-bound saposin-like protein with the lipids and, optionally, the hydrophobic agent, to allow for the self-assembly of the saposin lipoprotein particle on the support;
    d) optionally eluting the support-bound saposin lipoprotein particle; or
(II) wherein alternatively the process comprises the following steps:
    a) providing the hydrophobic agent and the lipids;

b.2) contacting the hydrophobic agent with a support that is capable of selectively binding the hydrophobic agent to the support;

c.2) contacting the support-bound hydrophobic agent with the saposin-like protein to allow for the self-assembly of the saposin lipoprotein particle on the support;

d) optionally eluting the support-bound saposin lipoprotein particle.

The process according to the invention in particular allows the provision of support-bound Salipro particles, wherein each Salipro particle comprises a saposin-like protein, lipids, and a hydrophobic agent. When a complex set of lipids and hydrophobic agents is provided in step a), for example, in form of a biological membrane, a library of Salipro particles is generated in process alternative (I) of the invention. This library will comprise Salipro particles comprising a saposin-like protein, a hydrophobic agent (e.g., a membrane protein) and lipids, but may also comprise Salipro particles only composed of lipids and the saposin-like protein.

The saposin lipoprotein particles are also referred to herein as "Salipro particle(s)". They comprise a saposin-like protein and lipids as mandatory components. Usually, a Salipro particle comprises one type of saposin-like protein. Typically, and also according to a preferred embodiment, the saposin lipoprotein particle prepared according to the invention comprises a saposin-like protein, lipids, and a hydrophobic agent Salipro particles of the invention may also comprise multiple hydrophobic agents, which may be the same or different from each other. Examples of multimers of the same hydrophobic agent in a Salipro particle are a multimeric membrane protein or a plurality of hydrophobic compounds. An example of different hydrophobic agents in a Salipro particle is a Salipro particle comprising a membrane protein and a hydrophobic compound.

Salipro particles of the invention comprise a plurality of lipids, which may be the same or different from each other.

The saposin-like protein used in the process of the invention is a saposin-like protein (SAPLIP) or a derivative or truncated form thereof. The term "saposin-like protein" (SAPLIP) is art-recognized and includes all members of the conserved saposin-like protein (SAPLIP) family of lipid interacting proteins. The abbreviation "SAPLIP" is used synonymously with the term "saposin-like protein". The SAPLIP family is characterized by the saposin-fold, a conserved alpha-helical three-dimensional structure that is stabilized by highly conserved intramolecular disulfide bonds (Munford et al. (1995), Journal of Lipid Research, vol. 36, no. 8, 1653-1663 and Bruhn (2005), Biochem J 389 (15): 249-257). Examples of members of the saposin-like protein (SAPLIP) family according to the invention are described in Munford et al. (1995), Journal of Lipid Research, vol. 36, no. 8, 1653-1663 and Bruhn (2005), Biochem J 389 (15): 249-257, both of which are hereby incorporated by reference in their entirety.

In the ligand-free (i.e. detergent-free/lipid-free), "closed" state, the SAPLIPs adopt a monomeric compact four-helix bundle-type structure, the saposin fold. This fold is exemplified by the structure of the closed apo form of human saposin A (Protein Data Bank (PDB) ID code: 2DOB, Ahn et al. (2006) Protein Sci. 15: 1849-1857) or the structures of saposin C (PDB ID code: 1M12; de Alba et al. (2003) Biochemistry 42, 14729-14740), NK-lysin (PDB ID code: 1NKL; Liepinsh et al. (1997) Nat. Struct. Biol. 4, 793-795), amoebapore A (PDB ID code: 1OF9) and granulysin (PDB ID code: 1L9L; Anderson et al. (2003) J. Mol. Biol. 325, 355-365), which are all nearly identical and easily superimposable.

SAPLIPs undergo a conformational change upon binding to ligands such as lipids or detergent molecules. In the ligand-bound "open" conformation, SAPLIPs adopt a V-shaped or boomerang-shaped conformation with exposed hydrophobic surfaces that contact the bound lipids. The open conformation is exemplified by the saposin A detergent disc structure of the prior art (PDB ID code: 4DDJ; Popovic et al., PNAS, Vol. 109, No. 8 (2012) 2908-2912) and the structure of saposin C bound to SDS detergent micelles (PDB ID code: 1SN6; Hawkins et al. (2005) J. Mol. Biol. 346: 1381-1392). In the Salipro particles, the saposin-like protein preferably is amphipathic, with one part of its structure more or less hydrophilic and facing the aqueous solvent and the other part more or less hydrophobic and facing the hydrophobic center of the particle, which comprises the lipids. The saposin-like protein is preferably characterized by amphipathic α-helices with more hydrophobic residues (such as A, C, F, G, I, L, M, V, W or Y) predominantly on one face of the helix and more polar or charged residues (such as D, E, N, Q, S, T, H, K, or R) on the other face of the helix.

The abbreviations for amino acid residues as used herein are as follows: A, Ala, alanine; V, Val, valine; L, Leu, leucine; I, lie, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine.

Contrary to the apolipoprotein-derived nanodiscs of the prior art, the saposin-like protein of the invention does not enclose the lipids in a double belt-like fashion but rather, the Salipro particles are held together by a core comprising the lipids which is surrounded by two or more approximately V-shaped or boomerang-shaped saposin-like proteins arranged in an orientation with substantially no direct protein-protein contacts between the individual saposin-like proteins within a given Salipro particle. Without wanting to be bound to this theory, it is believed that this arrangement of saposin-like proteins and lipids in the Salipro particles provides the size flexibility that is observed when bulky hydrophobic agents or increasing amounts of lipids are incorporated into the particles in the process of the invention.

Whereas the ability to interact with lipids as well as the above-described amphipathic nature and three-dimensional structure is highly conserved among SAPLIPs, they are highly diverse on the amino acid sequence level, with sequence identities below the usual threshold zone of 25-30% identity to define homology (cf. sequence comparison in FIGS. 4A and 4B of Bruhn (2005), Biochem J 389 (15): 249-257 reproduced in enclosed FIGS. 13A and 13B).

In the lipoprotein Salipro particles, the saposin-like protein serves primarily as a structural protein, providing the scaffold for the structure of the lipoprotein Salipro particles, for example, a disc-like structure. For this reason, structural features, in particular the saposin-fold that is characteristic of the SAPLIPs, are more important for defining the saposin-like protein of the invention as compared to mere sequence determinants.

Examples of SAPLIPs according to the invention are saposins A, B, C or D (for example from *Homo sapiens* [cf. SEQ ID NO. 1 to 4], *Equus caballus*, *Bos taurus*, *Mus musculus*, *Oryctolagus cuniculus*, *Rattus norvegicus* or

*Xenopus laevis*); Surfactant protein B (for example from *Homo sapiens, Canis familiaris, Mus musculus, Oryctolagus cuniculus, Ovis aries* or *Rattus norvegicus*); Granulysin (for example from *Homo sapiens*; cf. SEQ ID NO. 5); NK-lysin (for example from *Sus scrofa*; cf. SEQ ID NO. 6); NR-lysin orthologues (for example from *Equus caballus* or *Bos taurus*); Amoebapores (for example from Entamoeba histolytica); Amoebapore orthologues (for example from Entamoeba dispar or Entamoeba invadens); Amoebapore-like protein (for example from Fasciola hepatica); Naegleriapores (for example from Naegleria fowleri); Clornorin (for example from Clonorchis sinensis); Prosaposin (for example from *Homo sapiens, Equus caballus, Bos taurus, Mus musculus, Oryctolagus cuniculus, Rattus norvegicus* or *Xenopus laevis*) and MSAP (for example from *Homo sapiens*).

The sequences of specific SAPLIPs used according to the invention are given in FIGS. 4A and 4B of Bruhn (2005), Biochem J 389 (15): 249-257, reproduced in enclosed FIGS. 13A and 13B, and which sequences are hereby specifically incorporated by reference. The sequences of particular SAPLIPs used according to the invention are given in the sequence listing as follows:

A SAPLIP used according to the invention may also be a polypeptide comprising the saposin-fold as part of a multi-domain protein. This is for example the case in acid sphingomyelinase (from *Homo sapiens*, Caenorhabditis elegans, *Ciona intestinalis, Anopheles, Drosophila, Mus musculus* or *Rattus norvegicus*); GDSL (Gly-Asp-Ser-Leu) lipase such as acyloxy hydrolase (from *Homo sapiens* or *Rattus norvegicus*); Countin (from *Dictyostelium discoideum*); J3-crystallin (from *Tripedalia cystophora*) and Plant aspartic proteases (from Viridiplantae). A further SAPLIP used according to the invention can be bacteriocin AS-48. Bacteriocin AS-48 displays antimicrobial activity, is also able to bind lipids and possesses the same fold as the remaining SAPLIP family members but is devoid of any disulphide bridges.

Whereas, in the following, the invention is described in more detail for saposin A or a derivative or truncated from thereof as saposin-like protein, and whereas saposin A or a derivative or truncated from thereof is a preferred embodiment, the invention shall not be limited thereby. Rather, the invention explicitly extends to the entire family of saposin-like proteins (SAPLIPs) as saposin-like proteins of the invention. Due to the high degree of structural and func-

TABLE 1

| SEQ ID NO. | Source | Protein | Species | number of aa |
|---|---|---|---|---|
| 1 | Public Domain | Saposin A | *Homo sapiens* | 81 |
| 2 | Public Domain | Saposin B | *Homo sapiens* | 79 |
| 3 | Public Domain | Saposin C | *Homo sapiens* | 80 |
| 4 | Public Domain | Saposin D | *Homo sapiens* | 78 |
| 5 | Public Domain | Granulysin | *Homo sapiens* | 145 |
| 6 | Public Domain | NK-lysin | *Sus scrofa* | 129 |
| 7 | Bruhn, 2005, FIG. 4A | Amoebapore C | *Entamoeba histolytica* | 77 |
| 8 | Bruhn, 2005, FIG. 4A | Disparpore C | *Entamoeba dispar* | 75 |
| 9 | Bruhn, 2005, FIG. 4A | Amoebapore B | *Entamoeba histolytica* | 77 |
| 10 | Bruhn, 2005, FIG. 4A | Disparpore B | *Entamoeba dispar* | 75 |
| 11 | Bruhn, 2005, FIG. 4A | Amoebapore A | *Entamoeba histolytica* | 77 |
| 12 | Bruhn, 2005, FIG. 4A | Disparpore A | *Entamoeba dispar* | 75 |
| 13 | Bruhn, 2005, FIG. 4A | NK-Lysin 1 | *Sus scrofa* | 83 |
| 14 | Bruhn, 2005, FIG. 4A | NK-Lysin 2 | *Sus scrofa* | 78 |
| 15 | Bruhn, 2005, FIG. 4A | NK-1-like *E. caballus* | *Equus caballus* | 83 |
| 16 | Bruhn, 2005, FIG. 4A | Bolysin | *Bos taurus* | 84 |
| 17 | Bruhn, 2005, FIG. 4A | AP-like *F. hepatica* | *Fasciola hepatica* | 81 |
| 18 | Bruhn, 2005, FIG. 4A | Granulysin | *Homo sapiens* | 83 |
| 19 | Bruhn, 2005, FIG. 4A | Naegleriapore B2 | *Naegleria fowleri* | 83 |
| 20 | Bruhn, 2005, FIG. 4A | Clonorin | *Clonorchis sinensis* | 73 |
| 21 | Bruhn, 2005, FIG. 4A | Naegleriapore A1 | *Naegleria fowleri* | 83 |
| 22 | Bruhn, 2005, FIG. 4A | AP-like *C. elegans* | *Caenorhabditis elegans* | 88 |
| 23 | Bruhn, 2005, FIG. 4B | Saposin A | *Homo sapiens* | 83 |
| 24 | Bruhn, 2005, FIG. 4B | Saposin A | *Bos taurus* | 83 |
| 25 | Bruhn, 2005, FIG. 4B | Saposin A | *Mus musculus* | 83 |
| 26 | Bruhn, 2005, FIG. 4B | Saposin A | *Gallus gallus* | 83 |
| 27 | Bruhn, 2005, FIG. 4B | Saposin A | *Danio rerio* | 83 |
| 28 | Bruhn, 2005, FIG. 4B | Saposin A | *Xenopus laevis* | 83 |
| 29 | Bruhn, 2005, FIG. 4B | Saposin C | *Homo sapiens* | 80 |
| 30 | Bruhn, 2005, FIG. 4B | Saposin C | *Bos taurus* | 79 |
| 31 | Bruhn, 2005, FIG. 4B | Saposin C | *Mus musculus* | 79 |
| 32 | Bruhn, 2005, FIG. 4B | Saposin C | *Gallus gallus* | 80 |
| 33 | Bruhn, 2005, FIG. 4B | Saposin C | *Xenopus laevis* | 79 |
| 34 | Bruhn, 2005, FIG. 4B | Saposin C | *Danio rerio* | 79 |
| 35 | Bruhn, 2005, FIG. 4B | Saposin D | *Homo sapiens* | 81 |
| 36 | Bruhn, 2005, FIG. 4B | Saposin D | *Bos taurus* | 81 |
| 37 | Bruhn, 2005, FIG. 4B | Saposin D | *Mus musculus* | 81 |
| 38 | Bruhn, 2005, FIG. 4B | Saposin D | *Gallus gallus* | 81 |
| 39 | Bruhn, 2005, FIG. 4B | Saposin D | *Danio rerio* | 81 |
| 40 | Bruhn, 2005, FIG. 4B | Saposin D | *Xenopus laevis* | 81 |
| 41 | Bruhn, 2005, FIG. 4B | Saposin B | *Homo sapiens* | 79 |
| 42 | Bruhn, 2005, FIG. 4B | Saposin B | *Bos taurus* | 79 |
| 43 | Bruhn, 2005, FIG. 4B | Saposin B | *Gallus gallus* | 83 |
| 44 | Bruhn, 2005, FIG. 4B | Saposin B | *Mus musculus* | 83 |
| 45 | Bruhn, 2005, FIG. 4B | Saposin B | *Danio rerio* | 79 |
| 46 | Bruhn, 2005, FIG. 4B | Saposin B | *Xenopus laevis* | 79 | tional conservation among SAPLIPs, the features and advantages of certain embodiments with saposin A as saposin-like protein have been shown to also apply to other embodiments using other SAPLIPs or derivatives or truncated forms thereof as saposin-like protein.

According to a preferred embodiment, the SAPLIP is saposin A, saposin B, saposin C or saposin D. In one embodiment, the SAPLIP is saposin A, saposin B or saposin D. The saposin A, saposin B, saposin C or saposin D is preferably a saposin A, saposin B, saposin C or saposin D from *Homo sapiens, Equus caballus, Bos taurus, Mus musculus, Oryctolagus cuniculus, Rattus norvegicus* or *Xenopus laevis*. In one embodiment, the SAPLIP is of human origin (i.e. a *Homo sapiens* SAPLIP).

In a preferred embodiment, the SAPLIP is saposin A, preferably saposin A from *Homo sapiens, Equus caballus, Bos taurus, Mus musculus, Oryctolagus cuniculus, Rattus norvegicus* or *Xenopus laevis*, and particularly preferred human saposin A, the amino acid sequence of which is given as SEQ ID NO. 1. The expression, purification and crystallization of Saposin A as LDAO-detergent complex is for example, described in PNAS, Vol. 109, No. 8 (2012) 2908-2912 (Popovic et al.).

According to one embodiment, the saposin-like protein comprises the full length sequence of a SAPLIP. In another embodiment, the saposin-like protein is a derivative of a SAPLIP, in particular a polypeptide comprising an amino acid sequence with at least 20, 25, 30, 40, 50 or 60%, preferably at least 75% identity to the full length sequence of the respective SAPLIP. In particular, the saposin-like protein can comprise a sequence having an identity with the full length sequence of a SAPLIP of at least 80%, 85%, 90% or 95%.

A derivative or truncated form of a SAPLIP can be used in the process of the invention as long as it is able to self-assemble into Salipro particles in the process of the invention that is specified in the claims and in further detail herein. This can be easily tested by those skilled in the art according to the Examples described herein without undue burden.

In one embodiment, the saposin-like protein is saposin A, saposin B, saposin C, saposin D or a derivative or truncated form thereof, which is capable of forming saposin lipoprotein particles in the process of claim 1.

The term "sequence identity" as used herein refers to a degree of identity between proteins that can be calculated by optimal alignment of the sequences using a scoring matrix such as the Blosum62 matrix described in Henikoff S. and Henikoff J G., P. N. A. S. USA 1992, 89:10915-10919. Calculation of the percentage identity and optimal alignment of two sequences using the Blosum62 similarity matrix and the algorithm of Needleman and Wunsch (J. Mol. Biol. 1970, 48:443-453) can be performed using the GAP program of the Genetics Computer Group (GCG, Madison, WI, USA) using the default parameters of the program. As a comparison for amino acid alignments the EMBL-online tool "EMBOSS Stretcher" as found in the website: ebi.ac.uk/Tools/psa/emboss stretcher is used, using the programs default settings.

In another embodiment, the derivative of a SAPLIP is a polypeptide comprising a sequence having one or more amino acid deletions, additions, insertions and/or substitutions in the amino acid sequence of the respective SAPLIP. For example, the SAPLIP derivative can be a polypeptide comprising a sequence of a particular SAPLIP in which 1 to 40, preferably 1 to 30, and in particular 1 to 20 or 1 to 15 amino acids have been deleted, added, inserted and/or substituted.

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

In a preferred embodiment, the derivative or truncated form of the SAPLIP is selected from
  i. a protein having at least 20% sequence identity to the full length sequence of SEQ ID NO. 1, 2, 3, 4, 5 or 6; in particular a protein having at least 20% sequence identity to the full length sequence of SEQ ID NO. 1, 2, 3, 4, 5 or 6, wherein said protein is capable of self-assembling together with lipids into lipoprotein particles when employed in the process of claim 1; and
  ii. a protein comprising the sequence of SEQ ID NO. 1, 2, 3, 4, 5 or 6 in which 1 to 40 amino acids have been deleted, added, inserted and/or substituted.

The sequence identities described herein, for example, the embodiment in which the derivative of the saposin-like protein has at least 20% sequence identity to the full length sequence of SEQ ID NO. 1, 2, 3, 4, 5 or 6, can be combined with the feature that said protein is amphipathic, forms at least one alpha helix, and is capable of-self-assembling together with lipids into lipoprotein particles when employed in the process of claim 1.

According to a further embodiment, the saposin-like protein is a derivative of saposin A that comprises one or more fragments of SEQ NO. 1. Preferred fragments correspond to the helices a1, a2, a3 and a4 of saposin A, wherein helix a1 is formed by the following continuous stretch of amino acids: "SLPCDICKDVVTAAGDMLK" (SEQ ID NO: 47); helix a2 is formed by the following continuous stretch of amino acids: "ATEEEILVYLEKTCDWL" (SEQ ID NO: 48); helix a3 is formed by the following continuous stretch of amino acids: "PNMSASCKEIVDSYLPVILDIIKGEMS" (SEQ ID NO: 49); and helix a4 is formed by the following continuous stretch of amino acids: "PGEVCSAL" (SEQ ID NO: 50). According to a particular embodiment, the derivative of saposin A is a polypeptide comprising a sequence selected from helices a1, a2, a3, a4 of saposin A and combinations thereof, in particular wherein the polypeptide comprises the sequences of helices a1, a2 and a3 of saposin A The fragments of saposin such as its helices a1, a2, a3, a4, may have one or more amino acid deletions, additions, insertions and/or substitutions in the amino acid sequence.

According to another embodiment, the saposin-like protein is a derivative of a saposin-like protein comprising one or more of the fragments defined in relation to saposin A in the preceding paragraph, wherein the fragments are replaced by the corresponding sequences of the respective saposin-like protein.

According to one embodiment, when a derivative or truncated form of a SAPLIP is used as saposin-like protein according to the invention, said derivative or truncated form should be amphipathic, form at least one alpha helix. In addition or alternatively, said derivative or truncated form should be capable of self-assembling together with lipids into lipoprotein particles when employed in the process according to the invention. As used herein, the term "amphipathic" refers to polypeptides or molecules having both hydrophilic and hydrophobic regions.

Preferably, if a derivative of a SAPLIP is used, at least three, four, five or all of the six cysteine residues corresponding to the six cysteines in the SAPLIP founding member saposin A should be present. It is referred in this respect to the positions of the cysteines in the sequence comparison in FIGS. 4A and 4B of Bruhn (2005), Biochem J 389 (15): 249-257. The sequences and sequence alignments of FIGS. 4A and 4B of Bruhn et al. are reproduced in enclosed FIGS. 13A and 13B and hereby specifically incorporated by reference.

The SAPLIP according to the invention may also include one or more non-natural amino acids, amino acid analogs, or a peptidomimetic structure, in which the peptide bond is replaced by a structure more resistant to metabolic degradation.

Step a) of the Process of the Invention

In step a) of the process of the invention the lipids, and optionally the hydrophobic agent, that are to be incorporated into the Salipro particle are provided. Importantly, further lipids and/or hydrophobic agents may also be provided in other steps of the process.

"A" and "the" are generally used herein in the sense of "at least one" or "at least one type". For example, at least one hydrophobic agent is comprised in the Salipro particles of the invention and correspondingly provided in step a).

The hydrophobic agent and/or the lipids may be provided in a composition with other constituents. Preferably the hydrophobic agent and/or the lipids are provided in a liquid composition. In one embodiment, the liquid composition comprises an organic solvent. In another embodiment, the liquid composition is an aqueous composition. In another embodiment, the liquid composition is an aqueous composition comprising detergents. In a further embodiment, the liquid composition is a dispersion in which the hydrophobic agent and/or the lipids are dispersed in an aqueous phase.

The hydrophobic agent and the lipids may be provided together or in separate form. If they are provided together, they may be provided in form of a biological membrane or a composition derived from a biological membrane. For example, the lipids and optionally the hydrophobic agent can be provided in form of a cell membrane, an endosome, exosome, a virus like particles or a liposome. If different lipids and/or different hydrophobic agents are provided, these again may be provided together or in separate form. The biological membrane can be provided in the form of intact, amphiphilic agent-treated, or lysed cells, viruses or organelles when used in the process of the invention.

The hydrophobic agent is different from the lipids otherwise comprised in the particle. This means that if the hydrophobic agent is itself a lipid or a modified lipid, the majority of lipids comprised in the particle (i.e. greater 50 mol-% based on the total amount of lipids present in the particle) should be different from the lipid that forms the hydrophobic agent. In one embodiment, the hydrophobic agent is not a lipid; in another embodiment, the hydrophobic agent is neither a lipid nor a detergent.

"Hydrophobic agent" as used herein, means any molecule that is substantially hydrophobic. "Hydrophobic" is a term of art and refers to the property of being immiscible with or having a strong lack of affinity for/solubility in water. The hydrophobic agent can be a hydrophobic organic compound and/or a hydrophobic biomolecule. It can be a therapeutically or biologically active hydrophobic agent or a hydrophobic agent which simply stabilizes the discoidal shape of the Salipro particle. A hydrophobic agent is an agent, i.e. a compound and/or a biomolecule, which does not fully penetrate into or remain soluble in water and/or which tends to aggregate and/or partition into a hydrophobic, environment when present in aqueous phase. By being comprised in the Salipro particle, the hydrophobic agent is effectively solubilized in the hydrophobic interior of the particle. Thereby it can maintain its native functionalities such as e.g., catalytic activity or ligand binding.

Hydrophobic agents comprised in the Salipro particles generally include at least one hydrophobic (e. g., lipophilic) region capable of associating with or integrating into the hydrophobic portion of a lipid bilayer. As such the hydrophobic agent can also be a chimeric molecule, wherein a hydrophobic (e. g., lipophilic) moiety, module or compound capable of associating with or integrating into the hydrophobic portion of a lipid bilayer has been attached to another molecule. For example, a lipid- or fatty acid-coupled compound, especially a lipid- or fatty acid-coupled drug, can be used as hydrophobic agent according to this invention. In these cases, the compound or drug itself must not necessarily be hydrophobic. In some embodiments, at least a portion of the hydrophobic agent is intercalated between or penetrates into the hydrophobic portions (e.g., fatty acyl chains) of the lipid molecules in the interior of the particle.

In one embodiment, the hydrophobic organic compound and/or the hydrophobic biomolecule can, for example, be a biologically active agent, a drug, an active ingredient of a drug, an active ingredient of a cosmetic product, an active ingredient of a plant protective product, a dietary and/or nutritional supplement, a diagnostic probe, a contrast agent, a label and/or an indicator.

Hydrophobic drugs which can be included in the Salipro particle and administered to a patient in need thereof may be any drugs having low solubility in an aqueous environment. The low solubility in aqueous environment may only be apparent under certain conditions, e.g., certain pH or temperature ranges or when the concentration of the hydrophobic agent exceeds a certain threshold.

Drugs which, e.g., can be included in the Salipro particle and administered to a patient in need thereof are such for the treatment of cancer, inflammatory or infective conditions, cardiovascular diseases, neurological disorders and rheumatism among others. The hydrophobic agent can be an antioxidant, a vitamin, an anti-proliferative agent, a hormone, a steroid, or an enzyme. It can be an herbicidal or a fungicidal compound.

Some specific examples of hydrophobic drugs that can be incorporated into the Salipro particles include: curcumin, sulfonamide, such as sulfonamide, sulfamethoxazole and sulfacetamide; trimethoprim, particularly in combination with sulfamethoxazole; a quinoline such as norfloxacin and ciprofloxacin; a beta-lactam compound including a penicillin such as penicillin G, penicillin V, ampicillin, amoxicillin, and piperacillin, a cephalosporin such as cephalosporin C, cephalothin, cefoxitin and ceftazidime, other beta-lactam antibiotics such as imipenem, and aztreonam; a beta lactamase inhibitor such as clavulanic acid; an aminoglycoside such as gentamycin, amikacin, tobramycin, neomycin, kanamycin and netilmicin; a tetracycline such as chlortetracycline and doxycycline; chloramphenicol; a macrolide such as erythromycin; or miscellaneous antibiotics such as clindamycin, a polymyxin, and bacitracin for antibacterial, and in some cases antifungal infections; a polyene antibiotic such as amphotericin B, nystatin, and hamycin; flucytosine; an imidazole or a triazole such as ketoconazole, miconazole, itraconazole and fluconazole; griseofulvin for anti-Fungal diseases such as aspergillosis, candidiasis or histoplasmosis;

zidovudine, acyclovir, ganciclovir, vidarabine, idoxuridine, trifluridine, an interferon (e.g., interferon alpha-2a or interferon alpha-2b) and ribavirin for anti-viral disease; aspirin, phenylbutazone, phenacetin, acetaminophen, ibuprofen, indomethacin, sulindac, piroxicam, diclofenac; gold and steroidal antiinflammatories for inflammatory diseases such as arthritis; an ACE inhibitor such as captopril, enalapril, and lisinopril; the organo nitrates such as amyl nitrite, nitroglycerin and isosorbide dinitrate; the calcium channel blockers such as diltiazem, nifedipine and verapamil; the beta adrenergic antagonists such as propranolol for cardiovascular disease; a diuretic such as a thiazide; e.g., benzothiadiazine or a loop diuretic such as furosemide; a sympatholytic agent such as methyldopa, clonidine, guanabenz, guanethidine and reserpine; a vasodilator such as hydralazine and minoxidil; a calcium channel blocker such as verapamil; an ACE inhibitor such as captopril for the treatment of hypertension; quinidine, procainamide, lidocaine, encaidine, propranolol, esmolol, bretylium and diltiazem for the treatment of cardiac arrhythmia; lovastatin, lipitor, clofibrate, cholestyramine, probucol, and nicotinic acid for the treatment of hypolipoproteinemias; an anthracycline such as doxorubicin, daunorubicin and idambicin; a covalent DNA binding compound, a covalent DNA binding compound and a platinum compound such as cisplatin and carboplatin; a folate antagonist such as methotrexate and trimetrexate; an antimetabolite and a pyrimidine antagonist such as fluorouracil, 5-fluorouracil and fluorodeoxyuridine; an antimetabolite and a purine antagonist such as mercaptopurine, 6-mercaptopurine and thioguanine; an antimetabolite and a sugar modified analog such as cytarabine and fludarabine; an antimetabolite and a ribonucleotide reductase inhibitor such as hydroxyurea; a covalent DNA binding compound and a nitrogen mustard compound such as cyclophosphamide and ifosfamide; a covalent DNA binding compound and an alkane sulfonate such as busulfan; a nitrosourea such as carmustine; a covalent DNA binding compound and a methylating agent such as procarbazine; a covalent DNA binding compound and an aziridine such as mitomycin; a non-covalent DNA binding compound; a non-covalent DNA binding compound such as mitoxantrone and, bleomycin; an inhibitor of chromatin function and a topoisomerase inhibitor such as etoposide, teniposide, camptothecin and topotecan; an inhibitor of chromatin function and a microtubule inhibitor such as the vinca alkaloids including vincristine, vinblastin, vindesine, and paclitaxel, taxotere or another taxane; a compound affecting endocrine function such as prednisone, prednisolone, tamoxifen, leuprolide, ethinyl estradiol, an antibody such as herceptin; a gene such as the p-53 gene, the p 16 gene, the MIT gene, and the gene E-cadherin; a cytokine such as the interleukins, particularly, IL-2, IL-2, IL-4, IL-6, IL-8 and IL-12, the tumor necrosis factors such as tumor necrosis factor-alpha and tumor necrosis factor-beta, the colony stimulating factors such as granulocyte colony stimulating factor (G-CSF), macrophage colony stimulating factor (M-CSF) and, granulocyte macrophage colony stimulating factor (GM-CSF) an interferon such as interferon-alpha, interferon-beta 1, interferon-beta 2, and interferon-gamma; all-trans retinoic acid or another retinoid for the treatment of cancer; an immunosuppressive agent such as: cyclosporine, an immune globulin, and sulfasazine, methoxsalen and thalidiomide; insulin and glucagon for diabetes; calcitonin and sodium alendronate for treatment of osteoporosis, hypercalcemia and Paget's Disease; morphine and related opioids; meperidine or a congener; methadone or a congener; an opioid antagonist such as nalorphine; a centrally active antitussive agent such as dextromethorphan; tetrahydrocannabinol or marinol, lidocaine and bupivacaine for pain management; chlorpromazine, prochlorperazine; a cannabinoid such as tetrahydrocannabinol, a butyrophenone such as droperidol; a benzamide such as metoclopramide for the treatment of nausea and vomiting; heparin, coumarin, streptokinase, tissue plasminogen activator factor(t-PA) as anticoagulant, antithrombolytic or antiplatelet drugs; heparin, sulfasalazine, nicotine and steroids and tumor necrosis factor-alpha for the treatment of inflammatory bowel disease; nicotine for the treatment of smoking addiction; growth hormone, leutinizing hormone, corticotropin, and somatotropin for hormonal therapy; and adrenaline for general anaphylaxis.

The skilled person can easily determine experimentally if a certain compound incorporates well into the Salipro particles by the methods and examples described herein and in the examples of WO 2014/095576 A1, e.g., example 9. For compounds that are not detectable by spectroscopic methods, the skilled person can rely e.g., on LC-MS or thin layer chromatography to determine if a certain compound incorporates well into the Salipro particles.

The benefit of including hydrophobic agents into the Salipro particles is that they effectively become solubilized in the stable structure of the particles, which thereby can serve as deposit and/or delivery vehicle for the hydrophobic agents in aqueous environment, which is e.g., present in the majority of body fluids and tissues. Compared to classic means of solubilization via detergents or organic solvents, the Salipro particles offer the advantage that from the outside they are hydrophilic whilst the hydrophobic agent is effectively solubilized in the hydrophobic interior of the particle, by which means the hydrophobic agent can maintain its native functionalities such as e.g., catalytic activity or ligand binding. Moreover, in contrast to most detergents and organic solvents, the Salipro particles seem to be biocompatible.

Besides hydrophobic organic compounds, the lipoprotein Salipro particles have also proven capable of stably incorporating hydrophobic biomolecules such as e.g., a protein comprising a hydrophobic moiety. According to a preferred embodiment, the hydrophobic agent is a hydrophobic protein, in particular a membrane protein. The membrane protein can be selected from an integral transmembrane protein, an integral monotropic membrane protein, a peripheral membrane protein, an amphotropic protein in a lipid-bound state, a lipid-anchored protein and a chimeric protein with a fused hydrophobic and/or transmembrane domain. The term "membrane protein" as used herein does not encompass the saposin-like protein.

Integral membrane proteins are membrane proteins which are permanently bound to the lipid bilayer and usually require a detergent or apolar solvent to become displaced form the membrane. Transmembrane proteins are integral membrane proteins that span across the membrane at least once. Examples of transmembrane proteins that can be incorporated into the Salipro particles are G-protein coupled receptors (GPCRs), porters such as uniporters, symporter or antiporters, channels such as ion channels or enzymes.

Integral monotropic membrane proteins are permanently attached to the membrane only from one side and do not span across the membrane. This class includes membrane proteins that are tethered to the membrane via alpha-helical transmembrane anchors. Examples include cytochrome P450 oxidases and glycophorin A.

Peripheral membrane proteins are only temporarily or indirectly associated with the lipid bilayer or integral membrane proteins incorporated therein. Peripheral membrane proteins usually dissociate from membranes following treatment with a polar reagent with an elevated pH or high salt concentrations. Examples of peripheral membrane proteins include phospholipase A2 or C, lipoxygenases and cytochrome c.

Lipid-anchored proteins are bound to the lipid bilayer via lipidated, in particular prenylated or GPI-anchored amino acid residues. Examples include bacterial lipoproteins, G proteins and certain kinases.

Amphotropic proteins are proteins that exist in at least two conformational states, a lipid free, water-soluble state and a lipid bound state. Upon association with lipids, amphotropic proteins undergo a conformational change allowing them to become reversibly or irreversibly membrane-associated. Examples of amphotropic proteins are pore-forming toxins and antibacterial peptides.

The hydrophobic agent for use in the process of the invention can be obtained by different means. It may be of synthetic or natural origin. It may be provided in step a) in purified form or still in crude form, e.g., in form of a crude membrane or crude reaction mixture. This is especially the case if alternative (II) of the process of the invention is used, in which step b.2) can be used as a concomitant purification step for the hydrophobic agent. This can, e.g., be achieved by performing a wash step in between steps b.2) and c.2). A wash step as used herein can be limited to removal of parts of the unbound composition in which the hydrophobic agent was provided in step a) and/or contacted with the support in step b.2).

When the hydrophobic agent is a hydrophobic biomolecule, it can be obtained by purification from a natural source. Purification strategies are known by the skilled person and the skilled person is able to select a suitable purification method depending on the purification goal to be achieved. The nature of the hydrophobic biomolecule determines the purification process, which can comprise size exclusion chromatography, separation based on charge or hydrophobicity as in hydrophobic interaction chromatography or ion exchange chromatography, and/or affinity chromatography.

The term "purified" as used herein is art-recognized and does not denote any particular degree of purity. "Purified" means that a biological molecule was subjected to a purification process. The removal of any amounts of undesired molecules is regarded as purification.

Next to the saposin-like protein and the at least one hydrophobic agent, the Salipro particles obtained in the process of the invention also comprise lipids as third mandatory component. At least a part of the lipids that are to be incorporated into the Salipro particles is provided in step a) of the process of the invention.

The term "lipid" as used herein is art-recognized and refers to a natural substance of biological origin or to a synthetic lipid, wherein the lipids are soluble or partially soluble in organic solvents or partition into a hydrophobic environment when present in aqueous phase. The term "lipid" as used herein is not meant as single type of lipid molecule in the saposin lipoprotein particles obtained by the process of the invention.

The Salipro particles typically comprise a mixture of lipids. In one embodiment the lipids of the Salipro particles are a mixture that naturally occurs in archaea, viruses, prokaryotes, eukaryotic cells or eukaryotic organelle membranes from which they are obtained. For example, the lipids can be brain lipids, lipids from heart extract, lipids from liver extract, lipids from yeast extract or lipids from *E. coli* extract. In another embodiment, the lipids can be of synthetic origin. In a further embodiment, the lipids can be of semi-synthetic origin, meaning that mixtures of synthetic and natural lipids are used and/or that natural lipids have been chemically modified, e.g., to obtain fluorescently labeled lipids or head-group-modified lipids such as glycosylated lipids, functionalized lipids, pH sensitive lipids or adhesive lipids. In one embodiment, the Salipro particles comprise at least 3, 5, 10 or 20 different lipids.

In a preferred embodiment, the lipids comprise or consist of amphipathic lipids. These may be selected from the group consisting of phospholipids, glycolipids, sterols, and mixtures thereof.

Phospholipids possess a polar part that dissolves in water (the phosphate "head"), and a hydrophobic non-polar part that does not ("the lipid tail"). These parts are connected by a glycerol moiety. In water phospholipids can build a cluster with the heads facing the water and the tails facing away from it. The fatty chains in phospholipids and glycolipids usually contain an even number of carbon atoms, typically between 16 and 20. The 16- and 18-carbon fatty acids are the most common. Fatty acids may be saturated or unsaturated. The configuration of the double bonds are typically in the so called cis-configuration. Cis- and trans-isomerism is a term used in organic chemistry to refer to the stereoisomerism engendered in the relative orientation of functional groups within a molecule according to Cahn-Ingold-Prelog (CIP; Cahn, R. S. & Ingold, C. K.; Prelog, V., "Specification of Molecular Chirality". Angewandte Chemie International Edition, 5 (4), p. 385-415, 1966). Typical fatty acids present in the cell membrane are also described in Alberts et al., "The Cell", 4th edition, Macmillian Magazines Ltd, 2002 on pages 61 and 62. Further examples of the membrane lipids are phospholipids, such as phosphatidylcholine, such as POPC (1-palmitoyl-2-oleoyl-sn-glycero-3-phosphocholine), phosphatidylethanolamine, and phosphatidylserine, such as POPS (1-palmitoyl-2-oleoyl-sn-glycero-3-phospho-L-serine)phosphatidylinositol, and sphingomyelin.

Glycolipids are lipids with a carbohydrate attached thereto by a glycosidic bond. The carbohydrates are typically found on the outer surface of eukaryotic cell membranes. They extend from the phospholipid bilayer into the aqueous environment outside the cell. Examples of glycolipids are glyceroglycolipids, galactolipids, sulfolipids, glycosphingolipids, glucocerebrosides, sulfatides, gangliosides, globosides, glycophosphosphingolipids and glycophosphatidylinositols.

Sterols are a subgroup of steroids. Sterols as part of the membrane typically occur in eukaryotic membranes such as plants, animals, and fungi. Examples of sterols are cholesterol, campesterol, sitosterol, stigmasterol and ergosterol.

According to a preferred embodiment, the lipids are lipid bilayer forming lipids and/or biocompatible lipids. The term "biocompatible" as used herein denotes being biologically compatible by not producing a toxic, injurious, or immunological response in living tissue. As used herein, "bilayer-forming lipid" refers to a lipid that is capable of forming a lipid bilayer with a hydrophobic interior and a hydrophilic exterior. Any bilayer-forming lipid that is capable of associating with a SAPLIP or a derivative or truncated form thereof to assemble into a particle structure may be used in accordance with the invention. Bilayer-forming lipids include, but are not limited to, phospholipids, sphingolipids, glycolipids, alkylphospholipids, ether lipids, and plasmalogens. One type of bilayer-forming lipid may be used or a mixture of two or more types.

The lipids may also comprise lipids that are not bilayer-forming lipids. Such lipids include, but are not limited to, cholesterol, cardiolipin, phosphatidylethanolamine (this lipid may form bilayers under certain circumstances), oxysterols, plant sterols, ergosterol, sitosterol, cationic lipids, cerebrosides, sphingosine, ceramide, diacylglycerol, monoacylglycerol, triacylglycerol, gangliosides, ether lipids, alkylphospholipids, plasmalogens, prostaglandins, and lysophospholipids.

The lipids can be a mixture of the lipids listed above, but are not limited thereto. Typically, the lipids used in the process of the invention comprise at least phospholipids, glycolipids, cholesterol and mixtures thereof. According to a preferred embodiment, the lipids are eukaryotic lipids and/or prokaryotic lipids, in particular such that are typically present in any one of the membranes present in a eukaryotic or prokaryotic cell. Preferred lipids, for example, are phospholipids, glycosphingolipids, sterols, phosphatidylcholine, phosphatidylserine (PS), 2-oleoyl-1-palmitoyl-sn-glycero-3-phosphocholine (POPC), 2-oleoyl-1-palmitoyl-sn-glycero-3-glycerol (POPG), 2-oleoyl-1-palmitoyl-sn-glycero-3-phosphoethanolamine (POPE), diacylglycerol, cholesterol, sphingomyelin, galactosylceramide, gangliosides, phosphatidylinositols and sulphogalactoceramides or combinations thereof.

In another embodiment, the lipids comprise phospholipids. Examples of suitable phospholipids include, but are not limited to, DMPC, DMPG, POPC, dipalmitoylphosphatidylcholine (DPPC), dipalmitoylphosphatidylserine (DPPS), cardiolipin, dipalmitoylphosphatidylglycerol (DPPG), distearoylphosphatidylglycerol (DSPG), egg yolk phosphatidylcholine (egg PC), soy bean phosphatidylcholine, phosphatidylinositol, phosphatidic acid, sphingomyelin, and cationic phospholipids.

The lipids used in the process of the invention are typically a heterogenic mixture of lipids as it occurs in a cell or organelle membrane. But it is also possible to further include a synthetic or atypical lipid that may be a modified lipid including one or more bound functional moieties, such as a targeting moiety or a bioactive moiety.

The lipids used in the process of the invention can also comprise or consist of naturally occurring lipids, synthetic lipids, modified lipids, fats, waxes, sterols, fat-soluble vitamins, monoglycerides, diglycerides, triglycerides, phospholipids, fatty acids, glycerolipids, glycerophospholipids, sphingolipids, saccharolipids, polyketides, sterol lipids and prenol lipids or combinations thereof.

In a further embodiment, one or more of the, hydrophobic agents, the lipids and/or the saposin-like protein is/are in a detergent-solubilized state. In one embodiment, the hydrophobic agent is in a detergent solubilized stated. In another embodiment the hydrophobic agents and the lipids are in a detergent-solubilized state. Detergent-solubilized state means that the detergent brings and/or holds the respective component soluble in aqueous solution.

The term "detergent" as used herein is art-recognized and not comprised in the definition of "lipids" as used herein: While many detergents have a similarly amphiphilic general structure as compared to lipids, i.e. a polar hydrophilic head group and a nonpolar hydrophobic tail-detergents differ from lipids in the shape of the monomers, in the type of aggregates formed in solution, and in the concentration range required for aggregation. Lipids are generally substantially cylindrical in structure; the volume occupied by the hydrophobic tail is similar to the volume occupied by the polar head group. Detergent monomers are generally more cone-shaped; the volume occupied by the hydrophobic tail is smaller than the volume occupied by the polar head group. Detergents tend to aggregate into spherical or ellipsoid micelles that are water soluble without forming bilayer structures in the absence of lipids (cf. handbook "Detergents and their uses in membrane protein science" from the Anatrace website, anatrace.com).

Detergents that may be employed can be anionic, cationic, non-ionic, zwitterionic and mixtures thereof.

Typical anionic detergents are alkylbenzenesulfonates. The alkylbenzene portion of these anions is lipophilic and the sulfonate is hydrophilic. Anionic detergents can, e.g., comprise branched alkyl groups or linear alkyl groups. Examples of suitable anionic detergents are bile acids, such as deoxycholic acid (DOC), alkylbenzenesulfonates, such as branched sodium dodecylbenzenesulfonate, linear sodium dodecylbenzenesulfonate, and mixtures thereof.

Cationic detergents are similar to the anionic ones, with a hydrophobic component, but, instead of the anionic sulfonate group, the cationic surfactants have quaternary ammonium as the polar end. The ammonium center is positively charged.

Non-ionic detergents are characterized by their uncharged, hydrophilic headgroups. Typical non-ionic detergents are, e.g., based on polyoxyethylene or a glycoside. Common examples of the former include Tween, Triton, and the Brij series. These materials are also known as ethoxylates or PEGylates and their metabolites, nonylphenol. Glycosides have a sugar as their uncharged hydrophilic headgroup. Examples include octyl thioglycoside and maltosides. The glycoside headgroup can also be of high-molecular-weight such as for Saponins. Saponins consist of a sugar moiety linked to a triterpene or steroid aglycone. Depending on the non-saccharide portion of the Saponin molecule the Saponins can be divided into triterpene glycosides, steroid glycosides and steroid alkaloid glycosides. HEGA and MEGA series detergents possess a sugar alcohol as headgroup. Examples of suitable non-ionic detergents that can be used in the process according to the invention are saponins, e.g., Aescin, Bacopaside, Bacoside, Chaconine, Charantin, Digitonin, Glycyrrhizin, Ginsenoside, Holothurin, Protodioscin and Solanine and mixtures thereof. Synthetic detergents structurally similar to Saponins such as glycol-diosgenin are also suitable for use in the process according to the invention. Further examples of suitable non-ionic detergents that can be used in the process according to the invention are alkyl glycosides such as short, medium or longer chain alkyl maltosides, such as n-Dodecyl-ß-maltoside (DDM), Decanoyl-N-hydroxyethylglucamide (HEGA), n-Decanoyl-N-methyl-D-glucamide (MEGA), and mixtures thereof.

A particularly preferred detergent according to the present invention is selected from the class of saponins, in particular digitonin. Practical experiments with digitonin have shown that the process of the invention is more efficient in terms of production of Salipro particles in case digitonin is used as detergent compared to the absence of detergent or the use of other types of detergents.

Zwitterionic detergents possess a net zero charge arising from the presence of equal numbers of adverse charged chemical groups, i.e. in the sum the number of negative charges and positive charges are equal so that the overall charge is net to zero. Examples include Fos-Cholines, CHAPS/CHAPSO, lauryl-dimethyl amine-oxides (LDAO) and mixtures thereof.

In one embodiment of the invention, the detergent can be selected from the group consisting of alkylbenzenesulfonates or bile acids, cationic detergents and non-ionic or zwitterionic detergents such as lauryl-dimethyl amine-oxides (LDAO), Fos-Cholines, CHAPS/CHAPSO, saponins such as Digitonin and structurally related synthetic detergents such as glycol-diosgenin, alkyl glycoside's such as short, medium or longer chain alkyl maltosides, in particular n-Dodecyl β-D-maltoside, glucosides, maltose-neopentyl glycol (MNG) amphiphiles, amphiphilic polymers (amphipols), styrene maleic acid co-polymer (SMA), macrocycle or cyclic oligomers based on a hydroxyalkylation product of a phenol and an aldehyde (Calixarene), and mixtures thereof.

If the hydrophobic agent used in the process of the invention is in a detergent-solubilized state, it is advantageous if the detergent is a detergent having short-to medium-chain hydrophobic tails. This is particularly true if a membrane protein is incorporated as hydrophobic agent. "Short chain hydrophobic tails" as used herein means C2 to C9, such as for example in n-Nonyl-β-maltoside (NM); "medium chain hydrophobic tails" as used herein means C10 to C15, such as for example in n-Decyl-β-maltoside (DM) or n-Dodecyl-β-maltoside (DDM). In one embodiment, the detergent has from 2 to 12 carbon atoms in its hydrophobic tail, preferable from 2 to 10 and most preferred from 2 to 9 carbon atoms in its hydrophobic tail.

Practical experiments have shown that the saposin-like proteins generally do not require detergents or other solvents during purification, storage or handling. Optionally, however, also the saposin-like protein is in a detergent-solubilized state.

If the hydrophobic agent is in form of a hydrophobic biomolecule that is in a detergent-solubilized state, it may in addition be in complex with lipids, in particular annular lipids. Annular lipids, also referred to herein as "shell lipids" or "boundary lipids", represent a selected set of lipids, which preferentially bind or stick to the surface of hydrophobic biomolecules during their purification from membranes. They constitute a layer, or an annulus or shell, of lipids which are highly immobilized due to the existence of strong lipid-protein binding interactions.

In one embodiment, the detergent used to solubilize the hydrophobic agent, the lipids and/or the saposin-like protein is not carried over in substantial amounts into the Salipro particles formed in the process of the invention. In particular, the amount of detergent in the particles obtainable by the process according to the invention can be low to undetectable. In one embodiment, the obtained Salipro particle does not comprise any substantial amounts of detergent, in particular less than 0.1 wt.-%, preferably less than 0.01 wt.-%, particularly preferred less than 0.001 wt.-% detergent based on the weight of the particle. The amount of detergent (or other components) present in the particles can be determined, for example, by mass spectrometry.

In another embodiment, the hydrophobic agent and the lipids are provided in step a) in form of a biological membrane, which comprises the hydrophobic agent and the lipids that are to be incorporated into the saposin lipoprotein particles. The biological membrane can be a viral, archaeal, eukaryotic or prokaryotic membrane, i.e. a membrane derived from a virus, an archaeal, eukaryotic or prokaryotic cell or organelle. The biological membrane can be used in the process of the invention in form of intact, amphiphilic agent-treated, or lysed cells, viruses or organelles. In particular, the biological membrane can be provided in the form of cells, viruses, or organelles that have been contacted with a detergent. The membrane can comprise the hydrophobic agent and the lipids that are to be incorporated into the saposin lipoprotein particles naturally. The membrane can, however, also be derived from a virus, an archaeal, eukaryotic or prokaryotic cell or organelle that was engineered to express or comprise the hydrophobic agent and/or the lipids in its membranes. For example, if the hydrophobic agent is a hydrophobic protein, the membrane can be obtained from a cell expressing said hydrophobic protein as a transgene. The hydrophobic protein can in particular be expressed in a genetically modified (e.g., tagged) form. If the hydrophobic agent is a hydrophobic drug, the membrane can be derived from a cell that was exposed to the hydrophobic drug. If the drug is sufficiently lipophilic, this leads to incorporation of the drug into the membrane, which can be easily tested by extracting the membrane fraction and testing for the presence of the drug.

The membrane that can be used in the process of the invention is preferably selected from a viral, archaeal, eukaryotic or prokaryotic cell or organelle membrane. The term "membrane" refers to any membranes comprising a layer of lipids. Preferably, the membrane is a lipid bilayer. Sometimes the term "membrane" is used herein interchangeably for "cell membrane" and/or "organelle membrane".

If the membrane is provided in form of cells, these can be selected from prokaryotic, eukaryotic and archaeal cells. Preferably, the cells are eukaryotic cells, in particular non-human animal or human cells. Said cells may be gained from cell culture, but also from a natural source such as tissue samples, biopsy samples and other biological materials.

The term "cell membrane" refers to a biological membrane that separates the interior of cells from the outside environment. The complex structure and the plurality of components comprised in a cell membrane, such as membrane lipids and membrane proteins, are also described in detail in Alberts et al., "The Cell", 4th edition, Macmillian Magazines Ltd, 2002 on pages 583 to 614 and in Campbell et al., "Biologie", 6th edition, Spektrum Verlag, 2003 on pages 163 to 177.

In one embodiment, the Salipro particle obtained by the process of the invention essentially consists of the saposin-like protein and components of the membrane obtained from the viral, cell or organelle membrane.

The hydrophobic agent and the lipids can be provided in step a) in form of a crude membrane, which comprises the hydrophobic agent and the lipids that are to be incorporated into the saposin lipoprotein particles. "Crude membrane" as used herein refers to membranes that are no longer fully intact but still comprise essentially the natural membrane composition, in particular regarding membrane lipids and membrane protein. The crude membrane can be crude cell membranes, crude organelle membranes or portions thereof, each from an archaeal, prokaryotic or eukaryotic cell. The crude membrane can also be a crude viral envelope membrane from an enveloped virus. For example, a crude membrane fraction obtained after cell disruption or lysis of cells (of archaeal, eukaryotic or prokaryotic origin) or organelles is a "crude cell or organelle membrane". A crude viral membrane faction can be obtained after disruption of a viral envelope. "Crude viral, cell or organelle membranes" necessarily comprise the natural membrane components present in the viral envelope, cell and organelle. In particular, "crude viral, cell or organelle membranes" comprise both membrane lipids as well as membrane proteins. The disruption or lysis of the cells can occur by mechanical means but also by contacting the cells with an amphiphilic agent, in particular a detergent.

Crude cell membranes, crude organelle membranes, or crude viral membranes are no longer fully intact cell membranes, organelle membranes or viral envelopes. They spontaneously form crude membrane vesicles due to hydrophobic interactions between two given membrane rupture sites.

The hydrophobic agent and the lipids can be provided in step a) in form of the membranes that are still comprised in intact, amphiphilic agent-treated, or lysed cells, viruses or organelles. Thus, cells, viruses or organelles can be directly used in step a). They can be intact, pre-treated with an amphiphilic agent, or lysed. In particular, the hydrophobic agent and the lipids can be provided in step a) in the form of cells, viruses, or organelles that have been contacted with an amphiphilic agent, in particular with a detergent.

Membranes particularly suited for being used in the process of the invention can be obtained directly from any native cells, viruses or organelles, simply by treating these with an amphiphilic agent, in particular with a detergent. Preferably, the cells contacted with the amphiphilic agent are eukaryotic cells, in particular non-human animal or human cells. The amphiphilic agent-treated eukaryotic cells can, e.g., be neoplastic cells or cancer/tumor cells. The cells having been brought into contact with the amphiphilic agent in the method of the invention, can also be organized as, e.g., a tissue or solid tumor.

The treatment of cells, viruses or organelles with the amphiphilic agent typically takes place in a liquid environment. The treatment with the amphiphilic agent, in particular when it is a detergent, seems to have the effect that the membrane structures of cells, viruses or organelles become more fluidized and are loosened up. Although not wanting to be bound to this scientific theory, it also seems that amphiphilic agents, in particular detergents, activate the Saposin protein, perhaps by inducing an open conformation. In a preferred embodiment, no further treatment of the cells, viruses or organelles, besides the treatment with the amphiphilic agent, is performed, in particular no further treatment to achieve disruption of the cells, viruses or organelles such as by chemical and/or mechanical treatment. Suitable chemical and/or mechanical treatments to achieve disruption of cells, viruses or organelles are known to the skilled person.

In a preferred embodiment, the treatment with detergent in a liquid environment involves contacting the cells, viruses or organelles with a detergent in a concentration of 0.01 to 2000000 times the detergent's CMC, preferably in a concentration of 0.1 to 20000 times the detergent's CMC and most preferably in a concentration 1 to 2000 times the detergent's CMC. In many embodiments, best results are achieved when the detergent concentration in the liquid environment is above the detergent's CMC. Detergent concentrations below CMC seem to also already have positive effects, possibly by activating the saposin without the detergent actually solubilizing the membranes. The critical micelle concentration (CMC) is defined as the concentration of a detergent at which micelles form and all additional detergent molecules added to the system are incorporated into micelles. Typically, the cells, viruses or organelles are incubated with the amphilic agent, in particular when it is a detergent, for 0.5 min to 180 min and preferably from 30 min to 90 min. Moreover, the incubation with the detergent is typically performed at a temperature of 1 to 37° C. and preferably at a temperature of 2 to 6° C.

Step b.1)/b.2) of the Process of the Invention

In step b.1)/b.2) of the process of the invention, either the saposin-like protein (step b.1) or the hydrophobic agent (step b.2) are contacted with a support that is capable of selectively binding the hydrophobic agent or the saposin-like protein. In step b.2) of the process of the invention, the hydrophobic agent is contacted with a support that is capable of selectively binding the hydrophobic agent to the support. Alternatively, in step b.1) of the process of the invention the saposin-like protein is contacted with a support that is capable of selectively binding the saposin-like protein.

The hydrophobic agent in step b.2) or the saposin-like protein in step b.1) are preferably contacted, i.e. brought in touch, with the support in a liquid environment. Preferably, the liquid environment is an aqueous liquid environment. In certain embodiments, the aqueous liquid environment is a buffered solution at a pH of from 2.0 to 10.0, from 5.0 to 10.0 or from 5.0 to 8.5; in particular from 6.0 to 8.0 and most preferably from 7.0 to 8.0.

The term "support" as used herein refers to any support material that is capable of selectively binding the target molecule of interest. For supports employed in step b.1) of the process of the invention (alternative I), the target molecule is the saposin-like protein. For supports employed in step b.2) of the process of the invention (alternative II), the target molecule is the hydrophobic agent. The molecular structure in the support that binds the target molecule is referred to herein as "capture moiety". The molecular structure in the target molecule that is bound by the support is referred to herein as "binding moiety". Thus, the support comprises or has been functionalized to comprise capture moieties that bind corresponding binding moieties present in the target molecule of interest, i.e. in the saposin-like protein (step b.1) or the hydrophobic agent (step b.2).

The support, as used herein, can in particular be a "carrier", "carrier material" or "stationary phase" comprising such capture moieties. In a preferred embodiment, it is a solid support.

The support can be in the form of beads, a bed, a membrane or a solid support with a planar, curved, contorted, twisted and/or angular surface.

In one embodiment, the support is in the form of beads. Particularly good results are achieved with beads that are used in the prior art as chromatographic supports, e.g., in bioaffinity chromatography. These beads are most commonly based on materials made of polysaccharides, such as agarose, cellulose, lignocellulose and dextran, which can be crosslinked, or other polymers, such as polyethylene oxide. For use in the process of the invention, the bead material comprises or has been functionalized to comprise capture moieties that bind to corresponding binding moieties present in the target molecule of interest, i.e. in the saposin-like protein (step b.1) or the hydrophobic agent (step b.2). The beads used in the process of the invention such as affinity beads can have an average diameter in the range of 1 to 900 µm or 10 to 500 µm. In one embodiment, the diameter is less than 500 µm, less than 250 µm or less than 100 µm. Preferably, the beads used in the process of the invention have accessible pore structures.

The support may also form a gel due to hydration of the solids. These porous materials or gels are preferred because of the large amount of binding sites available per volume of material. The high number of binding sites provides greater binding, reactive and/or separative capacity. In another embodiment, the beads are magnetic, which allows convenient binding of the support to other surfaces. Magnetic beads are usually smaller than standard affinity beads. Thus, the beads according to the invention can also have an average diameter in the range of 600 nm to 10 µm, 400 nm to 7 µm or 200 nm to 5 µm. In another embodiment, the diameter of the, magnetic beads is less than 7 µm, less than 4 µm or less than 1 µm.

In one embodiment, the support is in the form of a bed. The bed can be formed by beads or fibres. The bed can, however, also be a continuous structure such that the bed comprises a single piece of material intersected by pores.

Examples of continuous beds are covalently cross-linked beads or fibres. The bed can be a chromatographic bed as is well-known to the skilled person from the field of protein and lipid chromatography. The bed can be based on materials made of polysaccharides, such as agarose, cellulose, lignocellulose and dextran, which can be crosslinked, or other polymers, such as polyethylene oxide. For use in the process of the invention, the bed material comprises or has been functionalized to comprise capture moieties that bind to corresponding binding moieties present in the target molecule of interest, i.e. in the saposin-like protein (step b.1) or the hydrophobic agent (step b.2).

In one embodiment, the support is in the form of a membrane. The membrane is a non-biological membrane that does not consist of typical biological membrane components such as lipids and/or membrane proteins. Preferably a chromatographic membrane is used which is well-known to the skilled person from the field of protein and lipid membrane chromatography. The membrane can be based on materials made of polysaccharides, such as agarose, cellulose, lignocellulose and dextran, which can be crosslinked, or other polymers, such as polyethylene oxide. For use in the process of the invention, the membrane comprises or has been functionalized to comprise capture moieties that bind to corresponding binding moieties present in the target molecule of interest, i.e. in the saposin-like protein (step b.1) or the hydrophobic agent (step b.2).

In one embodiment, the support is a solid support with a planar surface. "Planar" as used herein means "substantially planar" in the sense that the surface is substantially planar macroscopically. This means that the microstructure can comprise non-planar structures, and also the macrostructure can comprise areas that are not perfectly planar. In one embodiment, bent or tilted structures are also considered substantially planar in the sense of this invention if they comprise a widespread surface area. The term "solid support with a planar surface" serves to distinguish solid substantially planar supports such as chips or surface planes from the bead embodiments described above. The term "solid" as used herein is not meant to include gels. In one embodiment, solid means substantially rigid and inflexible. In another embodiment the solid support with a planar surface comprises a non-porous surface.

An example of a solid support with a planar surface that can be used in the process of the invention is a chip or biosensor surface. In one embodiment, the planar surface of the solid support is made of metal. In particular the metal can be selected from the group consisting of gold, silver, copper, aluminum, and mixtures thereof. In another embodiment, the surface is made of glass and/or a synthetic resin, i.e. a polymer material. For use in the process of the invention, the planar surface of the solid support comprises or has been functionalized to comprise capture moieties that bind to corresponding binding moieties present in the target molecule of interest, i.e. in the saposin-like protein (step b.1) or the hydrophobic agent (step b.2). In one embodiment, the dimensions of the solid support with a planar surface are in the range of 1 to 50 mm$^2$, in particular 5 to 25 mm$^2$.

The support comprises a capture moiety that enables it to selectively bind the target molecule of interest via a binding moiety in the target molecule. For supports employed in step b.1) of the process of the invention (alternative I), the target molecule is the saposin-like protein. For supports employed in step b.2) of the process of the invention (alternative II), the target molecule is the hydrophobic agent.

The terms "a capture moiety" or "a binding moiety" are used herein in the sense of "at least one capture moiety" and "at least one binding moiety". Supports used in the process of the invention will typically comprise multiple target moieties, which may be the same or different. Typically, the support will comprise a plurality of capture moieties of the same type. The target molecule can comprise one or more binding moieties. For example, when the binding is based on affinity interactions, the target molecule may comprise one or multiple copies of an affinity tag. When the binding is based on hydrophobic interactions, the target molecule may comprise one or more hydrophobic binding sites, etc.

The target molecule comprises a binding moiety that is selectively bound by the capture moiety of the support. The term "binding moiety" refers to any molecular structure in the target molecule, i.e. the hydrophobic agent or the saposin-like protein according to the process of the invention that allows selective binding to the corresponding capture moiety of the support. The binding moiety of the target molecule and the capture moiety of the support form a complimentary interaction pair. Collectively the terms "capture moiety" and "binding moiety" will be referred to as "recognition moieties" herein.

Accordingly, in alternative (I) of the process of the invention, the support comprises a capture moiety, and the saposin-like protein comprises a binding moiety, wherein the capture moiety is capable of selectively binding the binding moiety in the saposin-like protein. In alternative (II) of the process of the invention, the support comprises a capture moiety, and the hydrophobic agent comprises a binding moiety, wherein the capture moiety is capable of selectively binding the binding moiety in the hydrophobic agent. In terms of their binding to the support, the "hydrophobic agent" and the "saposin-like protein" will be referred to herein collectively as "target molecule".

The term to "bind" as used herein can mean to "immobilize", "capture", "fix", "couple" or "retain" the target molecule on the support. The term "selectively" denotes that the support preferentially, primarily and/or almost exclusively binds the target molecule, i.e. the hydrophobic agent or the saposin-like protein. The selective binding can be achieved by means of electrostatic interaction, hydrophobic interaction, affinity binding and/or covalent bond formation between the capture moiety of the support and the binding moiety of the target molecule. Usually the binding will be reversible. In one embodiment, however, the binding to the support is substantially irreversible. In another embodiment, the binding to the support is by way of covalent bonds.

As a general note, whenever reference is made herein to suitable capture moiety/binding moiety pairs, the inverse pair is also meant to be described. In other words, in many cases, the capture moiety on the support and the binding moiety in the target molecule can be used interchangeably.

The binding can involve a linker or spacer that connects the binding and capture moieties. The linker or spacer can be an at least bifunctional molecule that reacts with or binds to both the binding and the capture moiety or it can be comprised in the binding or capture moiety.

The capture moiety of the support can enable selective binding of the target molecule by a variety of modes, which will be further explained in detail below. For example: (i) capturing the target molecule by chemically coupling its binding moiety to the capture moiety of the support by a chemical bond, (ii) capturing the target molecule via affinity-based interactions between the capture moiety of the support and a natural or engineered binding moiety in the target molecule, (iii) indirect binding of the target molecule by engineering the capture moiety in the support to bind to a bridging agent (e.g., a peptide epitope, substrate analog or ligand), which is selectively bound by the binding moiety in the target molecule, (iv) capturing the target molecule via hydrophobic interactions between the capture moiety of the support and a natural or engineered binding moiety in the target molecule, and/or (v) capturing the target molecule via charge-based interactions between the capture moiety of the support and a natural or engineered binding moiety in the target molecule.

In one embodiment, the selective binding of the target molecule to the support in step b.1)/b.2) is achieved by chemically coupling the binding moiety of the target molecule to the capture moiety of the support by means of a chemical bond. This can be achieved by taking advantage of functional groups in the target molecule such as thiol-, amino-, hydroxyl-, aldehyde- or carboxyl groups. Suitable capture moieties of the support to react with such binding moieties of the target molecule are known to the skilled person. The skilled person is able to select a suitable capture moiety/binding moiety pair depending on the type of coupling to be achieved. Thiol groups in the target molecules can, for example, be reacted with maleimides, disulfides or iodoacetamide used as capture moieties on the support or vice versa. Primary amines in target molecules can, for example, be reacted with succinimide esters (such as N-hydroxysuccinimide, sulfosuccinimide or other succinimidyl esters), imidoesters or isothiocyanates (such as phenylisothiocyanate) used as capture moieties on the support or vice versa. Carboxy groups of target molecules can, for example, be reacted with carbodiimides (such as 1-Ethyl-3-(3-dimethylaminopropyl)carbodiimide) used as capture moieties on the support or vice versa.

Depending on the chemistry chosen, the coupling of the target molecules to the support via formation of chemical bonds may be substantially irreversible, which may be beneficial for certain applications requiring particularly tight binding of the formed Salipro particles to the support. On the other hand, capture via affinity-based recognition moieties, hydrophobic interaction or electrostatic interaction is usually reversible and has the advantage of easy elution in step d) and the possibility of regenerating and re-using the support.

In another embodiment, the selective binding of the target molecule to the support in step b.1)/b.2) is achieved by affinity-based interactions between the capture moiety of the support and a natural or engineered binding moiety in the target molecule. In this way, target molecules with a natural or engineered binding moiety are selectively bound by the support's capture moiety using affinity-based interactions.

Examples of natural capture moiety/binding moiety affinity-based pairs are lectins that bind to certain sugar moieties in the target molecule (e.g., if this is a glycosylated membrane protein) or antibodies that recognize natural epitopes of the target molecule (or vice versa). Post-translational modifications such as glycosylation, sulfation, palmitoylation, myristoylation, ubiquitination or SUMOylation can also serve as binding moieties according to the invention. Various other natural affinity-based interactions between a capture and a binding moiety are known to the skilled person.

Particular important examples of engineered affinity-based capture moiety/binding moiety pairs that are useful in the process of the invention come from the well-known area of affinity tags. Accordingly, in one embodiment the capture moiety or the binding moiety is an affinity tag and the corresponding other recognition moiety is a moiety having high affinity for the affinity tag. For example, a Protein A-sepharose resin can be used as support (the Protein A then is the affinity tag on the support) together with a hydrophobic agent-antibody fusion (the Fc portion of the antibody then is the binding moiety in the target molecule). If a hydrophobic agent-antibody complex is used, the antibody acts as a linker as described above. Preferably, the binding moiety in the target molecule is an affinity tag. For example, a $Ni^{2+}$-NTA resin can be used as support (the $Ni^{2+}$-NTA then being the capture moiety) together with a His-tagged target molecule (the His-tag then being the affinity tag and the binding moiety in the target molecule).

Affinity-tags have the advantage that they are easily introduced, for example, via standard cloning or genetic engineering, and bind to well-known, often commercially available capture moiety-bearing supports. The saposin-like protein used in step b.1) or the hydrophobic agent used in step b.2) (if the latter is a hydrophobic protein) can be in an affinity tagged form. This can easily be obtained by introducing an affinity tag in form of a peptide or polypeptide into the target molecule by cloning or genetic engineering. Accordingly, in this embodiment, the hydrophobic agent (if the latter is a hydrophobic protein) and/or the saposin-like protein are employed as affinity tagged fusion proteins in step b.2) and step b.1), respectively. The term "fusion protein" is art-recognized and refers to proteins fused to another peptide or polypeptide by recombinant DNA technology. Sometimes the term "fusion protein" is used herein interchangeably with "chimeric protein".

Interactions between an affinity tag and a corresponding capture moiety were originally developed to aid in protein purification and immobilization. Protein target molecules may be modified at the genetic level with certain peptide sequences, known as affinity tags that bind to known capture moieties. Affinity tags, as used herein, generally fall into three categories: a) peptide sequences that bind to small molecules; b) proteins that bind to small molecules; and c) peptides or proteins that bind to antibodies. An affinity tag may also be a small molecule compound (e.g., a ligand) that has a suitable binding partner. The affinity tag may be covalently attached to the target molecule used in the process of the invention. For example, nitrilo tri-acetic acid, when complexed to $Ni^{2+}$ ($Ni^{2+}$-NTA), is a common capture moiety that binds proteins modified with a stretch of histidines, known as a histidine tag, defining an affinity tag usable as binding moiety in the target molecule.

"Affinity tag" is given its ordinary meaning in the art. An affinity tag is any biological or chemical material that can readily be attached to a target biological or chemical molecule. Affinity tags may be attached to a target biological or chemical molecule by any suitable method. For example, in some embodiments, the affinity tag may be attached to the target molecule using genetic methods. For example, the nucleic acid sequence encoding the affinity tag may be positioned anywhere within the nucleic acid that enables the affinity tag to be expressed with the biological molecule, for example, within, adjacent to, or nearby. In other embodiments, the affinity tag may also be attached to the target biological or chemical molecule after the molecule has been produced (e.g., expressed or synthesized). As one example, an affinity tag such as biotin may be chemically coupled, for instance covalently, to a target protein or peptide to facilitate the binding of the target to streptavidin.

Affinity tags include, for example, metal binding tags such as histidine tags, GST (in glutathione/GST binding), streptavidin (in biotin/streptavidin binding) or maltose (which binds to MBP or maltose binding protein). Other affinity tags include Myc or Max in a Myc/Max pair, or polyamino acids, such as polyhistidines. At various locations herein, specific affinity tags are described in connection with binding interactions. The molecular structure in the support that the affinity tag interacts with (e.g., binds selectively to), which usually is its known biological or chemical binding partner, is the "capture moiety" as used herein.

Affinity tag or antigen (used as binding moiety)/capture moiety pairs useful for step b.1)/b.2) of the process of the invention are, for example, polyhistidine/NTA/Ni2+, glutathione S transferase/glutathione, maltose binding protein/maltose, streptavidin/biotin, biotin/streptavidin, antigen (or a fragment of an antigen)/antibody (or a fragment of an antibody), and the like.

Further affinity tag or antigen (used as binding moiety)/capture moiety pairs useful for step b.1)/b.2) of the process of the invention are, for example, an antibody/peptide interaction, an antibody/antigen interaction, a fragment of an antibody/antigen interaction, a nucleic acid/nucleic acid interaction, a protein/nucleic acid interaction, a peptide/peptide interaction, a protein/protein interaction, a small molecule/protein interaction, a glutathione/GST interaction, a maltose/maltose binding protein interaction, a carbohydrate/protein interaction, a carbohydrate derivative protein interaction, a peptide tag/metal ion-metal chelate interaction, a peptide/NTA-Ni interaction, epitope tag (e.g., V5-tag, Myc-tag, FLAG-tag, or HA-tag)/antibody interaction, a Protein A/antibody interaction, a Protein G/antibody interaction, a Protein L/antibody interaction, a fluorescent protein (e.g., GFP)/antibody interaction an Fc receptor/antibody interaction, a biotin/avidin interaction, a biotin/streptavidin interaction, a zinc finger/nucleic acid interaction, a small molecule/peptide interaction, a small molecule/target interaction, and a metal ion/chelating agent/polyamino acid interaction.

Any of the above mentioned affinity tags can be present on the hydrophobic agent or the saposin-like protein which is selectively bound to the support in step b.1)/b.2) of the process of the invention. The vice versa may also be the case, i.e. the affinity tags can be present on the support and the respective capture moieties on the target molecules, or optionally an intermediary linker. Any of the above mentioned affinity-based interaction pairs can be applied for the process of the invention.

In another embodiment, the affinity tag of the target molecule is a fluorescent tag. Such fluorescent tags are useful for detecting and following a particular hydrophobic agent or a particular type (species) of Salipro particle during its generation in the process of the invention. GFP and its variants are Examples of commonly used fluorescent tags.

The inventor's research revealed that it is also possible to use specifically tagged membrane proteins present in crude membranes as hydrophobic agent in the process of the present invention. This is possible by tagging the membrane protein of interest in the underlying cell or virus that the crude membranes are derived from. The crude membranes comprising the tagged hydrophobic protein can then be used in step a) of the process of the invention to provide the hydrophobic protein and the lipids. The tagging preferentially occurs on the genetic level, e.g., by genetically engineering or by inserting a vector carrying a tagged transgene into the virus, cell or organelle that the crude membrane vesicles are obtained from.

In another embodiment, the selective binding of the target molecule to the support in step b.1)/b.2) is achieved by indirect binding of the target molecule via its binding moiety to the capture moiety of the support. This indirect binding of the target molecule can be achieved by engineering the capture moiety of the support to bind to a bridging agent (e.g., a peptide epitope, substrate analog or ligand), which is selectively bound by the binding moiety in the target molecule. In this way, secondary interactions between captured bridging agents can be used to selectively bind the saposin-like protein or the hydrophobic agent to the support. Examples of bridging agents are cofactors, substrate analogs or inhibitors of enzymes, ligands or peptide epitopes. These bridging agents can be coupled to the capture moiety of the support, where they can selectively bind the target molecule. For example, when a cofactor, a substrate analog or an inhibitor of an enzyme is used as the bridging agent, the respective enzyme is the target molecule and the respective binding pocket in the enzyme constitutes the binding moiety.

In further embodiments, the selective binding of the target molecule to the support in step b.1)/b.2) is achieved by capturing the target molecule via hydrophobic interactions between the capture moiety of the support and a natural or engineered binding moiety in the target molecule, and/or by capturing the target molecule via charge-based interactions between the capture moiety of the support and a natural or engineered binding moiety in the target molecule. The skilled person knows suitable capture moieties to mediate such interactions. In case hydrophobic interactions are used to selectively bind the target molecule to the support, the support, for example, comprises hydrophobic groups such as aromatic groups, $C_8$-$C_{24}$ alkyl, $C_8$-$C_{24}$ alkenyl, or $C_8$-$C_{24}$ fatty acids as capture moieties. In case electrostatic interactions are used to selectively bind the target molecule to the support, suitable anion- and cation exchange moieties can be used as capture moieties on the support. In particular, commercially available anion or cation exchange resins can be used as support. Functional groups commonly used in anion exchangers include, for example, quaternary ammonium, diethylaminopropyl or diethylaminoethyl. Functional groups commonly used in cation exchangers include, for example, sulfonic acid, methylsulfonate or carboxymethyl.

Step c.1)/c.21 of the Process of the Invention

In step c.1)/c.2) of the process of the invention, self-assembly of the saposin lipoprotein particle occurs by contacting the support-bound target molecule (the hydrophobic agent or the saposin-like protein) with the remaining components of the saposin lipoprotein particle.

In case of alternative (I) of the process of the invention, step c.1) requires that the support-bound saposin-like protein is contacted with the hydrophobic agent to allow for the self-assembly of the saposin lipoprotein particle. Without wanting to be bound to this theory, it is likely that neighboring captured saposin-like proteins contribute to form an individual Salipro particle. Also the support can be present in form of a very dynamic and dense 3D structure so that an interaction of neighboring captured saposin-like proteins is facilitated. In a preferred embodiment, additional saposin-like protein is added before, during or after step c.1) to further aid the self-assembly into the saposin lipoprotein particles.

In case of alternative (II) of the process of the invention, step c.2) requires that the support-bound hydrophobic agent is contacted with the saposin-like protein to allow for the self-assembly of the saposin lipoprotein particle.

Preferably, the self-assembly of the particle in step c.1) and/or c.2) is carried out at a pH from 2.0 to 10.0, in particular 6.0 to 10.0, preferably from 6.0 to 9.0, particularly preferred from 7.0 to 9.0, and most preferred from 7.0 to 8.0. Preferably the contacting in step c.1)/c.2 is performed in a liquid environment. Preferably, the liquid environment is an aqueous liquid environment. In certain embodiments, the aqueous liquid environment is a buffered solution at a pH of from 2.0 to 10.0, from 5.0 to 10.0 or from 5.0 to 8.5; in particular from 6.0 to 8.0 and most preferably from 7.0 to 8.0.

Any material that remains unbound after contacting the support-bound particle components in step c.1)/c.2), can be recycled from the liquid environment, stored and reused for another application.

It is a remarkable and surprising property of saposin-like proteins that they can self-assemble hydrophobic agents into Salipro particles by simply being incubated with lipids and the hydrophobic agents. The research underlying the present invention revealed that surprisingly this self-assembly even works very efficiently when one of the primary constituents, i.e. either the saposin-like protein (process alternative I) or the hydrophobic agent itself (process alternative II) are bound and immobilized on a support. The self-assembly then occurs under more challenging conditions at the interphase between support and liquid environment containing the remaining components.

Research of the inventors has shown that the particles obtained by the process of the invention are disc-shaped like the Salipro particles of the prior art that were formed in purely liquid environments based on the free, random motion of all involved particle components in the liquid environment. In a preferred embodiment, the assembled Salipro particles are disc-shaped. In another preferred embodiment, the Salipro particles do not comprise an aqueous or hydrophilic core. In yet another embodiment, the Salipro particles are disc-shaped and do not comprise an aqueous or hydrophilic core.

In a preferred embodiment, the Salipro particles generally are considered disc-shaped. In particular, they can have a Stokes radius (hydrodynamic radius) RS in the range of from 2 nm to 500 nm, in particular from 2 nm to 200 nm or 3 nm to 150 nm, preferably from 3 nm to 100 nm. The skilled person knows how to determine the Stokes radius. This is preferably done by eluting the particles from the support and subjecting them to analytical gel filtration (size exclusion chromatography), in comparison with standards of known Stokes radii. In particular, the particles can be subjected to a gel filtration step on e.g., a Superdex 200 HR10 30 gel filtration column and eluted with a suitable buffer at pH 7.5 and 0.5 ml/min at room temperature. Absorbance is monitored at 280 nm for protein. The column is calibrated using a mixture of protein standards of known Stokes radii such as e.g., thyroglobulin 669 kDa (RS=8.5 nm), ferritin 440 kDa (RS=6.1 nm) catalase 232 kDa (RS=4.6 nm), lactate dehydrogenase 140 kDa (RS=4.1 nm), bovine serum albumin 66 kDa (RS=3.55 nm) and horse heart cytochrome c 12.4 kDa (RS=1.8 nm). The standard proteins should span Rs values above and below that of the particle of interest. A calibration curve is generated by plotting the elution position vs Rs for the standard proteins. This generally gives an approximately linear plot, but otherwise, it is satisfactory to draw lines between the points and read the Rs of the protein of interest from its elution position on this standard curve.

In some embodiments, e.g., when a bulky hydrophobic agent, such as a membrane protein, or higher amounts of lipids are present in the particles, the Stokes radius will be larger than 3.2 nm, in particular at least 3.5 nm, at least 5.0 nm or at least 10.0 nm.

The Salipro particles may also be examined via transmission electron microscopy in a support bound or "free" state. If the particles are large enough, they can be analyzed via negative-stain electron microscopy and single particle analysis.

Structural analysis has indicated that in many cases, in the Salipro particles, the membrane lipids assemble into a discoidal bilayer-like structure of discrete size in the interior of the particle. The saposin-like protein component generally defines the boundary of the discoidal bilayer and provides structure and stability to the particle. In most embodiments, the interior of the particle includes a hydrophobic region (e.g., comprised of lipid fatty acyl chains). In contrast to liposomes, Salipro particles usually do not comprise a hydrophilic or aqueous core. The particles are preferably disc-shaped, having a flat, discoidal, roughly circular lipid bilayer circumscribed by amphipathic α-helices provided by two or more saposin-like proteins, which are associated with hydrophobic surfaces of the bilayer around the periphery of the disc.

In some embodiments, and depending on the size of the hydrophobic agent incorporated into the Salipro particles, the in principal discoidal shape of the (empty) Salipro particles can be approximated by a square, triangle or cylinder. For example, a Salipro particle approximated by a cylinder can possess a ratio of the maximum height to the maximum diameter (major axis length) of at least 1.0:1.1, in particular 1.0:1.5, 1.0:2.0, 1.0:4.00, 1.0:8.00 or 1.0:9.00. The maximum height of the discoidal particle generally is at least 3.5 nm, in particular at least 5 nm, as determined by transmission electron microscopy of the eluted free particles or, if the particles are large enough, via negative-stain electron microscopy and single particle analysis. Preferably, the Salipro particle has a top, a bottom and a circumferential side surface, with the maximum diameter (major axis length) of the top and bottom surface being larger than the height of the circumferential side surface. In some embodiments of the Salipro particle, the saposin-like protein is at least partially located to surround the circumferential side surface of the particle.

In some embodiments, the average maximum diameter (major axis length) of the disc-shaped Salipro particle, as determined by transmission electron microscopy or, if the particles are large enough, via negative-stain electron microscopy and single particle analysis is from between 2 nm to 200 nm, in particular from 3 nm to 150 nm, preferably from 3 nm to 100 nm. In another embodiment, the average maximum diameter (major axis length) of the disc-shaped particle is from 3 nm to 80 nm, in particular from 3 nm to 60 nm. Practical experiments have shown that particles having an average maximum diameter (major axis length) of 3 nm to 20 nm are particularly easily obtainable with the process of the invention.

In another embodiment, the particles are defined by a substantially monodisperse population of disk structures, as assessed by the gel filtration elution profile of the eluted free particles on for example a HiLoad Superdex™ 200 16/60 GL column.

Generally, the predominant interaction between the saposin-like protein and a lipid bilayer in the Salipro particle is through hydrophobic interactions between residues on the hydrophobic faces of amphipathic α-helices of the saposin-like protein molecules and hydrophobic surfaces of lipids, for example, phospholipid fatty acyl chains, at the edge of the bilayer at the periphery of the bioactive agent delivery particle. An amphipathic α-helix of the saposin-like protein includes both a hydrophobic surface in contact with a hydrophobic surface of the lipid bilayer at the periphery of the particle, and a hydrophilic surface facing the exterior of the particle and in contact with the aqueous environment when the particle is suspended in aqueous medium.

In another embodiment, the saposin lipoprotein particles are stable in aqueous solution and may be lyophilized for long term storage, followed by reconstitution in aqueous solution. "Stability" or "stable" as used herein means low to undetectable levels of particle fragmentation, low to undetectable levels of aggregation or quality deterioration during preparation, transportation, and storage of the particles.

In a preferred embodiment, the particles and the library of particles according to the process of the invention are stable in aqueous solutions at a pH of from 2.0 to 10.0, in particular 6.0 to 10.0, preferably from 6.0 to 9.0, particularly preferred from 7.0 to 9.0, and most preferred from 7.0 to 8.0. In another embodiment, the libraries and particles according to the process of the invention are stable in aqueous solutions at a temperature of from $-210°$ C. to $80°$ C., in particular $-210°$ C. to $40°$ C., $-210°$ C. to $30°$ C. or $-210°$ C. to $4°$ C. for at least 1 day, at least 2 days, at least 7 days, at least 2 weeks, at least 1 month, at least 6 months or at least 12 months, as determined, for example, by visual inspection (clear and precipitate-free solution) or analytical gel filtration (less than 50%, in particular from 1 to 40% fragmentation of the particles). Practical experiments have shown that the Salipro particles are also stable at temperatures from $4°$ C. to $40°$ C. in aqueous solutions at a pH of from 5.0 to 8.0 for at least 1 day, at least 2 days, at least 7 days, at least 2 weeks, at least 1 month or at least 3 months as determined, for example, by visual inspection (clear and precipitate-free solution) or analytical gel filtration (less than 50%, in particular from 1 to 40% fragmentation of the particles). The Salipro particles have also proven to be stable in aqueous solutions at a pH of from 5.0 to 8.0 and a temperature of from $40°$ C. to $75°$ C. for at least 10 minutes, as determined, for example, by visual inspection (clear and precipitate-free solution) or analytical gel filtration (less than 50%, in particular from 1 and 40% fragmentation of the particles). In some embodiments, the particles may be lyophilized for long term storage, followed by reconstitution in aqueous solution. In some embodiments, the Salipro particles are stable in lyophilized form at $-210°$ C. to $80°$ C., in particular $-210°$ C. to $40°$ C., $-210°$ C. to $30°$ C. or $-210°$ C. to $4°$ C. for at least 1 day, at least 2 days, at least 7 days, at least 2 weeks, at least 1 month, at least 6 months or at least 12 months, as determined, for example, by analytical gel filtration after reconstitution in an appropriate buffer at pH 7.5 (less than 50%, in particular less than 40% or from 1, to 40% fragmentation of the particles). "Fragmentation" as used herein means that in the gel filtration elution profile, the size of the peak (i.e. peak height) corresponding to the Salipro particle has decreased at the expense of the peak size of free non-lipid-bound SAPLIP and/or free lipids and/or aggregates, as compared to the peak size of the freshly prepared Salipro particle. Accordingly, a fragmentation of 40% for example means that the peak size (i.e. the height of the peak in the gel filtration elution profile) has decreased by 40% as compared to the peak size prior to storage (100%).

Practical experiments have shown that the Salipro particles are particularly stable also in aqueous solutions that are substantially free of detergents. Preferably, the aqueous solution comprises a detergent concentration that is lower than the critical micelle concentration (CMC) of the employed detergent. The CMC is defined as the concentration of detergent above which micelles form and all additional detergent molecules added to the system are incorporated into micelles.

At least a part of the lipids that are to be incorporated into the Salipro particles is provided in step a) of the process of the invention. Additional lipids can be provided in any further stage of the process, in particular during step(s) b.1)/b.2) and/or c.1)/c.2) of the process of the invention. In one embodiment, the lipids are selected from the group consisting of archaeal, prokaryotic, eukaryotic or viral lipids, and mixtures thereof.

In an embodiment specific to alternative (I) of the process of the invention, the support-bound saposin-like protein is contacted in step c.1) with an archaeal, prokaryotic, eukaryotic or viral membrane that was provided in step a). The membrane comprises the hydrophobic agent and at least parts of the lipids that are to be incorporated into the Salipro particle. This allows formation of a library of Salipro particles wherein the library comprises a heterogenic mixture of saposin lipoprotein particles with different membrane lipid and optionally membrane protein compositions.

The support-bound saposin-like protein seems not to distinguish between the membrane constituents that it is contacted with. Therefore, if the support-bound saposin-like protein is contacted with a complex biological membrane in step c.1) of the process of the invention, this results in a support-bound library of Salipro particles reflecting the complexity and presenting snapshots of the membrane lipid and protein composition of the biological membrane employed. Preparing support-bound libraries of a biological membrane's lipidome/proteome in this way has the advantage that discrete units of the original membrane structure seem to get preserved in the Salipro particles. Such support-bound libraries are advantageous for specialty applications, such as high throughput screening and biosensor applications.

The term "library" according to the invention means a set (complex plurality) of different Salipro particles. In particular, the difference can lie in the size and composition of the particles, especially in the composition of the membrane components contained therein, i.e. membrane lipids, and, optionally, membrane proteins. Typically the libraries are a mixture of "lipid-only particles" and different kinds of membrane protein-containing Salipro particles. This is meant by the term "different membrane lipid and optionally membrane protein compositions" used herein. The particles in the library can also differ in their content and composition of different membrane lipids. Preferably, some particles in the library differ in the fact whether or not and which membrane protein they contain.

By contacting the support-bound saposin-like protein in step c.1) with an archaeal, prokaryotic, eukaryotic or viral membrane provided in step a) a library of saposin like particles with different membrane lipid and optionally membrane protein compositions is obtained.

The library of Salipro particles that can be obtained by the process of the invention can comprise Salipro particles that lack membrane proteins, i.e. be essentially only comprised of saposin-like protein and membrane lipids from the crude membranes ("empty" Salipro particles). The library will, however, also comprise Salipro particles comprising one or more membrane protein ("filled" Salipro particles).

A eukaryote is any cell or organism whose cells contain a nucleus and optionally further organelles enclosed by membranes. In one embodiment the membrane used in the process according to the invention is membrane from a eukaryote, e.g., the cell membrane and/or membrane stemming from a cell organelle. Examples for organelles are the Golgi apparatus, mitochondria, peroxisomes, endoplasmic reticulum, chloroplasts, nucleus and the like.

Examples of eukaryotes are plants, animals, and fungi such as yeast and molds. Preferred eukaryotic cells that can be used in the process according to the invention are selected from the group consisting of mammalian cells, in particular animal and human cells, insect cells, avian cells, fungal cells such as yeast cells, plant cells, and mixtures thereof. The term mammalian cells especially also includes animal and human cells which are kept in culture medium.

A prokaryote is a single-celled organism that lacks a nucleus. Prokaryotic cells are simpler and smaller than eukaryotic cells, and lack membrane organelles. Examples of prokaryotes are bacteria. Exemplary bacterial phyla are acidobacteria, actinobacteria, aquificae, armatimonadetes, bacteroidetes, caldiserica, chlamydiae, chlorobi, chloroflexi, chrysiogenetes, cyanobacteria, deferribacteres, deinococcus-thermus, dictyoglomi, elusimicrobia, fibrobacteres, firmicutes, fusobacteria, gemmatimonadetes, lentisphaerae, nitrospira, planctobacteria, proteobacteria, spirochaetae, synergistetes, tenericutes, thermodesulfobacteria, thermotogae and verrucomicrobia. Preferred prokaryotic cells that can be used in the process according to the invention are bacteria, in particular pathogenic bacteria, and mixtures thereof.

Archaea are related only distantly to prokaryotes and eukaryotes. A detailed overview is given, e.g., in De Rosa et al., "Structure, Biosynthesis, and Physicochemical Properties of Archaebacterial Lipids", MICROBIOLOGICAL REVIEWS, p. 70-80 Vol. 50, No. 1, 1986, or Albers et al., "The archaeal cell envelope", Nature Reviews Microbiology, 9, p. 414-426, 2011. De Rosa et al. report that archaeal membranes comprise molecules that differ strongly from those of prokaryotes and eukaryotes.

Prokaryotes and eukaryotes comprise membranes comprising mainly glycerol-ester lipids, whereas archaea comprise membranes comprising glycerol-ether lipids. Ether bonds are chemically more resistant than ester bonds. This stability might help archaea to survive extreme temperatures and very acidic or alkaline environments. Prokaryotes and eukaryotes may comprise ether lipids, but in contrast to archaea, these lipids are only a minor or no component of the membrane.

In addition, archaeal lipids are based upon an isoprenoid sidechain. Isoprenoid side chains are long chains containing 20, 25 or up to 40 carbon atoms with optionally multiple side-branches. They may also comprise cyclopropane or cyclohexane rings. This is in contrast to the fatty acids found in other organisms' membranes as described above. Although isoprenoids play an important role in the biochemistry of many organisms, only the archaea use them to make phospholipids. In some archaea, the lipid bilayer may be replaced by a monolayer.

Examples of archaea are methanogenic archaea, halobacteria and thermo-acidophilic archaea. Preferred archaea that can be used in the process according to the invention are extremophile archaea and mixtures of different extremophile archaea.

The virus structure and components of the virus' membrane, if applicable, differ from eukaryotic, prokaryotic and archaea membranes. This is reported in more detail in, e.g., Lorizate et al., "Comparative lipidomics analysis of HIV-1 particles and their producer cell membrane in different cell lines", Cellular Microbiology, 15(2), p. 292-304, 2013 and Brugger et al., "The HIV lipidome: A raft with an unusual composition", PNAS, Vol. 103, No. 8, p. 2641-2646, 2006.

Lorizate et al. report that various studies indicated that the HIV-1 membrane differs from the producer cell plasma membranes suggesting virus budding from pre-existing subdomains or virus-mediated induction of a specialized budding membrane. The lipid analysis of plasma membranes and HIV-1 purified from two different cell lines revealed a significantly different lipid composition of the viral membrane compared with the host cell plasma membrane, independent of the cell type investigated. Virus particles were significantly enriched in phosphatidylserine, sphingomyelin, hexosylceramide and saturated phosphatidylcholine species when compared with the host cell plasma membrane of the producer cells. They showed reduced levels of unsaturated phosphatidylcholine species, phosphatidylethanolamine and phosphatidylinositol. Cell type-specific differences in the lipid composition of HIV-1 and donor plasma membranes were observed for plasmalogen-phosphatidylethanolamine and phosphatidylglycerol, which were strongly enriched only in HIV-1 derived from MT-4 cells. MT-4 cell-derived HIV-1 also contained dihydrosphingomyelin. Taken together, these data reported by Lorizate et al. support that HIV-1 selects a specific lipid environment for its morphogenesis and is not identical or similar to its hosts' cell membranes. Usually, the particles and libraries obtained by the process of the invention do not contain viral proteins and/or viral membranes.

Enveloped viruses include Orthomyxoviruses, Flaviviruses and Retroviruses. Examples of enveloped viruses are influenza virus A, influenza virus B, influenza virus C, influence virus D, Batken virus, Bourbon virus, Dhori virus, hepatitis C virus, Dengue virus, Japanese encephalitis virus, Entebbe bat virus, Yellow fever virus, Zika virus, HTLV 1 and HIV.

Step d of the Process of the Invention

In step d) of the process of the invention the support-bound Salipro particles can be eluted from the support. This step is optional, because for certain applications (e.g., biosensor or lab-on-a-chip), the support bound Salipro-particle is the product of interest. In these cases there thus is no need to elute the particle from the support.

The covalent coupling of the hydrophobic agent or the saposin-like protein to the support via formation of chemical bonds (i) is in many cases substantially irreversible. For elution, the chemical bond must be either dissolved, e.g., by performing the reverse coupling reaction or a different cleavage reaction. For example, a linker with a scissile bond can be employed. This can, e.g., be a linker comprising a protease cleavage site, which allows elution with incubation with the protease (e.g., TEV protease). In contrast, binding of the Salipro particle via affinity interaction (ii), indirect interaction via a bridging agent (iii), hydrophobic interaction (iv) or electrostatic interaction (v) is usually reversible and allows relatively easy elution of the particles and often regeneration of the support and its re-use.

Elution of the assembled Salipro particles from the support can be achieved by a variety of techniques, which depend on the type of interaction between the support and the target molecule, in particular between the capture moiety and the binding moiety as described above. Suitable elution methods are known to the skilled person. The skilled person is able to select a suitable elution strategy depending on the kind of interaction with which the target molecule is selectively bound to the support.

The term "elution" as used herein refers to the removal or displacement of the support-bound Salipro particles.

For example, Salipro particles bound by affinity interactions between one of its components and the support (ii) are eluted by providing specific molecules to the liquid environment which disrupt and/or replace the affinity interaction. For example, if the target molecule is tagged with a His-tag and the support carries $Ni^{2+}$-NTA capture moieties, elution is carried out by contacting the support bound Salipro particles with imidazole. In the same way, if the target molecule is tagged with a GST-tag, and the support comprises glutathione as capture moiety, elution can be carried out by contacting the support bound Salipro particles with glutathione. Elution of Salipro particles that are bound by a bridging agent mediating an indirect interaction between the target molecule and the support (iii) can be carried out by cleaving the bridging agent or linker or by disrupting the interactions between the bridging agent and the capture and/or binding moiety. In case of receptor/ligand-like interactions between the capture and binding moiety, elution can be carried out by using a competitive binding substance such as sugars in case of lectins attached to a support binding to sugar moieties on the target molecule. Elution of Salipro particles bound by hydrophobic interactions (iv) to the support can be achieved by decreasing the salt concentration in the liquid environment to promote solvation and thus elution of the bound material. In case the Salipro particle is bound by electrostatic interactions to the support (v), elution can be carried out by changing the pH or the salt concentration in the liquid environment surrounding the support-bound Salipro particles.

According to a particular embodiment, the steps described above, in particular steps a), b.1)/b.2), c.1)/c.2) and d) are performed at a temperature of from 1° C. to 85° C., in particular from 1° C. to 40° C., particularly preferred from 1° C. to 30° C. A temperature of between 1° C. to 25° C., in particular 1° C. to 20° C., most particular 3° C. to 15° C. is sufficient for most applications. However, by the methods taught herein, the skilled person can determine the optimal incubation temperature with regards to the temperature stability of the membranes, compounds, lipids and proteins used.

The term "essentially" used herein means that also traces of further components used in the process according to the invention can be present in the Salipro particles such as further components of the crude membranes used for the provision of hydrophobic agent and/or lipids or agents used in the process, such as detergents. That the Salipro particle essentially consists of at least one saposin-like protein and components of the membrane obtained from the cell or the organelle membrane shall, however, in particular mean that no further lipids and/or proteins are added.

The Salipro particle or the library of Salipro particles obtainable according to the process of the invention can be used in medicine, in particular for use in preventing, treating or lessening the severity of a disease or for use in a diagnostic method, a cosmetic treatment or for use as vaccination formulation.

For example, the Salipro particle can be included into a pharmaceutical composition for delivering one or more membrane proteins and/or lipids to an individual in need thereof, wherein the composition comprises Salipro particles as described above.

Besides the Salipro particles, the pharmaceutical composition can optionally comprise a (further) pharmaceutically acceptable vehicle, carrier or adjuvant.

When the Salipro particles are used in a pharmaceutical composition, the individual components of the particles and the pharmaceutical composition should be pharmaceutically acceptable. As used herein, the term "pharmaceutically acceptable" refers to components, compounds or agents that are, within the scope of sound medical judgment, suitable for use in contact with the tissues of humans and lower animals without undue toxicity, irritation, allergic response and the like, and are commensurate with a reasonable benefit/risk ratio.

The pharmaceutical compositions containing Salipro particles can be administered to humans and other animals orally, rectally, parenterally, intracisternally, intravaginally, intraperitoneally, topically (as by powders, ointments, or drops), bucally, as an aerosol, an oral or nasal spray, or the like, depending on the severity of the disease or condition being treated. In particular, the pharmaceutical composition can be formulated for enteral, parenteral and/or topical administration. It can be administered as a capsule, infusion or injection, a brushable or potable composition or as an aerosol. Also described herein are pharmaceutical compositions wherein the Salipro particles are present in solid form, as a dispersion or in solution.

The Salipro particles are also useful for diagnostic and/or cosmetic applications. For example, Salipro particles comprising a detectable antigen or tag as described for example above, may be used as diagnostic agents and applied for diagnostic purposes. For the latter, it may also be very useful to employ the Salipro particles in the support-bound form as obtainable by the present invention if the elution step d) is omitted. Examples of diagnostic and Life Science research tools according to the invention include particles with tagged incorporated membrane proteins, tagged saposin-like protein, tagged lipids, incorporated fluorophores or contrast agents (for example for MR imaging). The tag can for example be a fluorescent tag.

In another aspect, the Salipro particles are useful as vaccination formulation, as carrier thereof or as drug delivery vehicle. Many pathogenic antigens that could be particularly potent in vaccinations are exposed on the surface and/or comprised in the outer cell membrane of eukaryotic or prokaryotic pathogens or disease cells (e.g., cancer cells) in a patient. These antigens can, e.g., be derived from pathogenic lipids, other hydrophobic biomolecules or membrane proteins. With the Salipro particles, such antigens can effectively be incorporated into the particles which then can be used as antigen-presenting delivery vehicles in vaccination formulations. Along these lines, the Salipro particles are also useful to serve as antigen-presenting delivery vehicles for generating antibodies against lipids or membrane proteins in suitable host animals, preferably in mammals such as e.g., rabbits, goats, lamas, mice and primates.

Also described herein is the use of Salipro particles as a tool for drug development, drug screening and drug discovery.

For example, a particular membrane protein drug target, such as a cell surface receptor or ion channel, may be incorporated into the Salipro particles and solubilized thereby in its native state. Such particles can then be employed in assays to study the activity of the drug target membrane protein in its native lipid bilayer environment or used in drug screenings to identify new drugs. According to the process of the invention, the Salipro particles are assembled while selectively bound with one particle component to a support. The thus obtained support-bound Salipro particles can be directly employed in chip-based applications such as lab-on-a-chip as well as Surface Plasmon Resonance (SPR), grating-coupled interferometry (GCI) or other biosensor applications.

Label-free optical SPR biosensors are the gold standard for measuring the binding affinity and kinetics of molecular interactions. Mainly four SPR biosensor platforms exist: GE Healthcare's Biacore T100, Bio-Rad's ProteOn XPR36, ForteBio's Octet RED384, and Wasatch *Microfluidics's* IBIS MX96.

Alternatively to SPR biosensors, waveguide interferometers based on GCI can be used to characterize molecular interactions and/or to determine kinetic rates, affinity constants and concentrations of the interacting molecules.

While SPR- and GCI-based optical measurements detect refractive index changes within an evanescent field near a sensor surface due to changes in mass by complex formation of the interacting molecules, other biosensor systems apply different detection strategies: calorimetric biosensors record heat absorbed or released by a reaction. Potentiometric biosensors detect distribution of charges leading to an electrical potential. Alternatively, amperometric biosensors may represent the movement of electrons produced in a redox reaction. In addition, biosensors can also detect light output during the course of a reaction or difference in light absorbance between the reactants and products (optical biosensors). Moreover, piezo-electric biosensor take advantage of effects that are attributable to the mass of the reactants or products bound to the biosensor surface (piezo-electric biosensors). All these biosensor applications have in common that they benefit from having one of the molecules to be studies bound to a support. The process of the invention provides an easy and straight forward "one step" process for incorporating hydrophobic agents of interest directly into support-bound Salipro particles. This obviates the need for an additional coupling step and is therefore advantageous in terms of process efficiency and costs.

The process of the invention can also be used as a tool for membrane protein purification, membrane protein expression, for membrane and/or membrane protein research, in particular lipidomics and proteomics, preferably for the isolation, identification and/or study of membranes and/or membrane proteins or creation of a lipidome or proteome library or database.

The Salipro particles are generally useful for rendering otherwise insoluble membrane proteins and membrane domains or components soluble in aqueous solutions in their native membrane bilayer microenvironment. The Salipro particles obtained with the method of the invention can be employed in a wide variety of new applications in membrane protein research. For example, the Salipro particles allow studying membrane proteins incorporated in the Salipro particles by methods such as nuclear magnetic resonance (NMR), X-ray crystallography, electron microscopy (EM), mass spectrometry, isothermal titration calorimetry (ITC), differential light scattering, small-angle X-ray scattering (SAXS), enzyme-linked immunosorbent assay (ELISA), fluorescence-activated cell sorting (FACS), biochemical assays, high throughput screening (HTS) and the like.

The library of particles obtainable with certain embodiments of the process of the invention are particularly useful for research in the field of systems biology, especially lipidomics and membrane proteomics. The libraries of the invention may be suitable for capturing and solubilizing the lipidome and/or proteome of a virus, cell or cell organelle. Typical analytical techniques in lipidomics and proteomics are technologies such as mass spectrometry (MS), nuclear magnetic resonance (NMR) spectroscopy, fluorescence spectroscopy, and computational methods. Applying these methods or techniques to the Salipro particles will allow further elucidation of the role of natural lipids and membrane proteins in many metabolic diseases such as, for example, cancer, autoimmune diseases, obesity, atherosclerosis, stroke, hypertension and diabetes. If the library is in a support-bound state, in particular bound to a solid support with a substantially planar surface, spatial two-dimensional separation and immobilization of the Salipro particles is achieved, which aids in the analysis of such complex mixtures.

The entire Salipro particle library obtained from a particular cell or organelle that could be a disease target can be used for drug screening purposes to identify new molecular drug targets, such as membrane proteins or lipids present in the membrane of the target cell or organelle.

BRIEF DESCRIPTION OF THE DRAWINGS

The invention will hereinafter be described with reference to the Figures, which depict certain embodiments of the invention. The invention, however, is as defined in the claims and generally described herein. It should not be limited to the embodiments shown for illustrative purposes in the Figures below.

FIG. 1 is a schematic illustration of the shape and molecular organization of the Apolipoprotein A-1 containing nanodisc particle (10) of the prior art (EP 1 596 828 B1 discussed above) comprising lipids (3) and apolipoprotein scaffold protein (11).

In FIGS. 2a, 2b and 2c a Salipro particle comprising a saposin-like protein (2), lipids (3), a membrane protein (4a)/oligomeric membrane protein (4b) and optionally a hydrophobic compound (4c) is shown, wherein the membrane protein (4a,4b) comprises a binding moiety (5).

In FIGS. 3a, 3b and 3c a Salipro particle comprising saposin-like protein (2), lipids (3) and optionally a membrane protein (4a)/oligomeric membrane protein (4b) is shown, wherein the saposin-like protein (2) comprises a binding moiety (5).

In FIGS. 4a and 4b a Salipro particle comprising saposin-like protein (2), lipids (3), a hydrophobic compound (4c) and optionally a membrane protein (4a) is shown, wherein the hydrophobic compound (4c) comprises a binding moiety (5).

In FIGS. 5a and 5b a Salipro particle comprising saposin-like protein (2), lipids (3), a hydrophobic compound (4c) and optionally a membrane protein (4a) is shown, wherein the saposin-like protein (2) comprises a binding moiety (5).

FIGS. 6a to 6f are schematic illustrations of modes to provide the hydrophobic agent for certain embodiments. In FIGS. 6a and 6d crude membrane vesicles (7, 7') are depicted, comprising lipids (3) and optionally membrane proteins (4a, 4b), wherein in FIG. 6a the membrane protein (4a) comprises a binding moiety (5). In FIG. 6b and FIG. 6e a membrane protein (4a) associated with lipids (3) and detergent molecules (6) is shown, wherein in FIG. 6b the membrane protein (4a) comprises a binding moiety (5). In FIG. 6c and FIG. 6f a hydrophobic compound (4c) associated with lipids (3) and detergent molecules (6) is depicted, wherein in FIG. 6c the hydrophobic compound (4c) comprises a binding moiety (5).

FIGS. 7a to 7b are schematic illustrations of modes to provide the saposin-like protein for particular embodiments.

In FIGS. 7a and 7b a saposin-like protein (2) is depicted, wherein in FIG. 7a the saposin-like protein (2) comprises a binding moiety (5).

FIGS. 8a to 8d are schematic illustrations of particular embodiments of hydrophobic agent or saposin-like protein bound to the support in step b.2) and b.1), respectively. In FIG. 8a a saposin-like protein (2) is depicted, which is bound via its binding moiety (5) to the capture moiety (13) of the support (12). In FIG. 8b a hydrophobic compound (4c) associated with lipids (3) and detergent molecules (6) is depicted, which is bound via its binding moiety (5) to the capture moiety (13) of the support (12). In FIG. 8c a membrane protein (4a) associated with lipids (3) and detergent molecules (6) is shown, which is bound via its binding moiety (5) to the capture moiety (13) of the support (12). In FIG. 8d a crude membrane vesicle (7) comprising lipids (3) and membrane proteins (4a, 4b) is shown, which is bound via the binding moiety (5) in the membrane protein (4a) to the capture moiety (13) of the support (12).

In FIG. 9a a support (12)-bound membrane protein (4a) associated with lipids (3) and detergent molecules (6) is contacted with saposin-like protein (2) to allow in step c.2) for the self-assembly of a Salipro particle (compare FIG. 2a). In FIG. 9b a support (12)-bound hydrophobic compound (4c) associated with lipids (3) and detergent molecules (6) is contacted with saposin-like protein (2) to allow in step c.2) for the self-assembly of a Salipro particle (compare FIG. 4a). In FIG. 9c a support (12)-bound crude membrane vesicle (7) comprising lipids (3) and membrane proteins (4a, 4b) is contacted with saposin-like protein (2) to allow in step c.2) for the self-assembly of a Salipro particle (compare FIG. 2a).

FIG. 10a to 10d are schematic illustrations of steps b.1) and c.1) of particular embodiments, wherein the saposin-like protein is bound to the support in step b.1) and contacted with the hydrophobic agent in step c.1). In FIG. 10a a support-bound (12) saposin-like protein (2) is contacted with a membrane protein (4a) associated with lipids (3) and detergent molecules (6) to allow in step c.1) for the self-assembly of a Salipro particle (compare FIG. 3b). In FIG. 10b a support-bound (12) saposin-like protein (2) is contacted with a crude membrane vesicles (7, 7') comprising lipids (3) and membrane proteins (4a, 4b) to allow in step c.1) for the self-assembly of Salipro particles and formation of a library of particles (compare FIG. 3a, 3b, 3c). In FIG. 10c a support-bound (12) saposin-like protein (2) is contacted with a hydrophobic compound (4c) associated with lipids (3) and detergent molecules (6) to allow in step c.1) for the self-assembly of a Salipro particle (compare FIG. 5a). In FIG. 10d a support-bound (12) saposin-like protein (2) is contacted with a hydrophobic compound (4c) and membrane protein (4a) both of which are associated with lipids (3) and detergent molecules (6) to allow in step c.1) for the self-assembly of a Salipro particle (compare FIG. 5b).

FIG. 11 indicates Size Exclusion Chromatography analysis of Salipro particle assembly upon binding of tagged SLC transporter (a membrane protein) to an affinity support and contacting the support-bound SLC transporter with different concentrations of Saposin A.

FIG. 12a indicates Size Exclusion Chromatography analysis of Salipro particles obtained from Sample 5 in Experiment 1c. The fractions obtained during Size Exclusion Chromatography were analyzed by SDS-PAGE indicating that fractions 13, 14 and 15 mainly contain the assembled Salipro particles. FIG. 12b indicates Size Exclusion Chromatography analysis of fraction 14 as shown in FIG. 12a.

FIG. 13 indicates Size Exclusion Chromatography analysis of Salipro particle assembly upon binding of the Saposin A to an affinity support and contacting the support-bound Saposin A with additional untagged Saposin A, brain lipids and optionally a hydrophobic agent in form of bacterial ion channel membrane protein T2.

FIG. 14a to 14b reproduces FIGS. 4A and 4B of Bruhn (2005), Biochem J 389 (15): 249-257.

The sequences are provided as SEQ ID Nos 7-46 as indicated in table 1 above.

Figure 1:
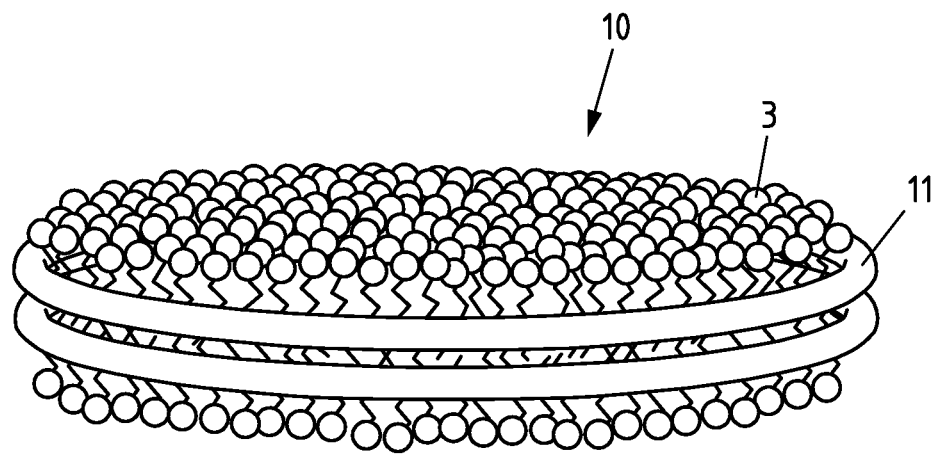
FIG. 1 depicts a prior art lipoprotein particle.

FIG. 1 depicts a prior art Apolipoprotein A-1 containing nanosdisc particle (10) (see, EP 1 596 828 B1 discussed above) comprising lipids (3) and Apolipoprotein A-1 as lipid binding polypeptide (11). Contrary to the apolipoprotein-derived nanodiscs of the prior art, the lipid binding polypeptide of the present invention, i.e. the saposin-like protein, does not enclose the lipids in a double belt-like fashion (cf. FIGS. 2, 3 and 4) but rather the particles of the invention are held together by a core comprising the membrane lipids which is surrounded by two or more approximately V-shaped or boomerang-shaped lipid binding polypeptides arranged in a head-to-tail orientation with substantially no direct protein-protein contacts between the individual saposin-like proteins within a given Salipro particle obtained by the process of the invention (cf. FIGS. 2, 3 and 4).

Figure 2A:
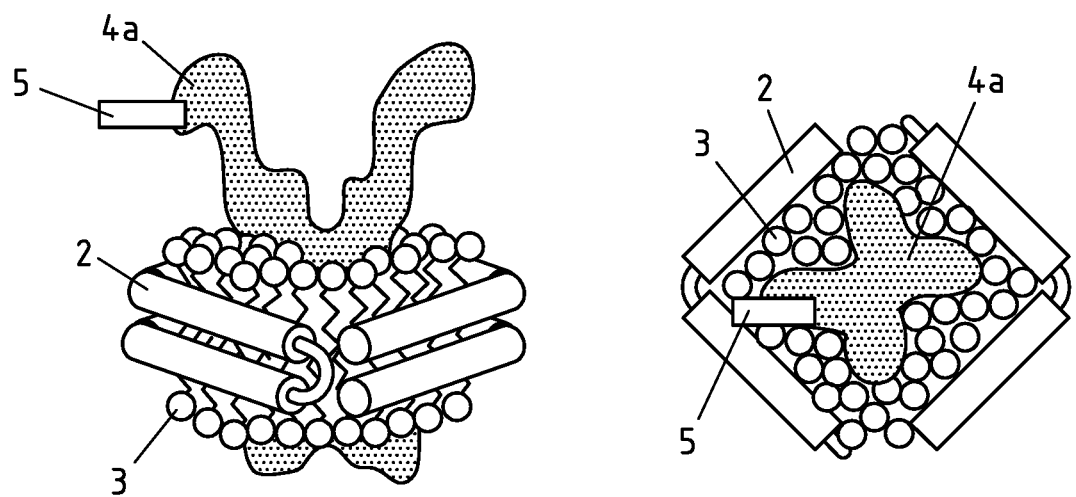
FIGS. 2a to 2c are schematic illustrations of Salipro particles in side view (left) and in top view (right) obtained by particular embodiments.
Figure 2B:
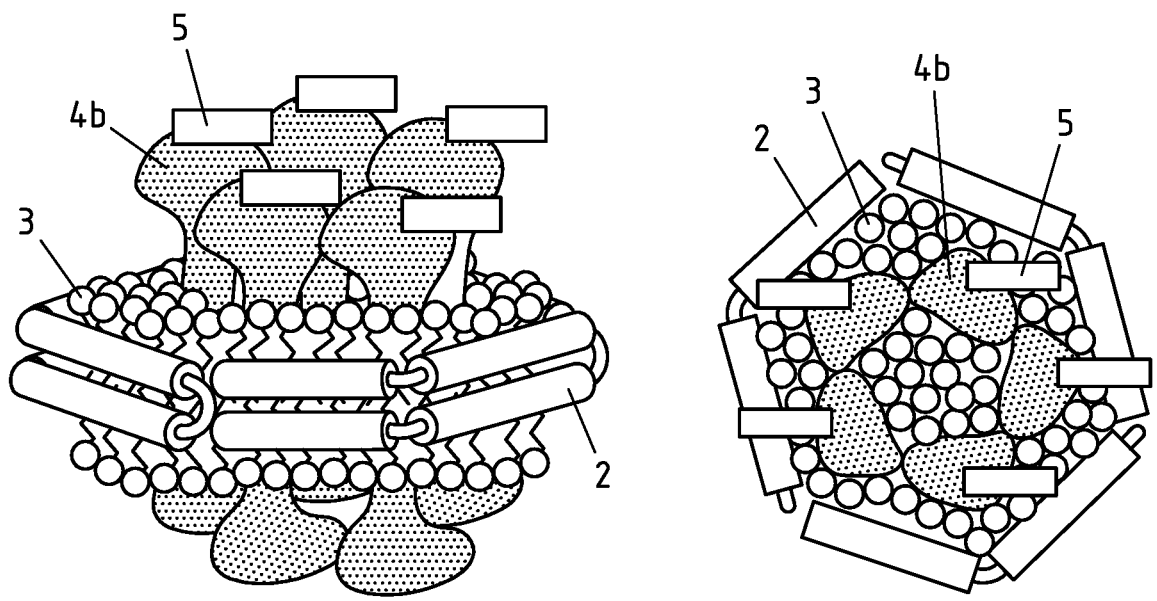
Figure 2C:
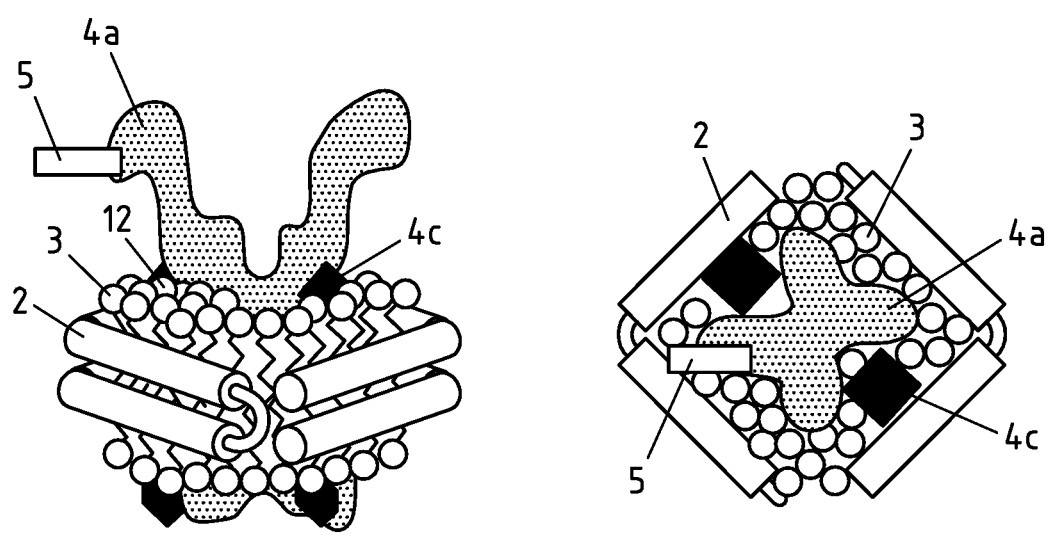

FIG. 2a to 2c are schematic illustrations of Salipro particles obtained according to certain embodiments. The particles of FIGS. 2a, 2b and 2c comprise a saposin-like protein (2), a plurality of different lipids (3), a membrane protein (4a)/oligomeric membrane protein (4b) and optionally a hydrophobic compound (4c). The membrane protein (4a, 4b) in FIGS. 2a to 2c comprises a binding moiety. The binding moiety in the membrane protein can be a natural or engineered binding moiety. The binding moiety of the membrane protein can reside at the N-terminus, C-terminus or within the amino acid sequence of the membrane protein. In case the membrane protein contains an engineered binding moiety, it can be attached to the membrane protein during or after protein synthesis. In another embodiment, which is not depicted, the membrane protein (4a, 4b) can possess multiple binding moieties of the same or different type. The lipids (3) of the Salipro particles depicted in FIG. 2a to 2c differ from each other, meaning that the lipid composition of a Salipro particle is not uniform or homogeneous. Depending on how the membrane protein (4a, 4b) in step a) is provided, the composition of the lipids will vary. In a further embodiment, which is not shown, the Salipro particles may also comprise further components that are typically present in a viral, archaeal, eukaryotic and/or prokaryotic membrane. The lipids (3) and the membrane proteins (4a, 4b) can stem from the same viral, archaeal, eukaryotic or prokaryotic membrane source or from different sources.

The particles of FIG. 2a to 2c are not drawn to scale. Depending on the size of the membrane protein (4a, 4b) incorporated into the particles, the particles can be substantially different in size compared to other particles. The Salipro particles obtained by the process of the invention are flexible in size. For example, the particle in FIG. 2b harboring an oligomeric membrane protein is larger than and contains more Saposin subunits (2) as compared to the particle in FIG. 2a, which contains a monomeric membrane protein. Depending on the size of the Salipro particles the particles comprise two or more saposin-like molecules per particle, which are arranged in a head-to-tail fashion. The particles depicted in FIGS. 2a and 2c comprise two saposin-like molecules, whereas the particle depicted in FIG. 2b comprises 3 saposin-like molecules.

FIGS. 2a, 2b and 2c depict—in simplified form as side view and top view—a Salipro particle comprising a saposin-like protein (2), lipids (3) from a viral, archaeal, eukaryotic and/or prokaryotic membrane source, a membrane protein (4a, 4b) and optionally a hydrophobic compound. The membrane protein (4a) can be an integral transmembrane protein in monomeric form. However, the membrane protein can also be an integral transmembrane protein in oligomeric form as depicted in FIG. 2b or a peripheral membrane protein, an amphotropic protein in a lipid-bound state, a lipid-anchored protein or a chimeric protein with a fused hydrophobic and/or transmembrane domain, all of which may be in a monomeric or oligomeric state.

The particle depicted in FIG. 2c differs from 2a and 2b in that it additionally comprises a hydrophobic compound (4c) of natural or synthetic origin. The number of hydrophobic compounds within one Salipro particle can vary. The hydrophobic compound can form close interactions with the lipids (3) and/or any kind of membrane protein. The membrane protein can for example be a monomeric transmembrane protein (4a) as depicted in FIG. 2c.

Figure 3A:
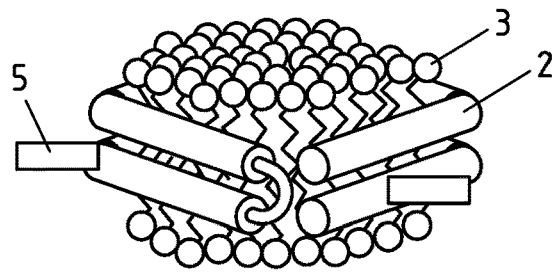
FIGS. 3a to 3c are schematic illustrations of Salipro particles in side view (left) and in top view (right) obtained by certain embodiments.
Figure 3A:
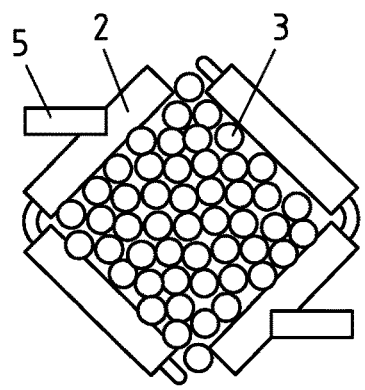
Figure 3B:
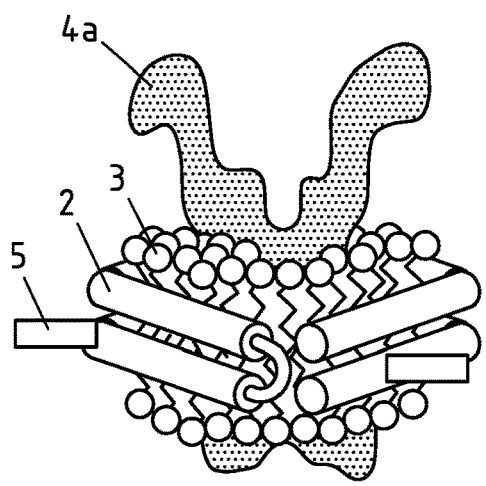
Figure 3B:
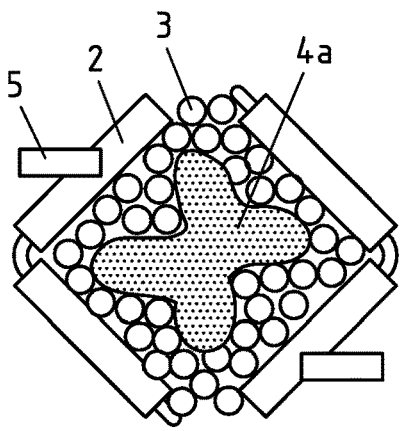
Figure 3C:
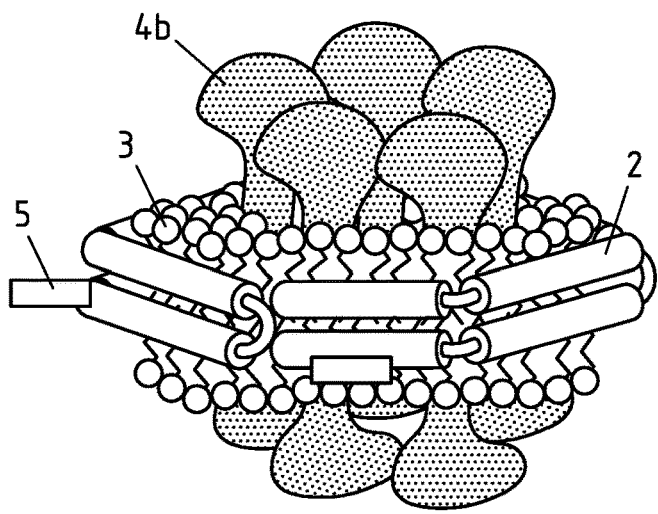
Figure 3C:
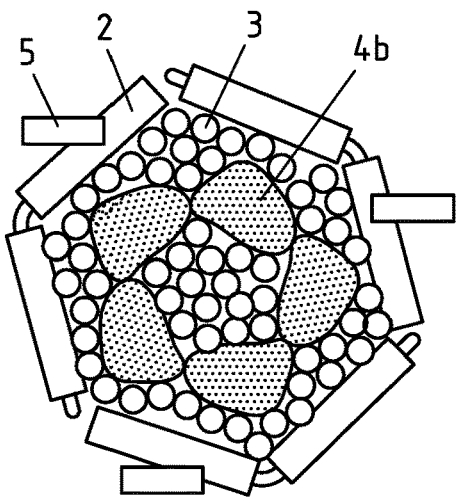

FIG. 3a to 3c depict—again in simplified schematic form (side view left and top view right) and not drawn to scale—Salipro particles obtained according to particular embodiments. The particles depicted in FIGS. 3a, 3b and 3c comprise saposin-like protein (2), lipids (3) and optionally a transmembrane protein of monomeric or oligomeric form (4a, 4b), wherein the saposin-like protein (2) has a binding moiety (5). In another embodiment, which is not shown, the saposin-like protein (2) can possess multiple binding moieties of the same or different type. As described for the particles of FIG. 2 the particles depicted in FIG. 3 can vary regarding their lipid (3) composition and their size to incorporate any kind of hydrophobic protein by simply incorporating more than two saposin-like proteins (2) to form the particle.

Figure 4A:
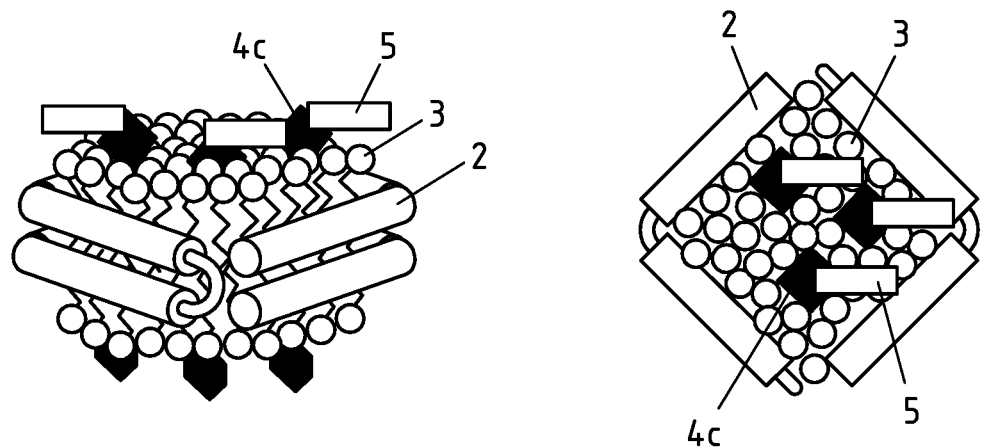
FIGS. 4a to 4b are schematic illustrations of Salipro particles in side view (left) and in top view (right) obtained by particular embodiments.
Figure 4B:
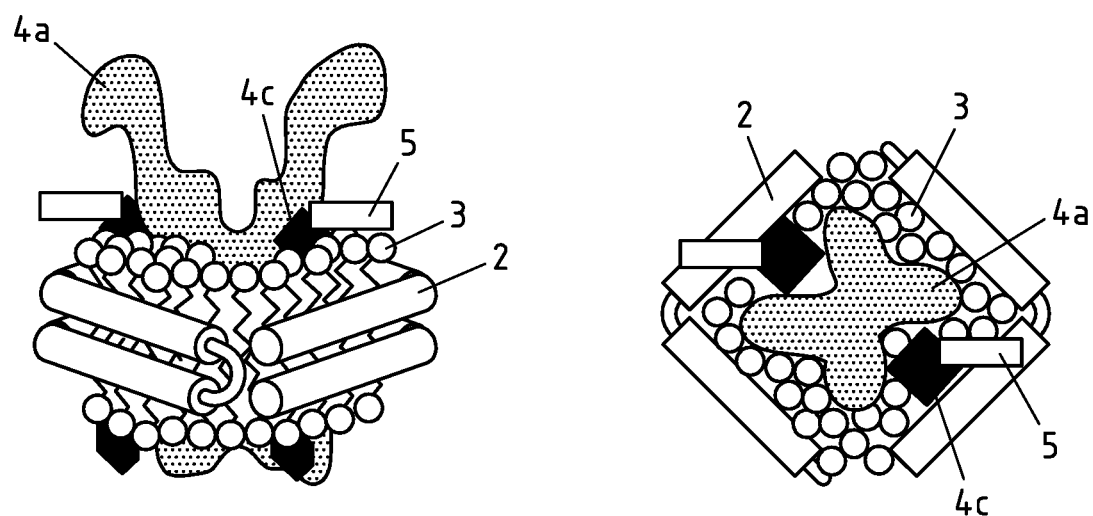

FIGS. 4a and 4b show unscaled schematic illustrations of Salipro particles in side view (left) and top view (right) of certain embodiments of the invention. The particles depicted in FIGS. 4a and 4b comprise a saposin-like protein (2), lipids (3), a hydrophobic compound (4c) and optionally a membrane protein (4a). The hydrophobic compound reveals a binding moiety, which can be of natural or engineered origin. While the natural binding moiety can form an internal part of the hydrophobic compound (4c), the engineered binding moiety is usually attached after synthesis of the hydrophobic compound or after purification of a natural hydrophobic compound to a suitable terminal reactive group. In a further embodiment, which is not shown, the Salipro particles may comprise different kinds of hydrophobic compounds having the same natural or engineered binding moiety. The particles of FIGS. 4a and 4b can vary in the number and kind of lipids (3), hydrophobic compounds (4c), membrane proteins (4a) and saposin-like proteins (2) incorporated into the particles.

Figure 5A:
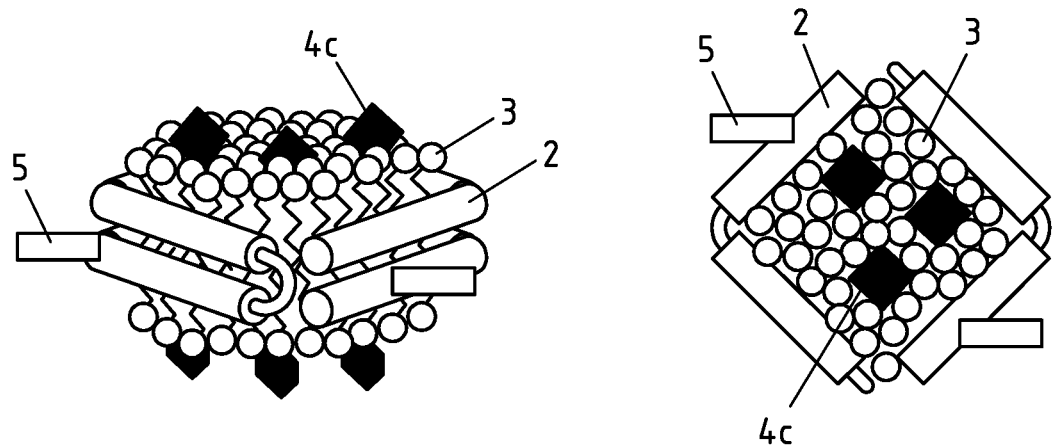
FIGS. 5a to 5b are schematic illustrations of Salipro particles in side view (left) and in top view (right) obtained by certain embodiments.
Figure 5B:
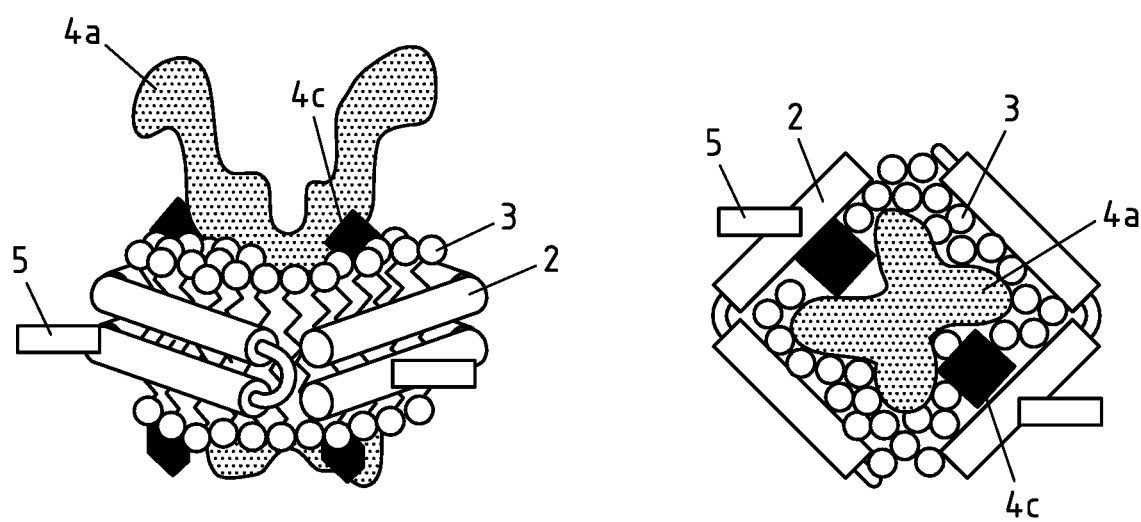

FIGS. 5a and 5b show—again in unscaled and schematic form (side view left and top view right)—Salipro particles of particular embodiments. The particles depicted in FIGS. 5a and 5b differ from the particles depicted in FIGS. 4a and 4b in that the saposin-like protein (2) and not the hydrophobic compound (4c) bears a binding moiety. Regarding different compositions of the particles depicted in FIGS. 5a and 5b, which are not shown, the same considerations apply as described for FIGS. 4a and 4b.

FIG. 6a to 6f depict particular embodiments which provide the hydrophobic agent in form of a hydrophobic biomolecule (i.e. for example a transmembrane protein in monomeric (4a) or oligomeric (4b) form) or hydrophobic compound in step a) of the process of the invention. In FIG. 6a the membrane proteins (4a, 4b) are provided as crude membrane vesicles (7, 7'). The membrane vesicles (7, 7') can be of viral, archaeal, eukaryotic or prokaryotic origin. They comprise a plurality of lipids (3) and in case of vesicle (7) a plurality of membrane proteins, here exemplified in simplified form by only two membrane proteins (4a, 4b), wherein membrane protein (4a) has a binding moiety (5). Vesicle (7') is an "empty" lipid-only particle. The crude membrane vesicles, exemplified as vesicles (7, 7') can be directly obtained by lysing for example a cell or cell organelle of archaeal, prokaryotic or eukaryotic origin. Crude membrane vesicles can also be obtained by rupturing a viral envelope. Vesicles such as (7) and (7') usually form spontaneously upon lysis or membrane rupture. The crude membrane vesicle can comprise or be associated with detergent molecules (not depicted herein). In FIG. 6b a membrane protein (4a) with a binding moiety (5) is depicted, which is not present within a natural membrane or a crude membrane vesicle, but is in an artificial, detergent-solubilized state (see association of the membrane protein (4a) with lipids (3) and detergent molecules (6) depicted in FIG. 6b). In FIG. 6c a hydrophobic compound with a binding moiety (5) in detergent-solubilized state is depicted, meaning that the hydrophobic compound is embedded within a micelle containing lipids (3) and detergent molecules (6). Optionally, the membrane protein (4a) depicted in FIG. 6b or the hydrophobic compound depicted in FIG. 6c is solubilized by detergent molecules only. The modes to deliver the hydrophobic agents depicted in FIGS. 6d to 6f differ from FIGS. 6a to 6c in that the hydrophobic biomolecule, exemplified as transmembrane protein (4a, 4b) or hydrophobic compound (4c), does not comprise a binding moiety.

FIGS. 7a and 7b depict particular embodiments to provide the saposin-like protein in the process of the invention. FIG. 7a differs from FIG. 7b in that the saposin-like protein has a binding moiety of natural or engineered origin. While the natural binding moiety forms part of the native amino acid sequence of the saposin-like protein, the binding moiety of engineered origin can be attached during or after synthesis of the saposin-like protein. Engineered binding moieties are optimized to bind with high affinity to their corresponding binding partner, which is the capture moiety in the process of the invention. In a further embodiment, the saposin-like protein can be in association with detergent molecules (not depicted herein).

Figure 8C:
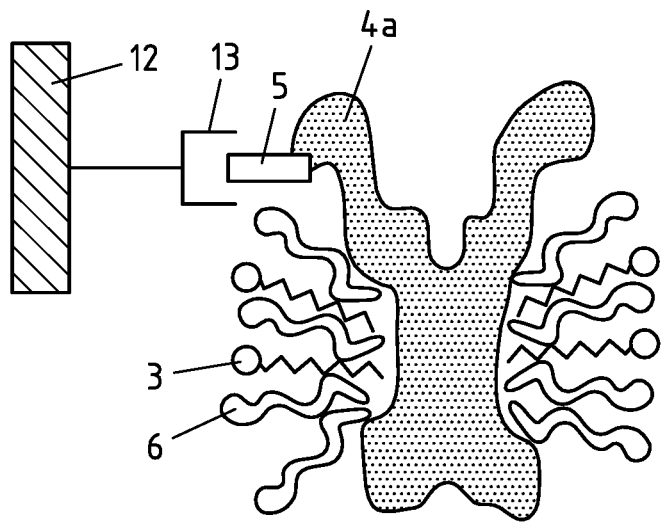
Figure 8D:
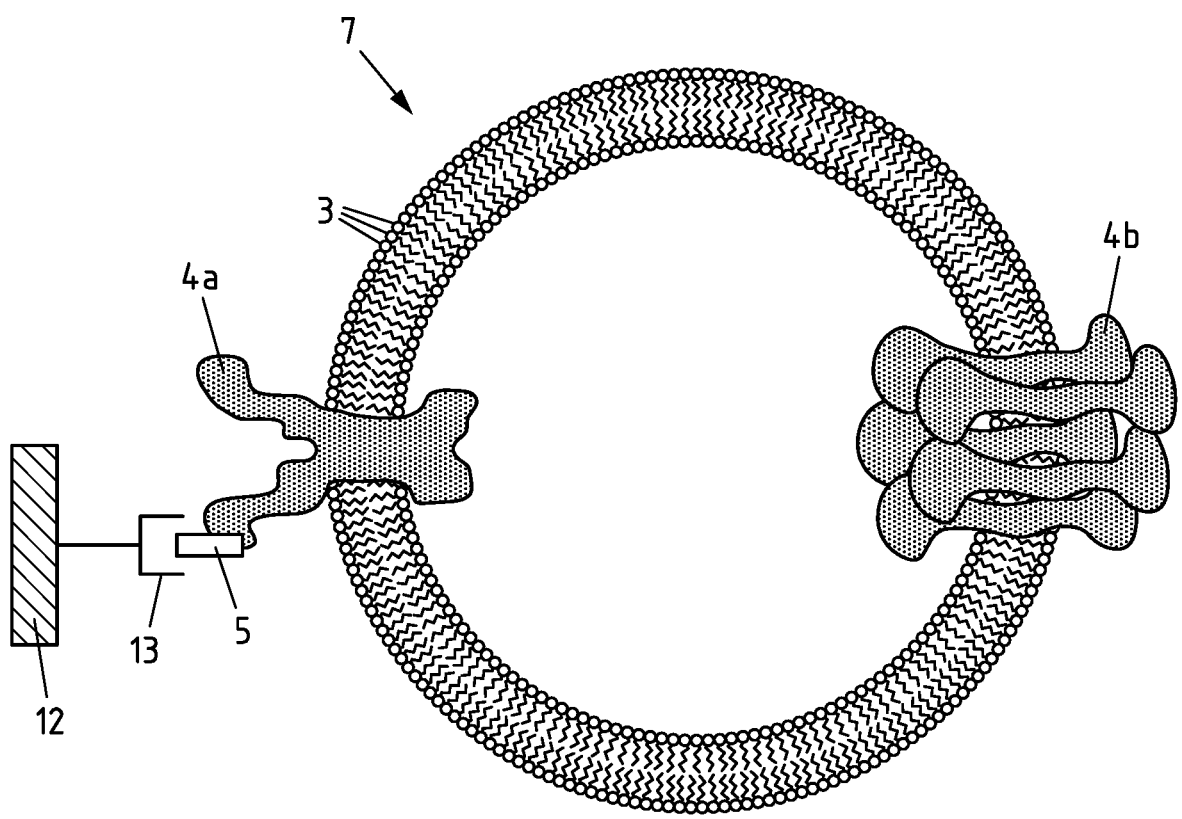

FIG. 8a to 8d show unscaled illustrations of support-bound saposin-like protein (FIG. 8a) and hydrophobic agent (FIG. 8b to 8d). The selective binding of the binding moiety in the saposin-like protein (see FIG. 8a) or in the hydrophobic agent (see FIG. 8b to 8d) to the capture moiety (13) of the support (12) is exemplified for a single capture moiety on the support. In reality the support is usually equipped with a plurality of capture moieties of the same or even different type. The interaction of the binding moiety/capture moiety recognition pair can be based on chemical bond formation, affinity based-interactions (including mediation by a bridging agent), hydrophobic interactions and/or electrostatic interactions. The support-bound saposin-like protein (2) can be in a detergent-solubilized state (not depicted herein). Also the crude membrane vesicle (7) can comprise or be associated with detergent molecules (not depicted herein). While the membrane proteins (4a, 4b) of FIG. 8d are embedded in their natural lipid environment in form of a crude membrane vesicle (7), the hydrophobic compound (4c) and the membrane protein (4a) are in an artificial detergent-solubilized state, whereby the micelle around said hydrophobic agents can be formed by lipids and detergents. In a further embodiment, the detergents used to solubilize the saposin-like protein (2) and/or the hydrophobic agents can be of the same or different chemical nature.

Figure 9A:
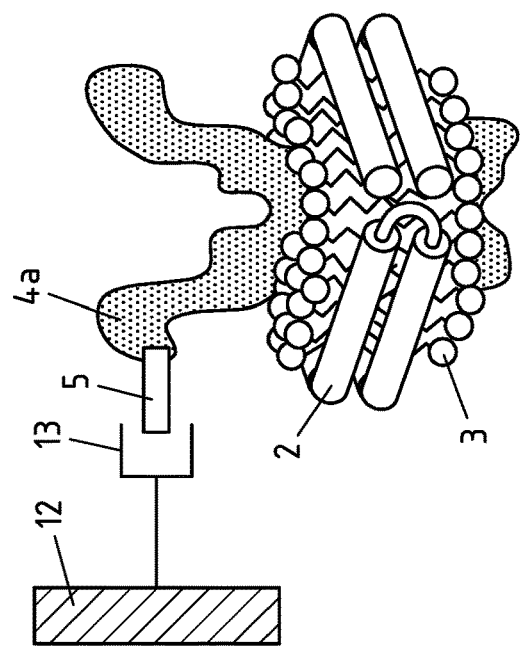
FIGS. 9a to 9c are schematic illustrations of steps b.2) and c.2) of particular embodiments, wherein the hydrophobic agent is bound to the support in step b.2) and contacted with saposin-like protein in step c.2).
Figure 9A:
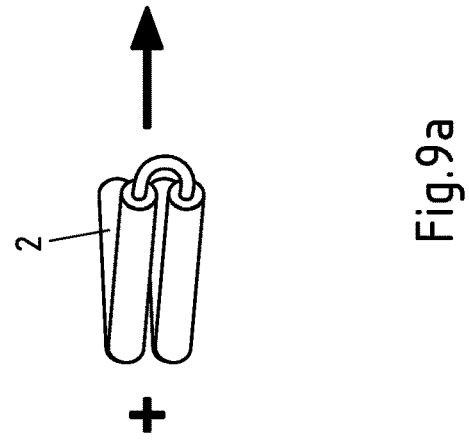
Figure 9A:
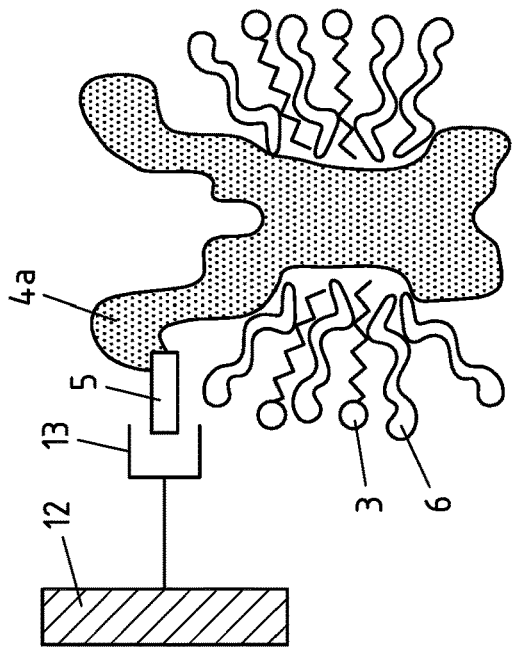
Figure 9B:
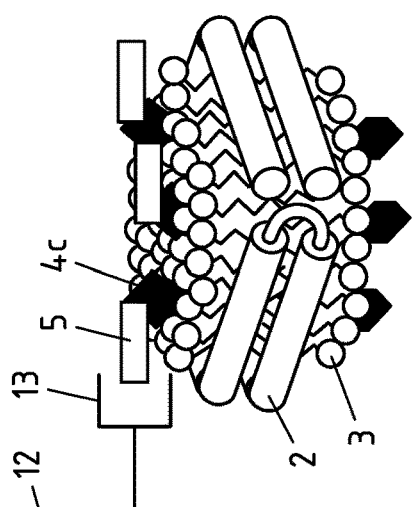
Figure 9B:
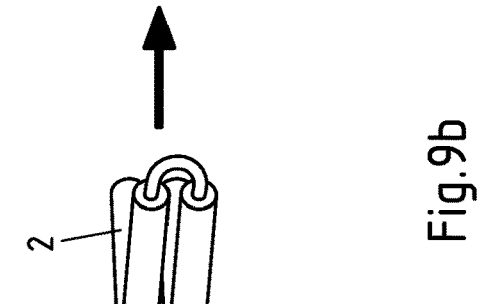
Figure 9B:
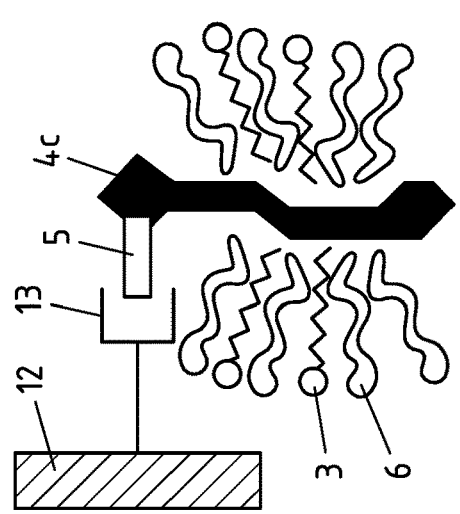
Figure 9C:
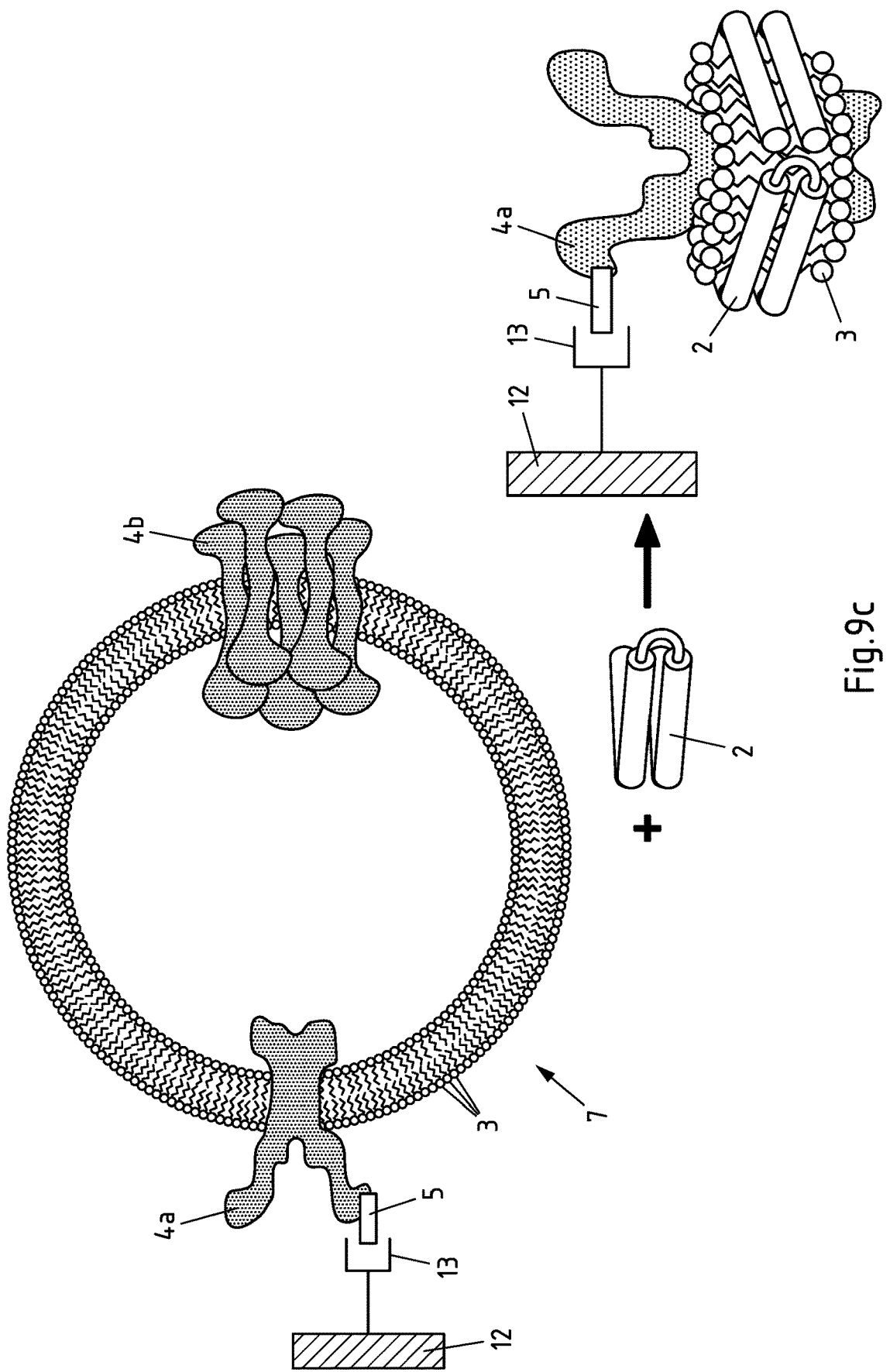

FIG. 9a to 9c show in simplified and schematic form particular embodiments of the process steps b.2) and c.2). The support-bound hydrophobic agent in form of a detergent-solubilized membrane protein (4a) (FIG. 9a), a detergent-solubilized hydrophobic compound (4c) (FIG. 9b) and a membrane protein (4c) embedded in a crude membrane vesicle (7) (FIG. 9c) are contacted with saposin-like protein (2) in step c.2), which is optionally in a detergent-solubilized state. Usually self-assembly of the particles occurs on the support directly upon contacting the support-bound hydrophobic agent with the saposin-like protein (2). Optionally additional solubilized lipids of viral, archaeal, eukaryotic and/or prokaryotic origin are added to the particle assembly reaction, which is not depicted in FIGS. 9a to 9c. The solubilized-membrane protein (4a) of FIG. 9a and the solubilized-hydrophobic compound (4c) are provided in purified form for selective binding to the support in step b.2). The assembled particle of FIGS. 9a and 9b is substantially composed of lipids (3) that have been associated with the solubilized membrane protein (4a) or hydrophobic compound (4c). Optionally, additional lipids are added to the liquid environment of the support. In FIG. 9c a crude membrane vesicle (7) is bound to the support (12). As depicted in FIG. 9c only the membrane protein (4a) bound by its binding moiety (5) to the capture moiety (13) of the support (12) remains bound to the solid support upon contacting with saposin-like protein (2) to allow self-assembly of the Salipro particle on the support. Other membrane proteins, which form initially part of the support-bound crude membrane vesicle in step b.2) and which do not present a complimentary binding moiety for the support's capture moiety, exemplified as multimeric membrane protein (4b) in crude membrane vesicle (7), are not incorporated into the support-bound Salipro particles. The embodiment depicted in FIG. 9c therefore allows the production of Salipro particles comprising a single type of membrane protein (4c) from a plurality of support-bound crude membrane vesicles in step b.2). The assembled particles are substantially free of detergents. The support-bound particles of FIG. 9a to 9c can be eluted. The elution strategy depends on the type of interaction between the capture moiety (13) of the support (12) and the binding moiety (5) in the hydrophobic agent.

Figure 10A:
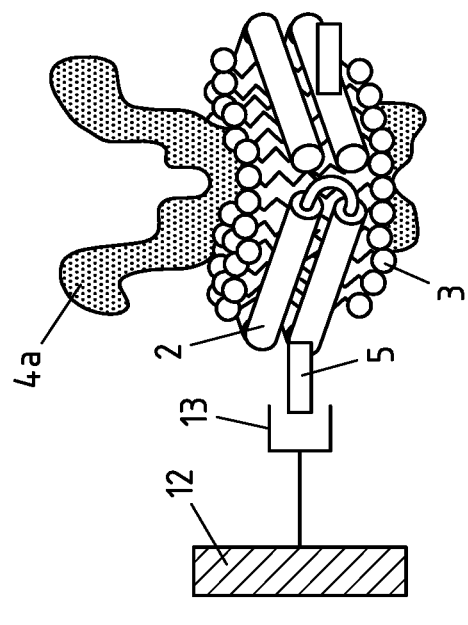
Figure 10A:
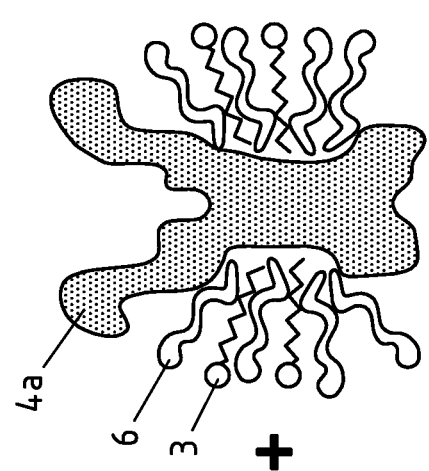
Figure 10A:
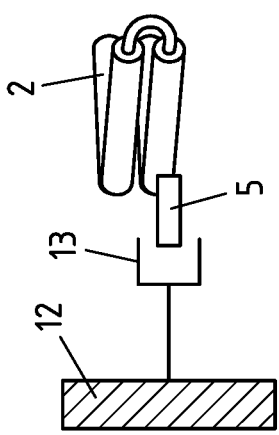

FIG. 10a to 10d show in simplified and schematic form particular embodiments of the process steps b.1) and c.1). The support-bound saposin-like protein is contacted with a detergent-solubilized membrane protein (exemplified as monomeric transmembrane protein (4a), see FIG. 10a), with crude membrane vesicles (exemplified as vesicles (7,7'), see FIG. 10b), a detergent-solubilized hydrophobic compound (4c) (see FIG. 10c) or with both, a detergent-solubilized hydrophobic compound (4c) and a membrane protein (4a) (see FIG. 10d) to allow self-assembly of the respective Salipro particles on the support in step c.1). Neighboring captured saposin-like proteins or additionally added free saposin-like proteins contribute to form an individual Salipro particle (not shown). For example, additional saposin-like protein is added during or after step c.1) to allow for the self-assembly of the saposin lipoprotein particle (not shown). The assembled particle of FIG. 10a is substantially composed of lipids (3) that have been associated with the solubilized membrane protein (4a). The solubilized protein is usually obtained by a protein purification process and is under these circumstances frequently embedded in a micelle comprising detergent molecules and lipids (3). The lipids associated with the solubilized membrane protein are often "shell lipids" of the membrane from which the membrane protein (4a) was purified. The membrane protein may be purified from its "natural" membrane, but this does not have to be the case. For example, a eukaryotic membrane protein can be overexpressed from a transgene in a prokaryotic cell, such as a bacterium, or a virus from which then the membrane protein is purified. The lipids (3) that remain associated with the detergent-solubilized eukaryotic membrane protein might therefore not form part of the "natural" lipid environment of this purified protein. The shell lipids stick tightly to the hydrophobic surfaces of the membrane protein (4a). Only optionally, further lipids are added to the liquid environment for incorporation into the Salipro particles.

Figure 10B:
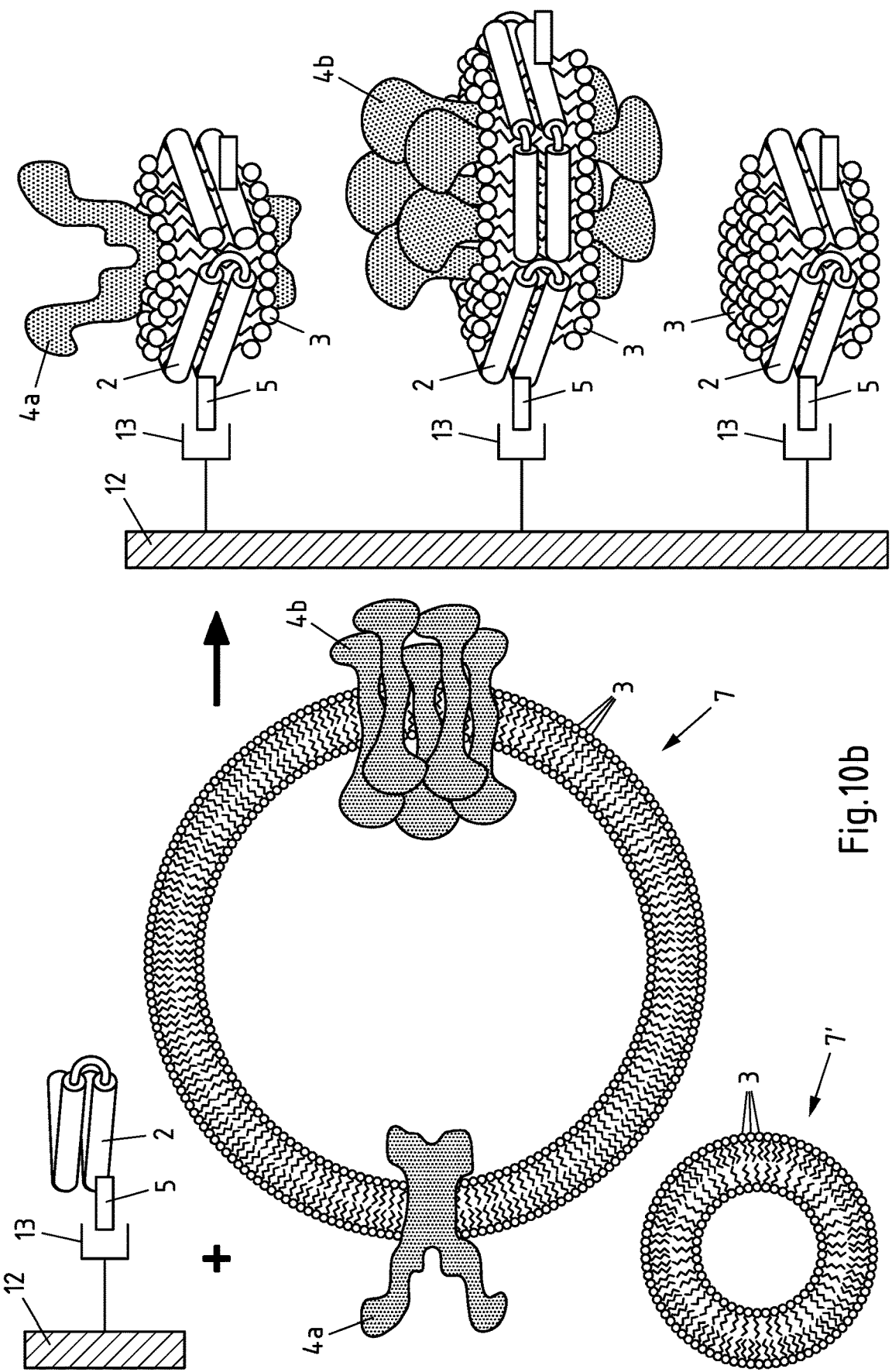

Contacting crude membrane vesicles (exemplified as vesicles (7,7') in FIG. 10b) with support-bound saposin-like protein in step c.1) (see FIG. 10b) permits production of a support-bound library of Salipro particles, i.e. the support-bound Salipro particles differ in their size and composition comprising saposin-like protein (2), lipids (3) and/or membrane proteins (4a, 4b). Even "empty" particles not comprising any hydrophobic agent can be produced. In the particles of the library the respective membrane protein (4a, 4b) is embedded in the membrane environment from which it was obtained, i.e. the membrane protein remains embedded in its "natural" lipid environment. Thus, the lipids (3) associated with the membrane proteins (4a, 4b) in the assembled Salipro particles are preferably a carry-over from the membrane protein's native lipid environment which is present in the crude membrane vesicle (7). Viral, archaeal, eukaryotic or prokaryotic membranes can serve as source membranes. The assembled particle of FIG. 10c comprises three hydrophobic compounds per particle.

Of course, the number of hydrophobic compounds incorporated into a single particle can be tuned by adjusting the molar ratio of hydrophobic compounds to lipids employed in the self-assembly reaction of step c.1). The hydrophobic compound of FIG. 10c is added to the self-assembly reaction in a solubilized state. Solubilization of hydrophobic compounds is usually achieved by detergent molecules, similar to the solubilization of hydrophobic membrane proteins. As depicted in FIG. 10c lipids can form part of the solubilized state of the hydrophobic compound. Optionally additional lipids can be added. As depicted in FIG. 11d the hydrophobic agents in form of the solubilized hydrophobic compound (4c) and the membrane protein (4a) can be applied together in step c.1). Any desired molecular ratio of solubilized hydrophobic compound to membrane protein can be chosen which influences the composition of the obtained particles. The assembled particles depicted in FIG. 10a to 10d are usually substantially free of detergents. The support-bound particles of FIG. 10a to 10d can be eluted. The elution strategy depends on the type of interaction between the capture moiety (13)/binding moiety (5) pair.

EXAMPLES

The following example serves to further explain the invention in more detail, specifically with reference to certain embodiments and Figures which, however, are not intended to limit the present disclosure.

I Abbreviations

The following abbreviations will be used:
Asp Aspartic acid
CV column volume
daGFP This kind of green fluorescent protein can be used in the same way as normal GFP using argon laser based or UV based excitation apparatus to allow the detection of fluorescence. The protein has a peak excitation of 510 nm and a peak emission of 521 nm.
EB1 elution buffer (20 mM HEPES pH 7.5, 150 mM NaCl, 400 mM Imidazol)
EB2 elution buffer (50 mM HEPES pH 7.5, 2% DDM, 0.4% CHS, 200 mM NaCl, 1 mM L-Asp, 1 mM EDTA, 1 mM TCEP and 5% Glycerol, 2.5 mM desthiobiotin)
EB3 50 mM HEPES pH 7.5, 200 mM NaCl, 10% glycerol, 250 µg/mL FLAG-peptide
EB4 50 mM HEPES pH 7.5, 200 mM NaCl, 10% glycerol supplemented with 2 mM biotin
EDTA ethylenediaminetetraacetic acid
DDM n-dodecyl-β-D-maltopyranoside
GF gel filtration buffer (20 mM HEPES pH 7.5, 150 mM NaCl)
HEPES 4-(2-hydroxyethyl)-1-piperazineethanesulfonic acid
His Histidine
HNG buffer 50 mM HEPES pH 7.5, 200 mM NaCl and 5% glycerol
HNG buffer II 50 mM HEPES pH 7.5, 200 mM NaCl and 10% glycerol
IMAC immobilized metal affinity chromatography
IPTG isopropyl β-D-1-thiogalactopyranoside
LB1 20 mM HEPES pH 7.5, 150 mM NaCl, 20 mM Imidazol
LB2 50 mM HEPES/Tris-base, pH 7.4, 50 mM NaCl buffer supplemented with 1 mM L-Asp, 1 mM EDTA, 1 mM PMSF, 1 mM TCEP, and 1:200 (v/v) dilution of mammalian protease inhibitor cocktail (Sigma)
PEI poly-ethylenimine
PMSF phenylmethylsulfonyl fluoride
SB solubilization buffer
SEC size-exclusion chromatography
SLC solute carrier
TCEP tris(2-carboxyethyl)phosphine
TEV Tobacco etch virus
Tris tris(hydroxymethyl)aminomethane
TB medium terrific broth medium
WB working buffer (50 mM HEPES pH 7.5, 2% DDM, 0.4% CHS, 200 mM NaCl, 1 mM L-Asp, 1 mM EDTA, 1 mM TCEP and 5% Glycerol)

II Purification of Saposin A

Purified saposin A used in the below experiments was prepared as follows. Saposin A protein expression was carried out using a vector with the coding region for human saposin A (SEQ ID NO: 1) inserted into a pNIC-Bsa4 plasmid and transformed and expressed in E. coli Rosetta gami-2 (DE3) (Novagen) strains. Cells were grown at 37° C. in TB medium supplemented with Tetracycline, Chloramphenicol and Kanamycin and induced with 0.7 mM IPTG. Three hours after induction, the cells were collected by centrifugation at 12.000×g for 15 min. The supernatant was discarded, the cell pellet was resuspended using lysis buffer LB1 (20 mM HEPES pH 7.5, 150 mM NaCl, 20 mM Imidazol) and disrupted by sonication. Lysates were subjected to centrifugation at 26.000×g for 30 min, the supernatant heated to 85° C. for 10 min, followed by an additional centrifugation step at 26.000×g for 30 min. Preparative IMAC purification was performed by batch-adsorption of the supernatant by end-over-end rotation with Ni Sepharose™ 6 Fast Flow medium for 60 min. After binding of saposin A to the IMAC resin, the chromatography medium was packed in a 10-mm-(i.d.) open gravity flow column and unbound proteins were removed by washing with 15 bed volumes of lysis buffer LB1. The resin was washed with 15 bed volumes of wash buffer (20 mM HEPES pH 7.5, 150 mM NaCl, 40 mM Imidazol). Saposin A was eluted by addition of five bed volumes of elution buffer EB1 (20 mM HEPES pH 7.5, 150 mM NaCl, 400 mM Imidazol). The eluate was dialyzed overnight against gel filtration buffer GF pH 7.5 (20 mM HEPES pH 7.5, 150 mM NaCl) supplemented with recombinant TEV protease. TEV protease containing an un-cleavable His-tag was removed from the eluate by passing it over 2 ml IMAC resin. Cleaved target proteins were concentrated to a volume of 5 ml using centrifugal filter units and loaded onto a HiLoad Superdex™ 200 16/60 GL column using an ÄKTAexplorer™ 10 chromatography system (both GE Healthcare). Peak fractions were pooled and concentrated to 1.2 mg/ml protein. The protein sample was flash frozen in liquid nitrogen and stored at −80° C.

III Generation of Salipro Particles on Support

Example 1

In this example, a large transmembrane transporter (SLC) is used as hydrophobic agent in alternative (II) of the process according to the invention. The lipids and the hydrophobic agent are provided in the form of a crude membrane fraction obtained from SLC-overexpressing HEK293F cells. The SLC transporter contains a Strep II-tag as binding moiety. Anti-Strep-II affinity purification beads, were used as support according to the invention. They contain anti-Strep-II capture moieties that are capable of binding the Strep II-binding moiety comprised in the SLC transporter protein. Addition of Saposin A to the support-bound SLC transporter-containing solubilized membranes allowed formation of SLC-transporter-containing saposin lipid particles that were still attached to the support via the Strep-II tag comprised in the SLC transporter protein. Thus, the assembly of the saposin lipid particles took place entirely on the support and with the endogenous lipids that were derived from the cellular membrane and still complexed with the support-bound SLC transporter protein.

1.a. Over-Expression of Membrane Protein

The coding sequence of human SLC transporter was introduced into an expression vector encoding for an N-terminal Strep-tag II followed by daGFP and a PreScission protease cleavage site. Prior to transfection, HEK293F cells (ATCC cell line, myco-plasma test negative) were grown in Excell293 medium (Sigma) supplemented with 4 mM L-glutamine (Sigma) and 5 µg ml$^{-1}$ Phenol red (Sigma-Aldrich) to densities of 2.5×10$^6$ cells ml$^{-1}$. Cells were transiently transfected with the expression vector in Freestyle293 medium (Invitrogen) using poly-ethylenimine (PEI) (Polysciences) at a density of 2.5×10$^6$ cells ml$^{-1}$, diluted with an equivalent volume of Excell293 6 h after transfection, and treated with 2.2 mM valproic acid (Sigma) 12 h after dilution of the cultures. Transfected cells then overexpressed the fusion protein Strep II-daGFP-SLC. All cells were collected at around 48 h after transfection.

1.b. Preparation of Crude Cell Membranes

Large-scale expression of the fusion protein Strep II-daGFP-SLC was performed in a 5l culture essentially as described in a. above. Cells were collected in lysis buffer (LB2) containing 50 mM HEPES/Tris-base, pH 7.4, 50 mM NaCl supplemented with 1 mM L-Asp, 1 mM EDTA, 1 mM PMSF, 1 mM TCEP, and 1:200 (v/v) dilution of mammalian protease inhibitor cocktail (Sigma), and disrupted in a cell homogenizer (EmulsiFlex-05, Avestin) via 3 runs at approximately 103,000 kPa. The resulting homogenate was clarified by centrifugation (4,500 g for 0.5 h) and the crude membranes were collected by ultracentrifugation (186,000 g for L5 h). Membranes were washed once with the LB2 buffer and finally homogenized with a douncer in a buffer containing 50 mM HEPES/Tris-base, pH 7.4, 200 mM NaCl, 1 mM L-Asp, 1 mM EDTA, 1 mM TCEP, and 10% glycerol, snap-frozen in liquid $N_2$ and stored at $-80°$ C. at 0.5 g membranes $ml^{-1}$.

1.c. Binding to Affinity Support and Elution

The following buffers were used:
Solubilization buffer (SB): 50 mM HEPES pH 7.5, 2% DDM, 0.4% CHS, 200 mM NaCl, 1 mM L-Asp, 1 mM EDTA, 1 mM TCEP and 5% Glycerol.
Working buffer (WB): 50 mM HEPES pH 7.5, 200 mM NaCl, 1 mM L-Asp, 1 mM TCEP and 5% glycerol.
Elution buffer EB2: WB supplemented with 2.5 mM desthiobiotin (dBiotin).
HNG buffer: 50 mM HEPES pH 7.5, 200 mM NaCl and 5% glycerol.

800 µl crude membranes (0.5 g membranes $ml^{-1}$) containing over-expressed SLC transporter were solubilized with 4.2 ml SB and incubated for 90 min at 4° C. using a rotating wheel. Membrane debris was removed by centrifugation at 30,000 g for 30 min followed by the addition of 900 µl equilibrated anti-Strep-II affinity purification beads (StrepTactin Sepharose beads, GE healthcare) and the total volume was corrected to 5 ml using WB. The sample was then incubated at 4° C. for 1 h to allow binding of the Strep-II tagged SLC transporter to the affinity beads. The sample was then divided onto 5 separate columns allowing to remove non-bound material by gravity flow through. The affinity beads were not washed at this stage and contained the affinity bound SCL transporter in an environment ("dead volume" of the beads) partly containing native cell membrane lipids, detergent micelles and the WB components.

Different amounts (0-4 ml) of 3.6 mg/ml Saposin were added to the corresponding columns. The mixtures were then transferred to five new tubes and the total sample volumes were corrected to 5 ml using WB as follows:
Sample 1: 0 ml Saposin A+4 ml WB
Sample 2: 0.5 ml Saposin A+3.5 ml WB
Sample 3: 1 ml Saposin A+3 ml WB
Sample 4: 2 ml Saposin A+2 ml WB
Sample 5: 4 ml Saposin A Samples 1-5 were then incubated for 1 h at 4° C. using a rotating wheel, before being transferred back to columns. Non-bound material was removed from the column using gravity flow through, followed by 6 CV washes in WB and an elution step with 4 ml elution buffer EB2. 50 µl of each eluted sample was analyzed using SEC (protein detection at 280 nm) with a Superose 6 increase, 5/150 GL column running in detergent free WB as SEC buffer.

Figure 11:
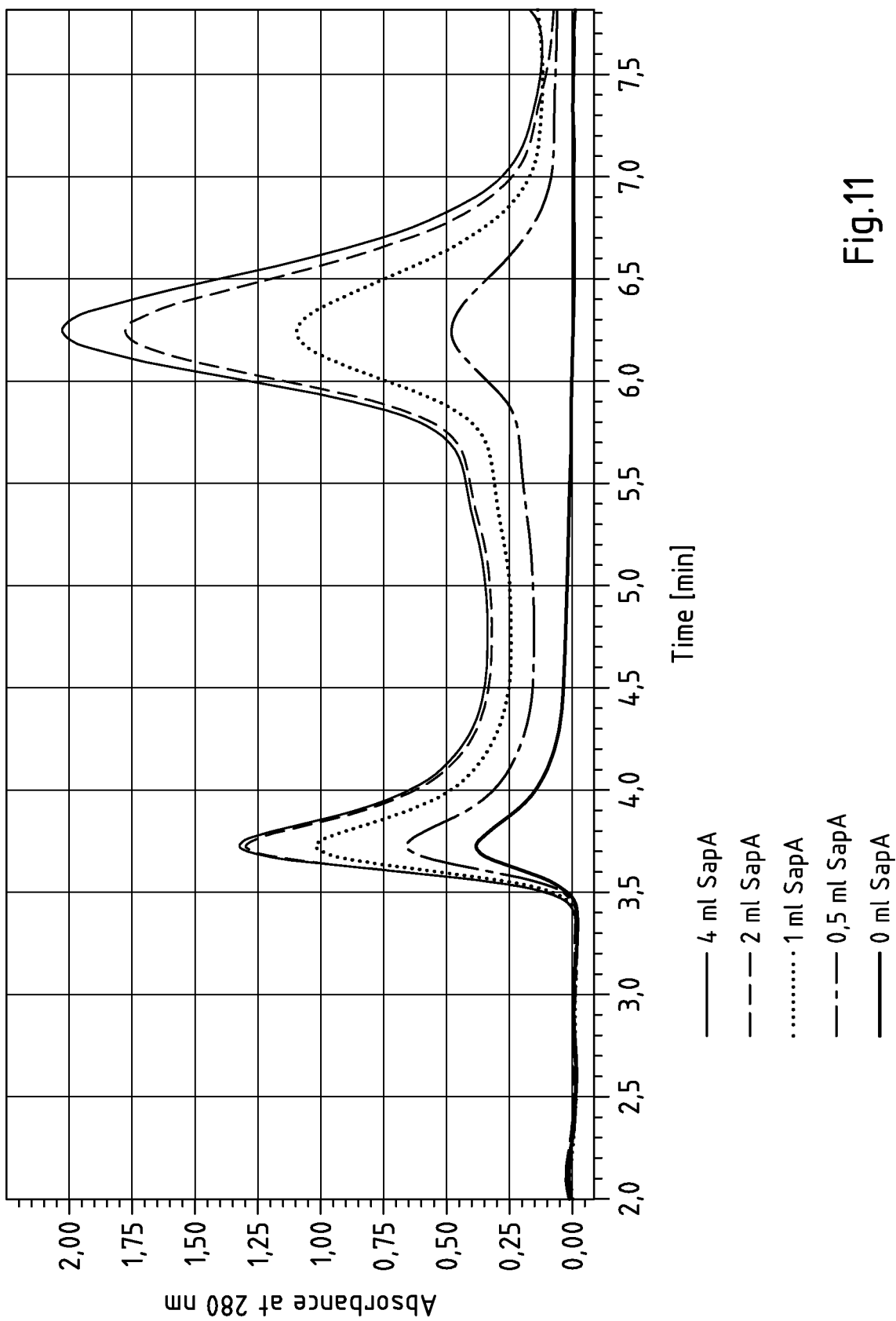
FIG. 11 shows the results of Experiment 1c.

The results are depicted in FIG. 11. The results demonstrate that saposin lipoprotein particles can be obtained even if the membrane protein, which is in complex with lipids, is bound to an affinity support. Increasing amounts of Saposin A (0.5 mL, 1 mL, 2 mL and 4 mL of Saposin A in a concentration of 3.6 mg/me also lead to increased formation of Salipro particles. As a negative control under these conditions, no Salipro particles could be obtained when Saposin A was excluded from the liquid environment (FIG. 11, sample 1).

The results depicted in FIG. 11 also reinforce that prior to elution with detergent-free buffer the support-bound Salipro particles are stable during the thorough washing steps of the column.

1.d. Analysis of Obtained Salipro Particles

The eluate obtained after incubation of the affinity beads with 4 ml SapA (see previous section c, sample 5) was concentrated using Amicon Ultra-2 centrifugal filter with a 100 kDa molecular size cut-off. 40 µl of the concentrated sample was further analyzed by SEC using a Superose 6 increase 5/150 GL column in a detergent-free HNG buffer supplemented with 1 mM L-Asp.

Figure 12A:
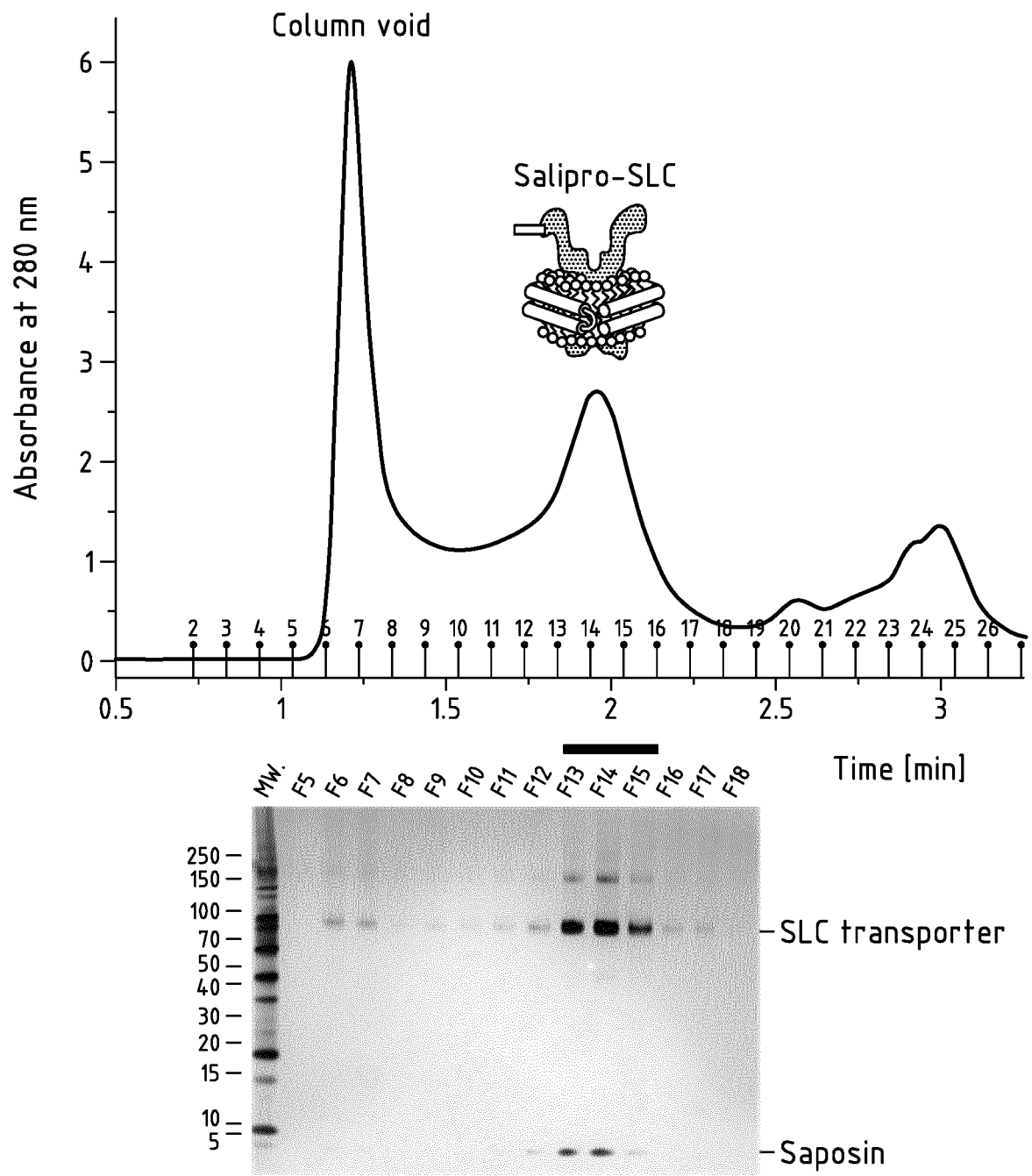
FIG. 12a to 12b shows the results of Experiment 1 d.

Analysis of the SEC fractions by SDS-PAGE indicates (FIG. 12a) that mainly fractions 13, 14 and 15 contain purified Salipro particles, containing the SLC transporter and Saposin.

Figure 12B:
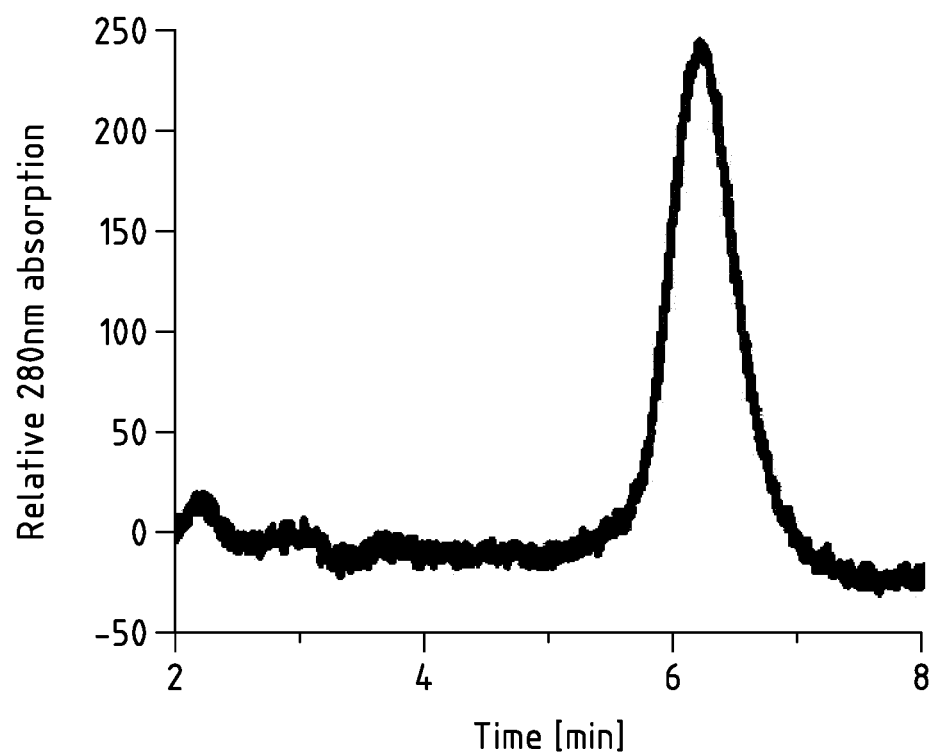

To further validate the homogeneity of the reconstituted Salipro particles, 20 µl from fraction 14 were further analyzed by SEC using a Superose 6 increase 5/150 GL column in detergent free-HNG buffer supplemented with 1 mM L-Asp. The corresponding SEC profile (FIG. 12b) further demonstrates the stability and homogeneity of the Salipro particles when reconstituted on the affinity beads.

The data presented herein clearly demonstrate that it is possible to reconstitute hydrophobic agents into Saposin particles while one of the particle components is bound to an affinity support. The data also shows that crude membranes can be used in the process of the invention.

IV Generation of Salipro Particles from Whole Cells

Example 2

In this example, a membrane protein is used as hydrophobic agent in alternative (II) of the process according to the invention. The lipids and the hydrophobic agent are provided in the form of intact cells, i.e. human embryonic kidney (HEK) cells, overexpressing the membrane protein. Said HEK cells are only contacted with a detergent without performing a mechanical cell lysis step. The eukaryotic membrane protein contains a FLAG-tag as binding moiety. Anti-FLAG affinity purification beads are used as support according to the invention. They contain anti-FLAG capture moieties that are capable of binding the FLAG-binding moiety comprised in the eukaryotic membrane protein. Addition of Saposin A to the support-bound eukaryotic membrane protein comprised in the detergent-treated membranes allows formation of saposin lipid particles containing the eukaryotic membrane protein. Thus, in this example, the assembly of the saposin lipid particles takes place entirely on the support and with the endogenous lipids that are provided in the form of detergent-treated whole cells expressing the to-be-included eukaryotic membrane protein of interest.

2.a. Over-Expression of Membrane Protein

The coding sequence of the eukaryotic membrane protein is introduced into an expression vector encoding for an N-terminal FLAG-tag. Prior to transfection, HEK 293F cells are grown in 293 Freestyle culture media and transfected using the PEI-Max reagent using the protocol provided by the manufacturers (ThermoFisher). Transfected cells then overexpress the membrane protein. All cells are collected at around 48 hours_post transfection.

2.b. Preparation of Solubilized Membranes

The cells overexpressing the FLAG-tagged eukaryotic membrane protein are harvested to a cell pellet. The cell pellet is then dissolved in HNG buffer II, additionally comprising a 25× protein inhibitor cocktail at a final concentration of 2×. Subsequently, a solution comprising 10% GDN in water (w/v) is added to the resuspended cells to a final concentration of 1% GDN (w/v). The sample is then incubated on a rotating wheel in a cold cabinet for 5 min. Afterwards, the sample is centrifuged at 5000 g at 4° C. for 5 min. The supernatant comprising the solubilized material, including the detergent-treated membranes, is recovered and incubated for another 50 min on a rotating wheel in a cold cabinet. After this incubation step, the supernatant is centrifuged at 30,000 g and 4° C. for 30 min to remove membrane debris and then used in the next step 2.c for binding to the affinity support.

2.c. Binding to Affinity Support and Elution

The following buffers are used:
HNG buffer II: 50 mM HEPES pH 7.5, 200 mM NaCl and 10% glycerol
EB3: 50 mM HEPES pH 7.5, 200 mM NaCl, 10% glycerol, 250 µg/mL FLAG-peptide 4 columns allowing to remove non-bound material by gravity flow through are prepared by loading each column with 100 µl of equilibrated M2 anti-FLAG affinity purification beads (SigmaAldrich. Afterwards 500 µl of solubilized membranes obtained in step 2.b are added to each column. The flow-through is then re-passed three times through the column to allow efficient binding of the FLAG-tagged eukaryotic membrane protein to the affinity beads. The affinity beads loaded with the FLAG-tagged eukaryotic membrane protein are not washed at this stage and contain the affinity bound eukaryotic membrane protein in an environment ("dead volume" of the beads) partly containing native cell membrane lipids and detergent micelles and HNG buffer II components.

Different amounts (0-6 ml) of 1 mg/ml Saposin A are added to the corresponding columns.
Sample 1: 1 ml HNG buffer II
Sample 2: 1 ml Saposin A
Sample 3: 3 ml Saposin A
Sample 4: 6 ml Saposin A The mixtures are then transferred to four new tubes and incubated for 25 min at 4° C. using a rotating wheel, before being transferred back to the columns. Non-bound material is removed from the column using gravity flow through, followed by 10 CV washes in HNG buffer II and an elution step with 500 µl elution buffer EB3.

2.d. Analysis of Salipro Particles

The eluates obtained after incubation of the affinity beads with different amounts of SapA (see previous section 2.c, samples 1 to 4) are concentrated using Amicon Ultra-2 centrifugal filters (10 kDa NMWL) at 13000 g and 4° C. The concentrated samples are further analyzed by SEC using a Superose 6 increase 5/150 GL column in a detergent-free HNG buffer II to detect formed Salipro particles.

It is expected that with the aforementioned experimental workflow saposin lipoprotein particles can be obtained from intact cells as starting material, which have not been subjected to a mechanical cell lysing and while the eukaryotic membrane protein of interest is bound to an affinity support.

As a negative control under these conditions, no Salipro particles should be obtained when Saposin A is excluded from the liquid environment.

V Generation of Salipro Particles on Support

Example 3

In this example, the reconstitution of Salipro particles was carried out according to alternative (I) of the process of the invention, i.e. Saposin was immobilized on an affinity support. To this end, Saposin was biotinylated and bound to an avidin affinity bead matrix. Contacting the support-bound Saposin with additional untagged Saposin, lipids and optionally a hydrophobic agent allowed formation of Salipro particles according to the invention. Thus, assembly of the saposin lipid particles took place on the support.

3a. Preparation of Biotinylated Saposin A

Saposin A was biotinylated using EZ-Link®NHS-Biotin Reagents (Thermo Fisher, reference 21343) according to the manufacturer's protocol. Quantification of the biotin number per Saposin A was then performed with Quant*Tag Biotin Kit (Vector laboratory, BDK-2000) and showed that 1.1 biotins per Saposin A molecule were present.

3.b. Binding to Affinity Support and Elution

Monomeric avidin matrix (Thermo Fisher 20228) was prepared and washed according to the manufacturer's protocol. The biotinylated Saposin A was bound to the prepared avidin affinity matrix. For each sample, 100 µl of biotinylated Saposin A (1.2 mg/ml) were bound to 25 µl of avidin affinity matrix by passing the biotinylated Saposin A three times over the matrix, which was contained in a column (BioRad, Polyprep Chromatography column, art.nr 7311550). The affinity matrix was then extensively washed with HNG buffer II to ensure removal of non-bound Saposin A.

With the Saposin A loaded avidin affinity matrix, two different particle assembly conditions were evaluated: In sample 1, brain lipids and untagged Sapsosin A were added to the affinity resin with pre-immobilized Saposin A. In sample 2, brain lipids, a membrane protein (bacterial ion channel membrane protein T2) and untagged Saposin A were added to affinity resin with pre-immobilized Saposin A.

The brain lipid solution was prepared by dissolving 5 mg/ml brain lipids (Sigma-Aldrich) in 0.5% DDM and pre-incubated 5 minutes at 37° C.

The bacterial ion channel membrane protein T2 was purified as previously described in F Guettou et al., Nature structural & Molecular Biology, 21; 728-731, 2014.

The particle assembly conditions for samples 1 to 2 were as follows:
Sample 1: 16 µl brain lipid solution were added to the affinity resin with pre-immobilized Saposin A and incubated 5 min at room temperature before adding 100 µl non-tagged Saposin A (1.2 mg/ml).
Sample 2: 16 µl brain lipid solution were mixed with 8 µl T2 (10 mg/ml) and incubated 5 min at 37° C., before adding the mixture to the affinity resin with pre-immobilized Saposin A. The sample was then incubated at room temperature for 5 min before adding 100 µl non-tagged Saposin A (1.2 mg/ml).

The two samples were then incubated simultaneously at room temperature on a rotating wheel for 25 min. Subsequently, the following buffers were used to treat the sample columns:
HNG buffer II: 50 mM HEPES pH 7.5, 150 mM NaCl and 10% glycerol EB4: HNG buffer supplemented with 2 mM biotin (Thermo Fisher 29129)

The affinity beads were washed extensively with detergent-free HNG buffer II (3 times using 10 CV) and immobilized samples were eluted using the elution buffer EB4.

3.c. Analysis of the Obtained Salipro Particles

The eluted samples were subjected to analytic SEC, using a Superdex™ 200 5/150 GL analytical gel filtration column running in HNG buffer II.

Figure 13:
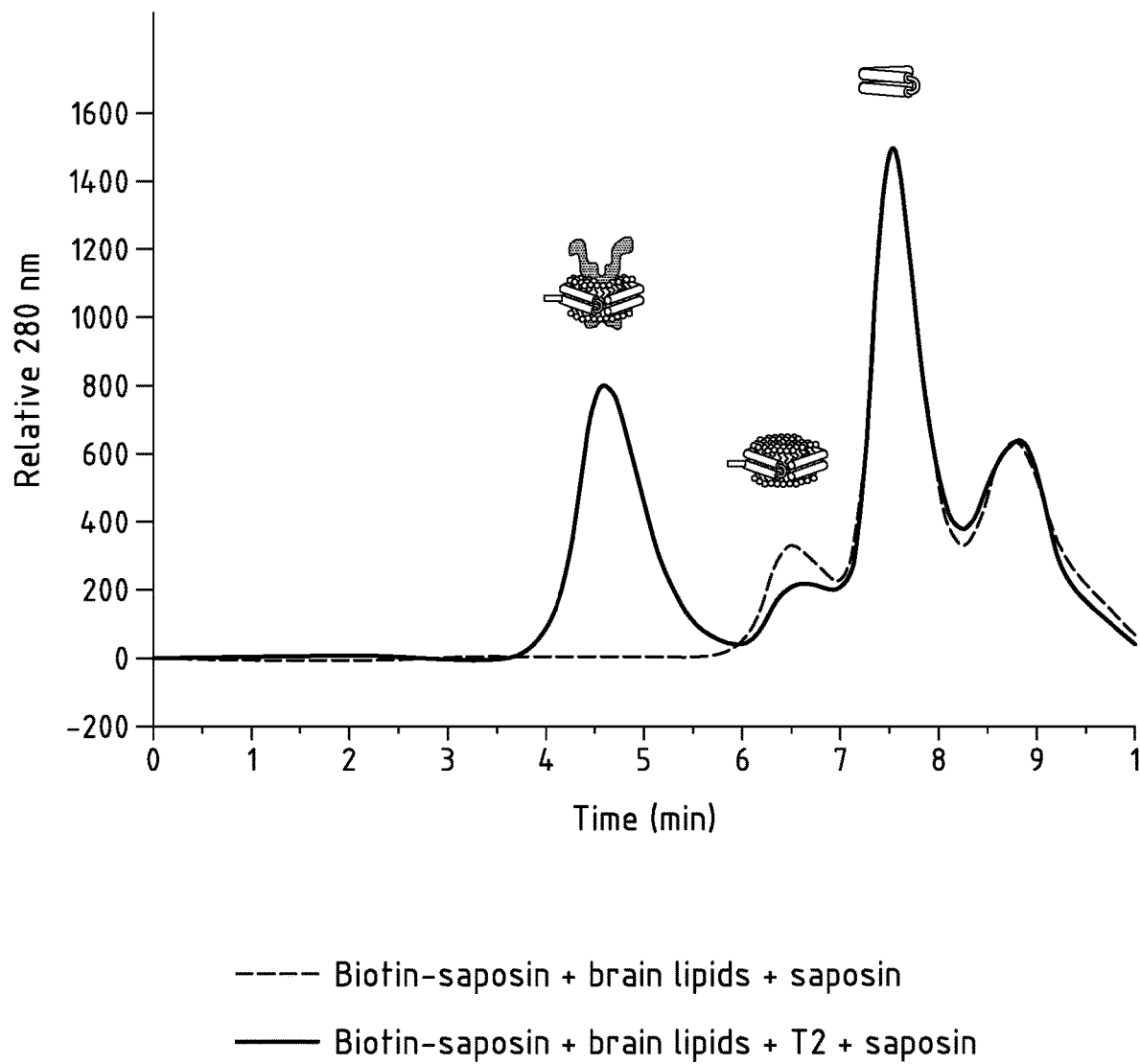
FIG. 13 shows the results of Experiment 3c.
Figure 14A:
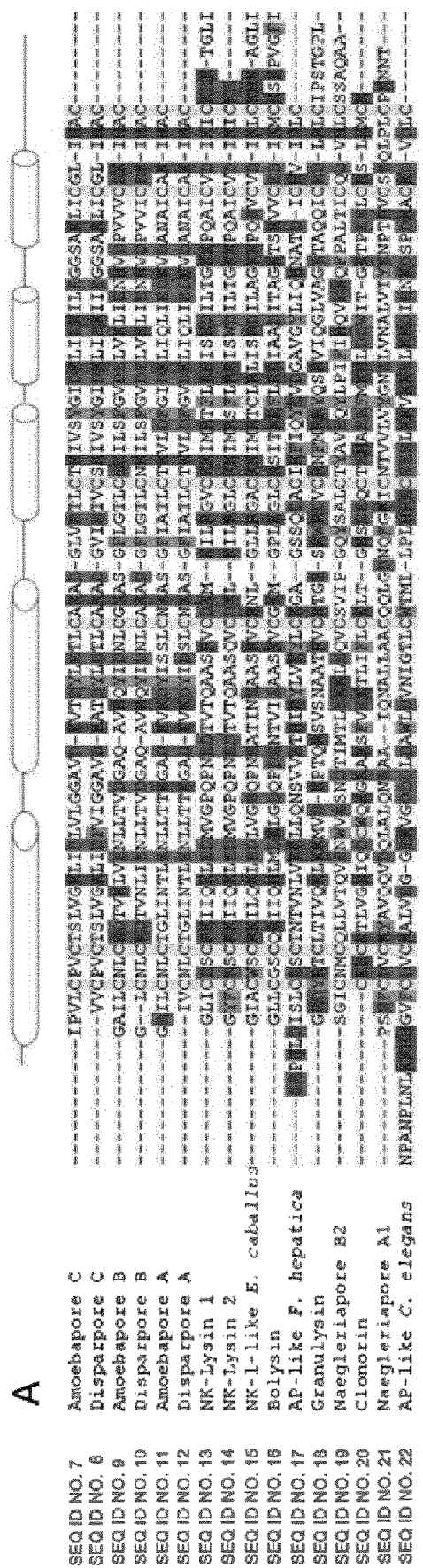

The results are shown in FIG. 13. For sample 1 and 2 Salipro particles were detected in the elution profile (see SEC peak at 6.4 min for sample 1 and SEC peak at 4.5 min for sample 2 of FIG. 13). Thus, the immobilized Saposin A enabled Salipro particle assembly to take place on the affinity support.

Altogether, the data presented herein clearly demonstrate that it is possible to reconstitute Salipro particles using different starting materials while one of the particle components is bound to an affinity support.

The invention claimed is:

1. A process for producing a saposin lipoprotein particle, wherein the produced saposin lipoprotein particle comprises
   a saposin-like protein,
   lipids, and
   a hydrophobic agent wherein the hydrophobic agent is a membrane protein and
(I) wherein the process comprises the following steps:
   a) providing the lipids and the hydrophobic agent;
   b.1) immobilizing the saposin-like protein to a support that is capable of selectively binding the saposin-like protein to the support in a liquid environment, to obtain an immobilized saposin-like protein;
   c.1) contacting the immobilized saposin-like protein with the lipids and the hydrophobic agent; to allow for the self-assembly of the saposin lipoprotein particle on the support, to obtain an immobilized saposin lipoprotein particle;
   wherein the saposin-like protein is not contacted with the lipids and the hydrophobic agent before the saposin-like protein is immobilized to the support in step b.1);
   d) optionally eluting the immobilized saposin lipoprotein particle;
   or
(II) wherein alternatively the process comprises the following steps:
   a) providing the hydrophobic agent and the lipids;
   b.2) immobilizing the hydrophobic agent and the lipids to a support that is capable of selectively binding the hydrophobic agent and the lipids to the support, to obtain an immobilized hydrophobic agent and immobilized lipids;
   c.2) contacting the immobilized hydrophobic agent and the immobilized lipids with the saposin-like protein to allow for the self-assembly of the saposin lipoprotein particle on the support, to obtain an immobilized saposin lipoprotein particle; wherein the hydrophobic agent and the lipids are not contacted with the saposin-like protein before the hydrophobic agent and the lipids are immobilized to the support in step b.2);
   d) optionally eluting the immobilized saposin lipoprotein particle.

2. The process according to claim 1, wherein the support comprises a capture moiety, and the saposin-like protein comprises a binding moiety, wherein the capture moiety is capable of selectively binding the binding moiety in the saposin-like protein.

3. The process according to claim 1, wherein the support comprises a capture moiety, and the hydrophobic agent comprises a binding moiety, wherein the capture moiety is capable of selectively binding the binding moiety in the hydrophobic agent.

4. The process according to claim 1, wherein the support is in the form of
   i. beads,
   ii a bed,
   iii. a membrane,
   iv. a solid support; or
   v. combinations thereof.

5. The process according to claim 1, wherein the lipids are selected from, the group consisting of viral, archaeal, eukaryotic and prokaryotic lipids, and mixtures thereof.

6. The process according to claim 1, wherein in steps a) of process (I) or (II), the hydrophobic agent and the lipids are provided in form of a viral, archaeal, eukaryotic or prokaryotic membrane, which comprises the hydrophobic agent and the lipids that are to be incorporated into the saposin lipoprotein particles.

7. The process according to claim 6, wherein in step c.1) the immobilized saposin-like protein is contacted with the viral, archaeal, eukaryotic or prokaryotic membrane provided in step a) to allow formation of a library of saposin like particles wherein the library comprises a heterogenic mixture of saposin lipoprotein particles with different membrane lipid and membrane protein compositions.

8. The process according to claim 1, wherein the saposin-like protein is saposin A, saposin B, saposin C, saposin D or a derivative or truncated form thereof which is capable of forming saposin lipoprotein particles in the process of claim 1.

9. The process according to claim 8, wherein the derivative or truncated form is selected from
i. a protein having at least 20% sequence identity to the full length sequence of SEQ ID NO. 1, 2, 3, 4, 5 or 6; and
ii. a protein comprising the sequence of SEQ ID NO. 1, 2, 3, 4, 5 or 6 in which 1 to 40 amino acids have been deleted, added, inserted and/or substituted.

10. The process according to claim 1, wherein the membrane protein is selected from the group consisting of, an integral transmembrane protein, an integral monotropic membrane protein, and a peripheral membrane protein.

11. The process according to claim 1, wherein the hydrophobic agent, the lipids and/or the saposin-like protein is in a detergent-solubilized state and wherein optionally the detergent is selected from the group consisting of alkylbenzenesulfonates or bile acids, cationic detergents and non-ionic or zwitterionic detergents, saponins and structurally related synthetic detergents, alkyl glycosides, glucosides, maltose-neopentyl glycol (MNG) amphiphiles, amphiphilic polymers, styrene maleic acid co-polymer (SMA), macrocyclic or cyclic oligomers based on a hydroxyalkylation product of a phenol and an aldehyde, and mixtures thereof.

12. The process according to claim 1, wherein
i. the particles obtained in at least one of step c.2) and/or c.1) are disc-shaped;
ii. the particles of at least one of step c.2) and c.1) have an average maximum diameter of from 2 nm to 200 nm;
iii. the self-assembly of the particle in at least one of step c.2) and c.1) is carried out at a pH from 2.0 to 10.0.

13. The process according to claim 9, wherein the protein having at least 20% sequence identity to the full length sequence of SEQ ID No. 1, 2, 3, 4, 5 or 6 is amphipathic, forms at least one alpha helix, and is capable of self-assembling together with lipids into lipoprotein particles when employed in the process of claim 1.

14. The process according to claim 11, wherein the zwitterionic detergents are selected from the group consisting of lauryl-dimethyl amine-oxides (LDAO), Fos-Cholines, and CHAPS/CHAPSO.

15. The process according to claim 11, wherein the saponin is Digitonin.

16. The process according to claim 11, wherein the structurally related synthetic detergent is glyco-diosgenin.

17. The process according to claim 11, wherein the alkyl glycosides are selected from the group consisting of short, medium or longer chain alkyl maltosides.

18. The process according to claim 17, wherein a short, medium or longer chain alkyl maltoside is n-Dodecyl b-D-maltoside.

19. The process according to claim 12, wherein the particles obtained in step c.2 and/or c.1 are disc-shaped and do not comprise a hydrophilic or aqueous core.

20. The process according to claim 12, wherein the particles of step c.2 and/or c.1 have an average maximum diameter of 3 nm to 150 nm.

* * * * *